US005983120A

United States Patent [19]
Groner et al.

[11] Patent Number: 5,983,120
[45] Date of Patent: Nov. 9, 1999

[54] METHOD AND APPARATUS FOR REFLECTED IMAGING ANALYSIS

[75] Inventors: Warren Groner, Great Neck, N.Y.; Richard G. Nadeau, North East, Md.

[73] Assignee: Cytometrics, Inc., Philadelphia, Pa.

[21] Appl. No.: 08/860,363

[22] PCT Filed: Oct. 21, 1996

[86] PCT No.: PCT/US96/16905

§ 371 Date: Jun. 5, 1997

§ 102(e) Date: Jun. 5, 1997

[87] PCT Pub. No.: WO97/15229

PCT Pub. Date: May 1, 1997

Related U.S. Application Data

[60] Provisional application No. 60/005,836, Oct. 23, 1995, provisional application No. 60/016,040, Apr. 23, 1996, provisional application No. 60/016,036, Apr. 23, 1996, provisional application No. 60/016,037, Apr. 23, 1996, provisional application No. 60/016,039, Apr. 23, 1996, and provisional application No. 60/020,685, Jun. 27, 1996.

[51] Int. Cl.$^6$ ........................................... A61B 5/00
[52] U.S. Cl. ........................... 600/310; 600/476; 356/39; 356/364; 382/134
[58] Field of Search .................................... 600/310, 322, 600/473, 476, 479; 356/39–42, 364, 369, 445; 382/128, 130, 133, 134, 274

[56] References Cited

U.S. PATENT DOCUMENTS

| Re. 30,007 | 5/1979 | Steuer et al. ............................ 324/30 B |
| 3,922,598 | 11/1975 | Steuer et al. ............................ 324/30 R |
| 4,071,020 | 1/1978 | Pugliese ................................... 128/2 A |
| 4,191,940 | 3/1980 | Polcyn et al. .................... 340/146.3 B |
| 4,194,217 | 3/1980 | van den Bosch ......................... 358/93 |
| 4,239,048 | 12/1980 | Steuer ..................................... 128/666 |
| 4,241,738 | 12/1980 | Lübbers et al. ......................... 128/666 |
| 4,305,398 | 12/1981 | Sawa ........................................ 128/633 |

(List continued on next page.)

FOREIGN PATENT DOCUMENTS

| 0 282 210 B1 | 11/1992 | European Pat. Off. . |
| 0 641 542 A2 | 3/1995 | European Pat. Off. . |
| 0 683 386 A1 | 11/1995 | European Pat. Off. . |
| 0 712 602 A2 | 5/1996 | European Pat. Off. . |
| 0 714 628 A1 | 6/1996 | European Pat. Off. . |
| WO 93/07801 | 4/1993 | WIPO . |
| WO 93/13706 | 7/1993 | WIPO . |
| WO 97/24066 | 7/1997 | WIPO . |

OTHER PUBLICATIONS

Zhou, Shixin, et al., "Electronic endoscipy using dual polarizing filters to reduce the specular component," *Optics Communications 122*, Dec. 15, 1995, pp. 1–8.

Bacus, "Quantitative Measurement of Red Blood Cell Central Pallor and Hypochromasia," *Analytical and Quantitative Cytology*, pp. 123–130, Mar. 3, 1980.

Bacus, "Quantitative Morphological Analysis of Red Blood Cells," *Blood Cells*, 6, pp. 295–314, 1980.

Bentley et al., "The Use of an Image Analysing Computer for the Quantitation of Red Cell Morphological Characteristics," *British Journal of Haematology*, pp. 81–88, 1975.

(List continued on next page.)

*Primary Examiner*—Eric F. Winakur
*Attorney, Agent, or Firm*—Sterne, Kessler, Goldstein & Fox, P.L.L.C.

[57] ABSTRACT

Reflected imaging is used to perform non-invasive, in vivo analysis of a subject's vascular system. A raw reflected image is normalized with respect to the background to form a corrected reflected image. An analysis image is segmented from the corrected reflected image to include a scene of interest for analysis. The method and apparatus can be used to determine such characteristics as the hemoglobin concentration per unit volume of blood, the number of white blood cells per unit volume of blood, a mean cell volume, the number of platelets per unit volume of blood, and the hematocrit. Cross-polarizers can be used to improve visualization of the reflected image.

103 Claims, 24 Drawing Sheets

U.S. PATENT DOCUMENTS

| | | | |
|---|---|---|---|
| 4,331,132 | 5/1982 | Mukasa | 128/6 |
| 4,338,024 | 7/1982 | Bolz et al. | 356/23 |
| 4,407,295 | 10/1983 | Steuer et al. | 128/670 |
| 4,453,266 | 6/1984 | Bacus | 382/6 |
| 4,504,263 | 3/1985 | Steuer et al. | 604/65 |
| 4,608,344 | 8/1986 | Carter et al. | 436/34 |
| 4,672,196 | 6/1987 | Canino | 250/225 |
| 4,683,208 | 7/1987 | Aoyama et al. | 436/12 |
| 4,711,248 | 12/1987 | Steuer et al. | 128/748 |
| 4,786,165 | 11/1988 | Yamamoto et al. | 356/23 |
| 4,805,623 | 2/1989 | Jöbsis | 128/633 |
| 4,810,658 | 3/1989 | Shanks et al. | 436/172 |
| 4,819,752 | 4/1989 | Zelin | 128/633 |
| 4,854,699 | 8/1989 | Edgar, Jr. | 356/41 |
| 4,863,265 | 9/1989 | Flower et al. | 356/41 |
| 4,927,264 | 5/1990 | Shiga et al. | 356/41 |
| 4,998,533 | 3/1991 | Winkelman | 128/637 |
| 5,016,173 | 5/1991 | Kenet et al. | 364/413.13 |
| 5,030,000 | 7/1991 | Kanda | 356/40 |
| 5,031,629 | 7/1991 | DeMarzo | 128/670 |
| 5,036,545 | 7/1991 | Iida et al. | 382/62 |
| 5,064,282 | 11/1991 | Curtis | 356/40 |
| 5,091,963 | 2/1992 | Litt et al. | 382/8 |
| 5,104,794 | 4/1992 | Kondo et al. | 435/25 |
| 5,146,091 | 9/1992 | Knudson | 250/341 |
| 5,149,503 | 9/1992 | Kohno et al. | 422/82.05 |
| 5,195,963 | 3/1993 | Yafuso et al. | 604/49 |
| 5,200,345 | 4/1993 | Young | 436/63 |
| 5,218,207 | 6/1993 | Rosenthal | 250/341 |
| 5,219,400 | 6/1993 | Jacot et al. | 128/633 |
| 5,259,382 | 11/1993 | Kronberg | 128/633 |
| 5,277,181 | 1/1994 | Mendelson et al. | 128/633 |
| 5,288,646 | 2/1994 | Lundsgaard et al. | 436/165 |
| 5,348,003 | 9/1994 | Caro | 128/633 |
| 5,351,686 | 10/1994 | Steuer et al. | 128/633 |
| 5,353,790 | 10/1994 | Jacques et al. | 128/633 |
| 5,357,960 | 10/1994 | Schmidtke et al. | 128/633 |
| 5,361,758 | 11/1994 | Hall et al. | 128/633 |
| 5,370,114 | 12/1994 | Wong et al. | 128/633 |
| 5,372,136 | 12/1994 | Steuer et al. | 128/633 |
| 5,383,452 | 1/1995 | Buchert | 128/633 |
| 5,394,199 | 2/1995 | Flower | 351/206 |
| 5,398,681 | 3/1995 | Kupeshmidt | 128/633 |
| 5,399,852 | 3/1995 | Zheng et al. | 250/225 |
| 5,427,915 | 6/1995 | Ribi et al. | 435/7.92 |
| 5,436,978 | 7/1995 | Kasdan | 382/133 |
| 5,448,992 | 9/1995 | Kupershmidt | 128/633 |
| 5,449,623 | 9/1995 | Tokuda et al. | 436/97 |
| 5,456,253 | 10/1995 | Steuer et al. | 128/633 |
| 5,499,627 | 3/1996 | Steuer et al. | 128/633 |
| 5,515,163 | 5/1996 | Kupershmidt et al. | 356/338 |
| 5,526,808 | 6/1996 | Kaminsky | 128/632 |
| 5,547,849 | 8/1996 | Baer et al. | 435/7.24 |
| 5,548,404 | 8/1996 | Kupershmidt et al. | 356/368 |
| 5,567,869 | 10/1996 | Hauch et al. | 73/64.41 |
| 5,588,428 | 12/1996 | Smith et al. | 128/653.1 |
| 5,589,932 | 12/1996 | García-Rubio et al. | 356/39 |
| 5,598,842 | 2/1997 | Ishihara et al. | 128/637 |
| 5,621,532 | 4/1997 | Ooki et al. | 356/444 |
| 5,636,637 | 6/1997 | Guiolet et al. | 600/476 |
| 5,720,284 | 2/1998 | Aoyagi et al. | 128/633 |
| 5,722,398 | 3/1998 | Ishihara et al. | |

OTHER PUBLICATIONS

Braley et al., *Stereoscopic Atlas of Slit–Lamp Biomicroscopy*; vol. 1, The C. V. Mosby Company, Saint Louis, pp. 11, 15, 16, 27, and 66, 1970.

Brown, "A New Instrument for the Simultaneous Measurement of Total Hemoglobin, % Oxyhemoglobin, % Carboxyhemoglobin, % Methemoglobin, and Oxygen Content in Whole Blood," *IEEE Transactions on Biomedical Engineering*, vol. BME–27, No. 3, pp. 132–138, Mar. 1980.

Brown et al., ed., *Chemical Diagnosis of Disease*, Elsevier/North–Holland Biomedical Press, Amsterdam, p. 885, 1979.

Chiabrera et al., "Automated Absorption Image Cytometry of Electromagnetically Exposed Frog Erythrocytes," *Cytometry*, vol. 1, No. 1, pp. 42–48, 1980.

*Clinical Chemistry; Principles and Techniques*, pp. 28, 30, 37, and 44, date unknown.

Dallow, *Television Ophthalmoscopy*, Thomas Books, Springfield, Illinois, pp. 40, 41, 43, 44, 46, 48, 68–71, 78, 79, 1970.

Deindoerfer et al., "Automated Intelligent Microscopy (AIM) and its Potential Application in the Clinical Laboratory," *Clincal Chemistry*, vol. 28, No. 9, pp. 1910–1916, Sep. 1982.

Devaney et al., "Continuous Measurement of Vascular Diameters via Television Microscopy," *ISA Transactions*, vol. 15, No. 1, pp. 73–78, 1976.

"diff3; The automation you need . . . ," date unknown.

"The differential system of choice offers you a choice of systems," Geometric Data, SmithKline, date unknown.

Ellis et al., "Measurement of the Lineal Density of Red Blood Cells in Capillaries in Vivo, Using a Computerized Frame–by–Frame Analysis of Video Images," *Microvascular Research*, 27, pp. 1–13, 1984.

"EyeCom II Picture Digitizer and Display; Model 109PTS," *Spatial Data Systems, Inc.*, date unknown.

"EyeCom II Picture Digitizer and Display; Now with Model 808–19 Real Time Processor," *Spatial Data Systems, Inc.*, date unknown.

"EyeCom Image Scanner," *Spatial Data Systems, Inc.*, 1983.

Fagrell et al., "A Microscope–Television System for Studying Flow Velocity in Human Skin Capillaries," *American Journal of Physiology*, vol. 233, No. 2, pp. H318–H321, Aug. 1977.

Fagrell et al., "Relative Hematocrit in Human Skin Capillaries and Its Relation to Capilliary Blood Flow Velocity," *Microvascular Research*, 20, pp. 327–335, 1980.

Fenton et al., "Microcirculatory Model Relating Geometrical Variation to Changes in Pressure and Flow Rate," *Annals of Biomedical Engineering*, vol. 9, pp. 303–321, 1981.

Fesler et al., "A Microcomputerised Oxyhemoglobin Dissociation Curve Analyser for Clinical Use," *Computers in Cardiology*, pp. 379–382, Sep. 1979.

Foster, "The New Breed of Image Analyzers," date unknown.

Gaspar–Rosas et al., "Erythrocyte Aggregate Rheology by Transmitted and Reflected Light," *Biorheology*, 25, pp. 471–487, 1988.

Harms et al., "Untersuchungen der Abtastbedingungen bei Zellbildern mit einem Mikroskop–TV–System," *Microscopica Acta*, vol. 85, No. 1, pp. 69–82, Sep. 1981.

"How Hematrak Locates Cells," date unknown.

"Imageplus+; Image Analysis System," Dapple Systems, date unknown.

Kortright et al., "Human B Cell Enumeration in Peripheral Blood with B1 in Contrast to Cell Surface Immunoglobulin," date unknown.

Krause, "Red–Cell Abnormalities in the Blood Smear: Disease Correlations," *Laboratory Management*, vol. 23, No. 10, pp. 29–35, Oct. 1985.

Lipowsky et al., "Hematocrit Determination in Small Bore Tubes by Differential Spectrophotometry," *Microvascular Research*, 24, pp. 42–55, 1982.

"LOGE/SDS; Image Processing Executive System," pp. 1–5, date unknown.

Megla, "An Automatic White Blood Cell Analyzer," *SID Journal*, pp. 20–22, Sep.–Oct. 1974.

Mickols et al., "Visualization of Oriented Hemoglobin S in Individual Erythrocytes by Differential Extinction of Polarized Light," *Proceedings of the National Accademy of Science*, vol. 82, pp. 6527–6531, Oct. 1985.

Miller, "Design and Clinical Results of Hematrak: An Automated Differential Counter," *IEEE Transactions on Biomedical Engineering*, vol. BME–23, No. 5, pp. 400–405, Sep. 1976.

"Omnicon 5000: Image Analysis System," *Bausch & Lomb*, pp. 1–15, date unknown.

"Other EyeCom II Configurations Include:," *Spatial Data Systems, Inc.*, pp. 1–3, date unknown.

"Q10; A New Generation Low Cost Image Analysis System," *Cambridge Instruments*, date unknown.

"Rack–Mount Version of EyeCom Terminal; Models 109RM, 109KB, 108D," *Spatial Data Systems, Inc.*, date unknown.

Safranyos et al., "Hetergeneity of Capillary Diameters in Skeletal Muscle of the Frog," *Microvascular Research*, 26, pp. 151–156, 1983.

"The Search for Clinical Confidence," *Geometric Data*, date unknown.

Shimizu et al., *Structure of Ocular Vessels*, pp. 127, 128, 132, 134, 1978.

Sodickson et al., "Kromoscopic Analysis: A Possible Alternative to Spectroscopic Analysis for Noninvasive Measurement of Analytes in Vivo," *Clinical Chemistry*, vol. 40, No. 9, pp. 1838–1844, 1994.

Todd et al., *Clinical Diagnosis and Management by Laboratory Methods*; vol. I, W. B. Saunders Company, p. 872, 1979.

"The Yellow Iris: The Automated Urinalysis Workstation," *International Remote Imaging Systems*, 1983.

Yodh et al., "Spectroscopy and Imaging with Diffusing Light," *Physics Today*, pp. 34–40, Mar. 1995.

Bentley et al., "The Morphological Classification of Red Cells using an Image Analysing Computer," *British Journal of Haematology*, 1976, pp. 205–214.

Ellis et al., "Television–Computer Method for in Vivo Measurement of Capillary Diameter, Based on the Passage of Red Cells," *Microvascular Research*, 26, pp. 139–150, 1983.

Fishlock, "Magiscan Instrument in Clinical Trials," *Financial Times*, p. 8, Apr. 18, 1983.

Johnson, "Red Cell Separation in the Mesenteric Capillary Network," *American Journal of Physiology*, vol. 221, No. 1, pp. 99–104, Jul. 1971.

Demos S.G. et al., "Polarization Imaging and Characterization of Human Breast Tissues," *Advances In Optical Imaging and Photon Migration*, vol. 2, 1996, pp. 113–115.

Demos S.G. et al., "Temporal gating in highly scattering media by the degree of optical polarization", Reprinted from *Optic Letters*, vol. 2, No. 2, Jan. 15, 1996, pp. 161–163.

Demos S.G. et al., "Time Resolved Degree of Polarization for Human Breast Tissue," *Reprinted from Optics Communications 124* (1996), Mar. 15, 1996, pp. 439–442.

Ellsworth, Mary L. and Pittman, Ronald N., "Evaluation of photometric methods for quantifying convective mass transport in microvessels," *The American Physiological Society*, 1986, pp. H869–H879.

Kuo, Lih and Pittman, Ronald N., "Effect of hemodilution on oxygen transport in arteriolar networks of hamster striated muscle", *The American Physiological Society*, 1988, pp. H331–H339.

Kuo, Lih and Pittman, Ronald N., "Influence of hemoconcentration on arteriolar oxygen transport in hamster striated muscle," *The American Physiological Society*, 1990, pp. H1694–H1702.

Mott, Elizabeth, et al., Development of an Optical Triplicator for Intravital Video Microscopy of Oxygen Saturation, *IEEE Transactions on Biomedical Engineering*, vol. 43, No. 11, Nov., 1996, pp. 1116–1119.

Parthasarathi, Kaushik and Pittman, Roland N., "Measurements of Hemoglobin Concentration and Oxygen Saturation Profiles in Arterioles Using Intravital Videomicroscopy and Image Analysis," *Oxygen Transport to Tissue XVI*, 1994, pp. 249–260.

Pittman, Roland N., and Duling, Brian R., "A New Method for the Measurement of Percent Oxyhemoglobin," *Journal of Applied Physiology*, vol. 38, No. 2, Feb., 1975, pp. 315–320.

Pittman, Roland N., "In Vivo Photometric Analysis of Hemoglobin," *Annals of Biomedical Engineering*, vol. 14, 1986, 119–137.

Pittman, Roland N., and Duling, Brian R., "Measurement of percent oxyhemoglobin in the microvasculature," *Journal of Applied Physiology*, vol. 38, No. 2, Feb., 1975, pp. 321–327.

Twersky, Victor, "Absorption and Multiple Scattering by Biological Suspensions," *Journal of the Optical Society of America*, vol. 60, No. 8, Aug., 1970, pp. 1084–1093.

| N=70 | Coulter | Feasibility Model | Agree | Not Agree | False High | False Low |
|---|---|---|---|---|---|---|
| Anemia | 51 | 52 | 50 | 1 | 1 | 0 |
| Normal | 19 | 18 | 17 | 2 | 0 | 2 |
| Total | 70 | 70 | 67 | 3 | 1 | 2 |
| Average (r) | | | 0.903 | | | |
| Agreement (%) | | | 96% | | | |

FIG.8A

METHOD AND APPARATUS FOR REFLECTED IMAGING ANALYSIS

CROSS-REFERENCE TO RELATED APPLICATIONS

This application claims priority to: Appl. No. 60/005,836, filed Oct. 23, 1995; Appl. No. 60/016,040, filed Apr. 23, 1996; Appl. No. 60/016,036, filed Apr. 23, 1996; Appl. No. 60/016,037, filed Apr. 23, 1996; Appl. No.60/016,039, filed Apr. 23, 1996; and Appl. No. 60/020,685, filed Jun. 27, 1996; the disclosure of all of the foregoing applications is incorporated herein by reference as though set forth in full hereinafter.

BACKGROUND OF THE INVENTION

1. Field of the Invention

The present invention is related to reflected light analysis. More particularly, the present invention is related to the use of reflected spectral imaging to perform non-invasive analysis of a subject's vascular system. The present invention is also related to the use of cross-polarizers in reflected spectral imaging analysis.

2. Related Art

Widely accepted medical school doctrine teaches that the complete blood count including the white blood cell differential (CBC+Diff) is one of the best tests to assess a patient's overall health. With it, a physician can detect or diagnose anemia, infection, blood loss, acute and chronic diseases, allergies, and other conditions. CBC+Diff analyses provide comprehensive information on constituents in blood, including the number of red cells, the hematocrit, the hemoglobin concentration, and indices that portray the size, shape, and oxygen-carrying characteristics of the entire red blood cell (RBC) population. The CBC+Diff also includes the number and types of white blood cells and the number of platelets. The CBC+Diff is one of the most frequently requested diagnostic tests with about two billion done in the United States per year.

A conventional CBC+Diff test is done in an "invasive" manner in which a sample of venous blood is drawn from a patient through a needle, and submitted to a laboratory for analysis. For example, a phlebotomist (an individual specially trained in drawing blood) collects a sample of venous blood into a tube containing an anticoagulant to prevent the blood from clotting. The sample is then sent to a hematology laboratory to be processed, typically on automated, multi-parameter analytical instruments, such as those manufactured by Coulter Diagnostics of Miami, Fla. The CBC+Diff test results are returned to the requesting physician, typically on the next day.

In medical diagnosis it is often necessary to measure other types of blood components, such as non-cellular constituents present in the plasma component of blood. Such constituents can include, for example, blood gases and bilirubin. Bilirubin is a reddish to yellow pigment produced in the metabolic breakdown of hemoglobin and other proteins. Bilirubin is removed from the blood by the liver and is excreted from the body. However, the livers of newborn children, especially premature babies, cannot process bilirubin effectively.

The birth process often results in extensive bruising, resulting in blood escaping into the tissues where it is broken down metabolically. For this and other medical causes, bilirubin may accumulate in the blood stream. If bilirubin levels rise high enough, it begins to be deposited in other body tissues causing jaundice. Its first appearance is in the eye. At still higher levels, deposition begins in deeper tissues, including the brain, and can result in permanent brain damage.

The most common method for bilirubin analysis is through an in vitro process. In such an in vitro process, a blood sample is invasively drawn from the patient. The formed elements (red blood cells and other cells) are separated by centrifugation and the remaining fluid is reacted chemically and analyzed spectrophotometrically.

Invasive techniques, such as for conventional CBC+Diff tests and bilirubin analysis, pose particular problems for newborns because their circulatory system is not yet fully developed. Blood is typically drawn using a "heel stick" procedure wherein one or more punctures are made in the heel of the newborn, and blood is repeatedly squeezed out into a collecting tube. This procedure is traumatic even for an infant in good health. More importantly, this procedure poses the risk of having to do a blood transfusion because of the low total blood volume of the infant. The total blood volume of the newborn infant is 60–70 cc/kg body weight. Thus, the total blood volume of low birth weight infants (under 2500 grams) cared for in newborn intensive care units ranges from 45–175 cc. Because of their low blood volume and delay in production of red cells after birth, blood sampling from preterm infants and other sick infants frequently necessitates transfusions for these infants. Blood bank use for transfusion of infants in neonatal intensive care units is second only to the usage for cardiothoracic surgery in blood banking requirements. In addition to newborns, invasive techniques are also particularly stressful for, and/or difficult to carry out on, children, elderly patients, burn patients, and patients in special care units.

A hierarchical relationship exists between the laboratory findings and those obtained at the physical examination. The demarcation between the physical findings of the patient and the laboratory findings are, in general, the result of technical limitations. For instance, in the diagnosis of anemia (defined as low hemoglobin concentration), it is frequently necessary to quantify the hemoglobin concentration or the hematocrit in order to verify the observation of pallor. Pallor is the lack of the pink color of skin which frequently signals the absence or reduced concentration of the heavily red pigmented hemoglobin. However, there are some instances in which pallor may result from other causes, such as constriction of peripheral vessels, or being hidden by skin pigmentation. Because certain parts of the integument are less affected by these factors, clinicians have found that the pallor associated with anemia can more accurately be detected in the mucous membrane of the mouth, the conjunctivae, the lips, and the nail beds. A device which is able to rapidly and non-invasively quantitatively determine the hemoglobin concentration directly from an examination of one or more of the foregoing areas would eliminate the need to draw a venous blood sample to ascertain anemia. Such a device would also eliminate the delay in waiting for the laboratory results in the evaluation of the patient. Such a device also has the advantage of added patient comfort.

Soft tissue, such as mucosal membranes or unpigmented skin, do not absorb light in the visible and near-infrared, i.e., they do not absorb light in the spectral region where hemoglobin absorbs light. This allows the vascularization to be differentiated by spectral absorption from surrounding soft tissue background. However, the surface of soft tissue strongly reflects light and the soft tissue itself effectively scatters light after penetration of only 100 microns. Therefore, in vivo visualization of the circulation is difficult because of poor resolution, and generally impractical because of the complexities involved in compensating for multiple scattering and for specular reflection from the surface. Studies on the visualization of cells in the microcirculation consequently have been almost exclusively invasive, using a thin section (less than the distance for multiple scattering) of tissue containing the microcirculation, such as the mesentery, that can be observed by a microscope using light transmitted through the tissue section. Other studies have experimented with producing images of tissues from within the multiple scattering region by time gating (see, Yodh, A. and B. Chance, *Physics Today,* March, 1995, 34–40). However, the resolution of such images is limited because of the scattering of light, and the computations for the scattering factor are complex.

Spectrophotometry involves analysis based on the absorption or attenuation of electromagnetic radiation by matter at one or more wavelengths of light. The instruments used in this analysis are referred to as spectrophotometers. A simple spectrophotometer includes: source of radiation, such as, e.g., a light bulb; a means of spectral selection such as a monochromator containing a prism or grating or colored filter; and one or more detectors, such as, e.g., photocells, which measure the amount of light transmitted and/or reflected by the sample in the selected spectral region.

In opaque samples, such as solids or highly absorbing solutions, the radiation reflected from the surface of the sample may be measured and compared with the radiation reflected from a non-absorbing or white sample. If this reflectance intensity is plotted as a function of wavelength, it gives a reflectance spectrum. Reflectance spectra are commonly used in matching colors of dyed fabrics or painted surfaces. However, because of its limited range and inaccuracy, reflection spectrophotometry has been used primarily in qualitative rather than quantitative analysis. On the other hand, transmission spectrophotometry is conventionally used for quantitative analysis because Beer's law (inversely relating the logarithm of measured intensity linearly to concentration) can be used.

Reflective spectrophotometry is conventionally avoided for quantitative analysis because specularly reflected light from a surface limits the available contrast (black to white or signal to noise ratio), and, consequently, the measurement range and linearity. Because of surface effects, measurements are usually made at an angle to the surface. However, only for the special case of a Lambertian surface will the reflected intensity be independent of the angle of viewing. Light reflected from a Lambertian surface appears equally bright in all directions (cosine law). However, good Lambertian surfaces are difficult to obtain. Conventional reflection spectrophotometry presents an even more complicated relationship between reflected light intensity and concentration than exists for transmission spectrophotometry which follows Beer's law. Under the Kubelka-Munk theory applicable in reflection spectrophotometry, the intensity of reflected light can be related indirectly to concentration through the ratio of absorption to scattering.

Some imaging studies have been done in the reflected light of the microcirculation of the nail beds on patients with Raynauds, diabetes, and sickle cell disease. These studies were done to obtain experimental data regarding capillary density, capillary shape, and blood flow velocity, and were limited to gross physical measurements on capillaries. No spectral measurements, or individual cellular measurements, were made, and Doppler techniques were used to assess velocity. The non-invasive procedure employed in these studies could be applied to most patients, and in a comfortable manner.

One non-invasive device for in vivo analysis is disclosed in U.S. Pat. No. 4,998,533 to Winkelman. The Winkelman device uses image analysis and reflectance spectrophotometry to measure individual cell parameters such as cell size. Measurements are taken only within small vessels, such as capillaries where individual cells can be visualized. Because the Winkelman device takes measurements only in capillaries, measurements made by the Winkelman device will not accurately reflect measurements for larger vessels. This inaccuracy results from the constantly changing relationship of volume of cells to volume of blood in small capillaries resulting from the non-Newtonian viscosity characteristic of blood. Consequently, the Winkelman device is not capable of measuring the central or true hematocrit, or the total hemoglobin concentration, which depend upon the ratio of the volume of red blood cells to that of the whole blood in a large vessel such as a vein.

The Winkelman device measures the number of white blood cells relative to the number of red blood cells by counting individual cells as they flow through a microcapillary. The Winkelman device depends upon accumulating a statistically reliable number of white blood cells in order to estimate the concentration. However, blood flowing through a micro-capillary will contain approximately 1000 red cells for every white cell, making this an impractical method. The Winkelman device does not provide any means by which platelets can be visualized and counted. Further, the Winkelman device does not provide any means by which the capillary plasma can be visualized, or the constituents of the capillary plasma quantified. The Winkelman device also does not provide a means by which abnormal constituents of blood, such as tumor cells, can be detected.

Thus, there is a need in the art for a device that provides for complete non-invasive in vivo analysis of the vascular system. There is a need for a device that provides for high resolution visualization of: blood cell components (red blood cells, white blood cells, and platelets); blood rheology; the vessels in which blood travels; and vascularization throughout the vascular system. There is a further need for a non-invasive device that allows quantitative determinations to be made for blood cells, normal and abnormal contents of blood cells, as well as for normal and abnormal constituents of blood plasma.

SUMMARY OF THE INVENTION

The present invention is directed to a method and apparatus for analysis of blood by use of reflected spectral imaging analysis. In one embodiment, the apparatus can include a light source that illuminates blood to form a light path between the light source and the illuminated blood. A first polarizer is used to polarize light from the light source. Image capturing means is used to capture the reflected image reflected from the illuminated object at a depth less than a multiple scattering length. The reflected image travels along a reflected light path between the illuminated blood and the image capturing means. A second polarizer is placed in the reflected light path between the illuminated blood and the image capturing means. The second polarizer has a plane of polarization that is 90° relative to the plane of polarization of the first polarizer. In one aspect of the present invention, the light source comprises the first polarizer, so that the second polarizer has a plane of polarization 90° relative to the plane of polarization of the polarized light produced by the light source.

In a further aspect of the present invention, the apparatus includes image separating means that are placed in the reflected light path between the second polarizer and the image capturing means. The image separating means separates the reflected image into multiple image portions. Additional image capturing means can be used to capture the multiple portions of the reflected image. Spectral selection means can be placed in the reflected light path between the image separating means and the image capturing means.

In a further aspect of the present invention, a method for analysis of blood is provided. The method includes the following steps: (1) imaging blood to produce a raw reflected image reflected from a depth less than a multiple scattering length; (2) applying a correction to the raw reflected image to form a corrected reflected image; (3) segmenting a scene from the corrected reflected image to form an analysis image; and (4) analyzing the analysis image for a characteristic of the blood.

In a further aspect of the method of the present invention, the step of applying a correction to the raw reflected image can be carried out using the following steps: (a) applying a first wavelength filter to the raw reflected image to form a first filtered image; (b) applying a second wavelength filter to the raw reflected image to form a second filtered image; and (c) taking the negative logarithm of the quotient obtained by dividing the first filtered image by the second filtered image to form the corrected reflected image. Alternatively, the correction may be performed by taking the difference of the logarithm of the first and second filtered images.

In another aspect of the method of the present invention, a step of segmenting a scene from the corrected reflected image to form an analysis image includes applying one or more criterion to the corrected reflected image. These criteria can include an optical intensity criterion, a size criterion, a shape criterion, or other spatial filtering techniques.

The method of the present invention can be used to determine various characteristics of blood. Such characteristics can include the hemoglobin concentration per unit volume of blood, the number of white blood cells per unit volume of blood, a mean cell volume, a mean cell hemoglobin concentration, the number of platelets per unit volume of blood, and the hematocrit.

In still a further aspect of the method of the present invention, the blood can be illuminated with light polarized by a first polarizer. The reflected image can be passed through a second polarizer or analyzer having a plane of polarization 90° relative to a plane of polarization of the first polarizer to produce the raw reflected image.

In further aspects of the present invention, the method is used to perform in vivo analysis of blood in large vessels, and in vivo analysis of blood in small vessels to determine blood parameters such as concentrations and blood cell counts. The method of the present invention can also be used to conduct non-invasive in vivo analysis of non-cellular characteristics of capillary plasma.

In yet a further embodiment of the present invention, an apparatus is provided for detecting optical characteristics of an object. The apparatus includes a light source for illuminating the object, and detecting means for detecting reflected light that is reflected from the illuminated object. A first polarizer is used to polarize light from the light source. A second polarizer is placed in a reflected light path between the object and the detecting means. The plane of polarization of the second polarizer is 90° relative to a plane of polarization of the first polarizer. In further aspects of the present invention, the light source is monochromatic, polarized, or monochromatic and polarized.

FEATURES AND ADVANTAGES

It is a feature of the present invention that it provides for non-invasive in vivo analysis of the vascular system. It is a further feature of the present invention that quantitative analyses of formed blood cell components (red blood cells, white blood cells, and platelets) can be done. It is also a further feature of the present invention that quantitative analyses of non-formed blood components, such as capillary plasma, can also be done.

It is yet a further feature of the present invention that per unit volume or concentration measurements, such as hemoglobin, hematocrit, and blood cell counts, can be made through the use of reflected spectral images of the vascular system.

It is yet a further feature of the present invention that blood cells, blood vessels, and capillary plasma can be visualized and segmented into an analysis image.

A still further feature of the present invention is that it can be used to determine characteristics such as the hemoglobin concentration per unit volume of blood, the number of white blood cells per unit volume of blood, the mean cell volume, the mean cell hemoglobin concentration, the number of platelets per unit volume of blood, and the hematocrit through the use of reflected spectral imaging.

An advantage of the present invention is that it provides a means for the rapid, non-invasive measurement of clinically significant parameters of the CBC+Diff test. It advantageously provides immediate results. As such, it can be used for point-of-care testing and diagnosis.

A further advantage of the present invention is that it eliminates the invasive technique of drawing blood. This eliminates the pain and difficulty of drawing blood from newborns, children, elderly patients, burn patients, and patients in special care units. The present invention is also advantageous in that it obviates the risk of exposure to AIDS, hepatitis, and other blood-borne diseases.

A still further advantage of the present invention is that it provides for overall cost savings by eliminating sample transportation, handling, and disposal costs associated with conventional invasive techniques.

A still further advantage of the present invention is that it provides for substantially improved range and accuracy for reflection spectrophotometry. The present invention is also advantageous in that it permits use of a simple relationship between concentration and intensity.

A still further advantage of the present invention is that it provides for improved visualization of reflected images of any object, and for quantitative and qualitative analyses of these reflected images.

BRIEF DESCRIPTION OF THE DRAWINGS

The present invention is described with reference to the accompanying drawings. In the drawings, like reference numbers indicate identical or functionally similar elements. Additionally, the left-most digit(s) of a reference number identifies the drawing in which the reference number first appears.

FIG. 8A shows a chart summarizing the agreement between laboratory results on a Coulter device and the feasibility model;

DETAILED DESCRIPTION OF THE EMBODIMENTS

1. Overview

Figure 1:
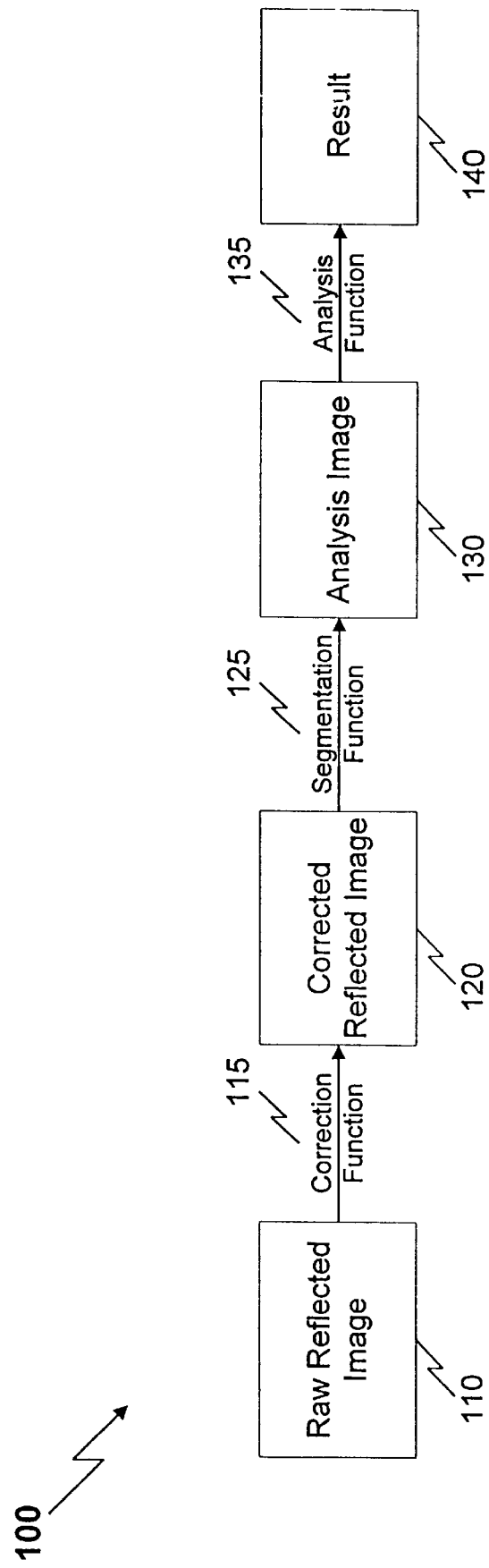
FIG. 1 shows a block diagram of one embodiment of a method of the present invention.

The present invention is directed to a method and apparatus for analysis, particularly non-invasive, in vivo analysis of a subject's vascular system. The method is carried out by imaging a portion of the subject's vascular system. The tissue covering the imaged portion must be traversed by light without multiple scattering to obtain a reflected image. In order to form an image, two criteria must be met. First, there must be image contrast resulting from a difference in the optical properties, such as absorption, index of refraction, or scattering characteristics, between the subject to be imaged and its surround or background. Second, the light that is collected from the subject must reach an image capturing means without substantial scattering, i.e., the reflected image must be captured from a depth that is less than the multiple scattering length. As used herein, "image" refers to any image that satisfies the foregoing two criteria. As used herein, "reflected image" refers to the image of a subject in reflected light. The resolution required for capturing the image is dictated by the spatial homogeneity of the imaged portion. For example, a reflected image of individual cells requires high resolution. A reflected image of large vessels can be done with low resolution. A reflected image suitable for making a determination based on pallor requires very low resolution.

The tissue covering the imaged portion is thus preferably transparent to light, and relatively thin, such as the mucosal membrane on the inside of the lip of a human subject. As used herein, "light" refers generally to electromagnetic radiation of any wavelength, including the infrared, visible, and ultraviolet portions of the spectrum. A particularly preferred portion of the spectrum is that portion where there is relative transparency of tissue, such as in the visible and near-infrared wavelengths. It is to be understood that for the present invention, light can be coherent light or incoherent light, and illumination may be steady or in pulses of light.

The reflected image is corrected to form a corrected reflected image. The correction to the reflected image is done, for example, to isolate particular wavelengths of interest, or to extract a moving portion of the image from a stationary portion of the image. A scene is segmented from the corrected reflected image to form an analysis image. The analysis image is then analyzed for the desired characteristic of the subject's vascular system.

The method of the present invention can be used for analysis in large vessels, small vessels, and in capillary plasma. As used herein, "large vessel" refers to a vessel in the vascular system of sufficient size so that a plurality of red blood cells flow side-by-side through it. "Small vessel" refers to a vessel in the vascular system of a size so that red blood cells flow substantially "single file" through it. As explained in more detail below, the present invention uses reflectance, not transmission, for the images that are analyzed. That is, the image is made by "looking at" the vascular system, rather than by "looking through" the vascular system. Per unit volume or concentration measurements can be made directly from the images.

By using the method of the present invention to provide a reflected spectral image of large vessels, the hemoglobin (Hb), hematocrit (Hct), and white blood cell count (WBC) parameters can be directly determined. By using the method of the present invention to provide a reflected spectral image of small vessels, mean cell volume (MCV), mean cell hemoglobin concentration (MCHC), and platelet count (Plt) can be directly determined.

To implement the method of the present invention, a light source is used to illuminate the portion of the subject's vascular system to be imaged. The reflected light is captured by an image capturing means. By image capturing means is meant a device capable of capturing an image as defined herein. Suitable image capturing means include, but are not limited to, a camera, a film medium, a photocell, a photodiode, or a charge coupled device camera. An image correcting and analyzing means, such as a computer, is coupled to the image capturing means for carrying out image correction, scene segmentation, and blood characteristic analysis.

The image correction can be a poly-chromatic correction using a primary wavelength and one or more secondary wavelengths. For example, to implement a bi-chromatic correction, the reflected image is separated into two portions. This can be implemented using an image separating means, such as a dichroic mirror. In this manner, one image capturing means is used to capture the portion of the image transmitted through the dichroic mirror, and one image capturing means is used to capture the portion of the image reflected by the dichroic mirror. Image correcting and analyzing means coupled to both image capturing means carries out a correction of one image portion relative to the other image portion to provide the corrected image.

Cross-polarizers are preferably used in implementing the present invention. One polarizer is placed in the light path between the light source and the illuminated portion of the subject's vascular system. A second polarizer or "analyzer" is placed in the reflected light path between the illuminated portion and the image capturing means. The second polarizer has a plane of polarization 90° relative to the plane of polarization of the first polarizer. The cross-polarizer configuration improves the collection of light that has interacted with the illuminated portion of the subject's vascular system and tissue by eliminating light that has simply been reflected and has not fully interacted with the illuminated portion. Therefore, light with no information regarding the illuminated subject is eliminated. In this manner, the image contrast for the reflected image is vastly increased, thereby improving visualization in the illuminated portion.

The cross-polarization technique of the present invention can be used in any application that requires optically measuring or visually observing reflecting characteristics of an object. The cross-polarizers of the present invention can be used to increase the working range, and permit the use of a simple relationship between intensity and concentration for analytical instruments that detect differences in reflected intensity. The cross-polarization technique of the present invention is applicable in such fields as dye lot control, fabric color control, strip testing using paper, film, or latex, borescopic and orthoscopic applications.

2. Methods of the Present Invention

In order to see into an object using reflected light, there must be light coming back from the object which has interacted with the object below the surface. In using a reflected image, two properties must be considered: (1) the absorption of light within the object; and (2) the scattering of light within the object. A reflected image is a three dimensional image that has an area and a depth of penetration. The depth of penetration or path length for the light is controlled by three parameters: (1) the wavelength of light; (2) the size of the particles with which the light interacts; and (3) the index of refraction. If the wavelength of light, the particle size, and the index of refraction are constant, then the depth of penetration is constant. Therefore, a measurement made per unit area in such a reflected image is proportional to a measurement per unit volume because the depth of penetration is constant. An area measurement is a volume measurement with a constant third dimension (depth).

With reference now to FIG. 1, a block diagram 100 of one embodiment of a method of the present invention for reflected spectral imaging analysis is shown. Block diagram 100 illustrates a process used to convert a raw reflected image 110 into a result 140. By raw reflected image is meant the reflected image prior to application of a correction function 115.

Correction function 115 is applied to raw reflected image 110 to produce a corrected reflected image 120. Correction function 115 normalizes raw reflected image 110 with respect to the image background. In one embodiment, correction function 115 is implemented by way of a bi-chromatic correction. For a bi-chromatic correction, two wavelengths, $\lambda_1$ and $\lambda_2$, are selected. By subtracting the $\lambda_2$ image from the $\lambda_1$ image, all parameters that affect both $\lambda_1$ and $\lambda_2$ in the same manner cancel out, and are thus eliminated, in the resulting $(\lambda_1-\lambda_2)$ image. The resulting $(\lambda_1-\lambda_2)$ image incorporates the effect of only those parameters that affect $\lambda_1$ and $\lambda_2$ differently.

In another embodiment, correction function 115 is implemented by way of a velocity or speed correction. For a velocity correction, corrected reflected image 120 is formed by taking the difference between raw reflected image 110 at a time $t_0$ and at a time $t_1$. For this purpose, means must be provided to pulse the light, and/or shutter an image capturing means such as a camera, so that two different images in time are obtained. A velocity correction allows a moving portion of raw reflected image 110 to be extracted from a stationary portion of raw reflected image 110. In this manner, corrected reflected image 120 is formed to contain either the moving portion or the stationary portion of raw reflected image 110.

A segmentation function 125 is applied to corrected reflected image 120 to form an analysis image 130. Segmentation function 125 segments or separates a scene of interest from corrected reflected image 120 to form analysis image 130. An analysis function 135 is applied to analysis image 130 to produce result 140. The scene of interest segmented by segmentation function 125 can depend upon the type of analysis performed by analysis function 135. In this manner, corrected reflected image 120 may contain many scenes of interests that are segmented differently by various segmentation functions.

Figure 2:
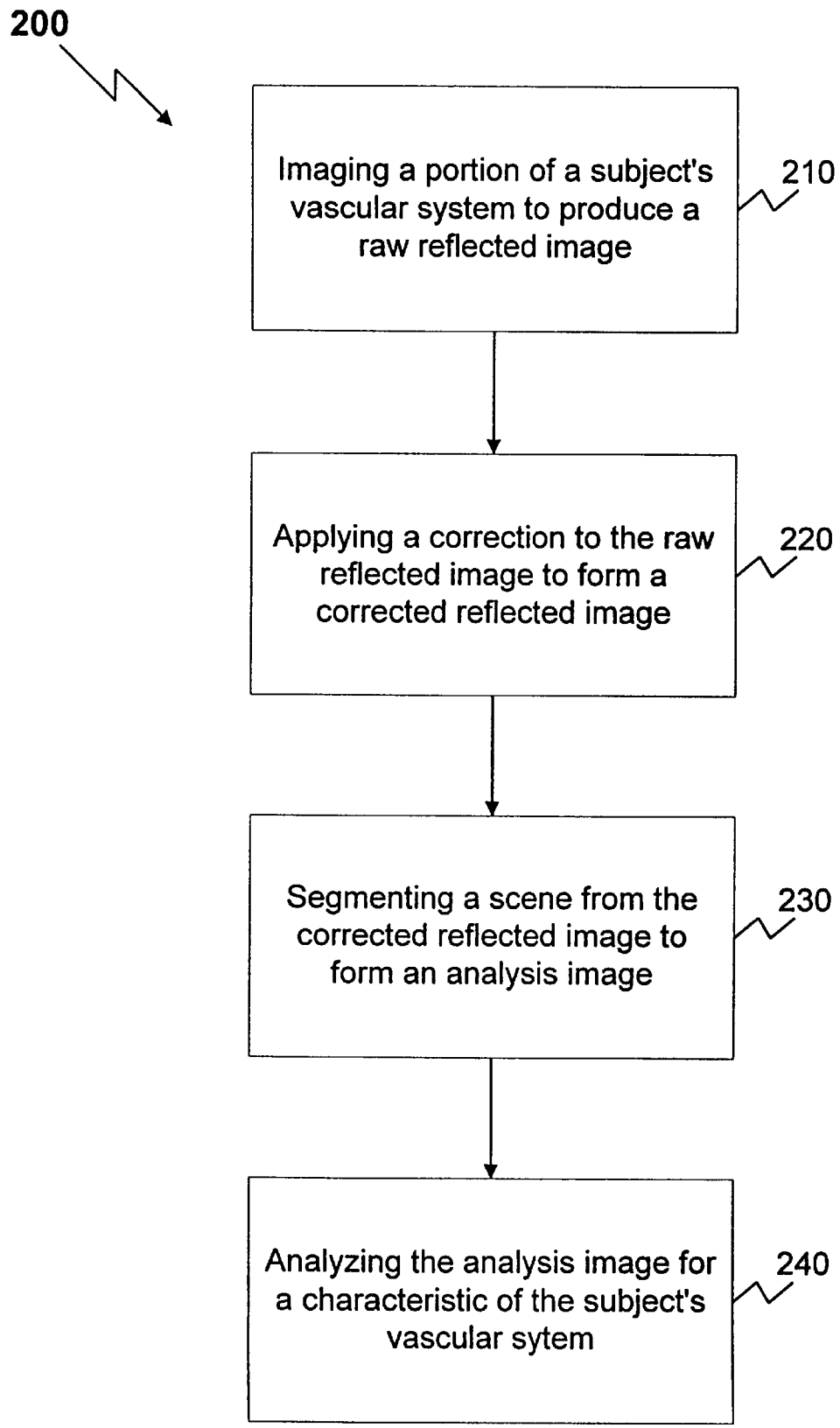
FIG. 2 shows a block diagram of an embodiment of the present invention for imaging a subject's vascular system.

With reference now to FIG. 2, a block diagram 200 of a method of the present invention for reflected spectral imaging of a subject's vascular system is shown. In a step 210, a portion of a subject's vascular system is imaged to produce raw reflected image 110 (see FIG. 1). The tissue covering the imaged portion must be traversed by light to obtain a reflected image without multiple scattering. The reflected image is essentially from a single scattering of the reflected light. The tissue covering the imaged portion should be transparent to light. Particularly suitable tissues are the mucosal membranes found in a variety of places in a human subject, such as the nose, mouth, conjunctivae, rectum, and vagina. Alternatively, for a premature baby, the skin itself is suitably transparent to light. The inside of the lip of a human subject provides a suitable area for imaging a portion of a human subject's vascular system. In this manner, light from a light source penetrates the mucosal membrane to produce a raw reflected image of the microvascular system. The microvascular system contains both large vessels and small vessels. As such, it is representative of vessels throughout the vascular system. The raw reflected image of the microvascular system from the inside of the lip is from a depth of approximately 50 $\mu$, to 500 $\mu$. Alternatively, the microvascular system could be imaged through skin tissue, such as on the finger or the toe of a human subject.

In a step 220, a correction is applied to raw reflected image 110 to form corrected reflected image 120. For example, correction function 115 can be applied to raw reflected image 110 to normalize it with respect to the background. A poly-chromatic correction, such as a bi-chromatic correction, can be used to eliminate the effects of light intensity, depth, and angle of light from the corrected reflected image. A poly-chromatic correction can eliminate the effect of pigmentation of the tissue through which the light travels to illuminate the imaged portion of the vascular system. The tissue pigmentation will affect some wavelengths of light in the same manner, so that the tissue pigmentation effect is canceled out through use of a poly-chromatic correction. A velocity correction could be applied to extract moving cells from a stationary background. The velocity correction could be used alone, or in conjunction with, a poly-chromatic correction.

In a step 230, a scene is segmented from corrected reflected image 120 to form analysis image 130. The analysis image is formed so that it contains the subject matter needed for analyzing a characteristic of the subject's vascular system. For example, the characteristic to be analyzed may be one for which large vessels should be analyzed, such as hemoglobin concentration per unit volume of blood, or the number of white blood cells per unit volume of blood. For these characteristics, analysis image 130 is formed so that it contains large vessels. As another example, the characteristic to be analyzed may be one for which small vessels should be analyzed, such as the number of platelets per unit volume of blood, or the concentration per unit volume of blood of components in capillary plasma, such as bilirubin. For these characteristics, analysis image 130 is formed so that it contains small vessels. In a step 240, analysis image 130 is analyzed using analysis function 135 for a characteristic of the subject's vascular system.

In an alternate embodiment, the scene can be segmented from the raw reflected image, and the scene corrected to form the analysis image. The method of the present invention can also be carried out without applying a correction function, so that the analysis image is formed from the raw reflected image.

Figure 3:
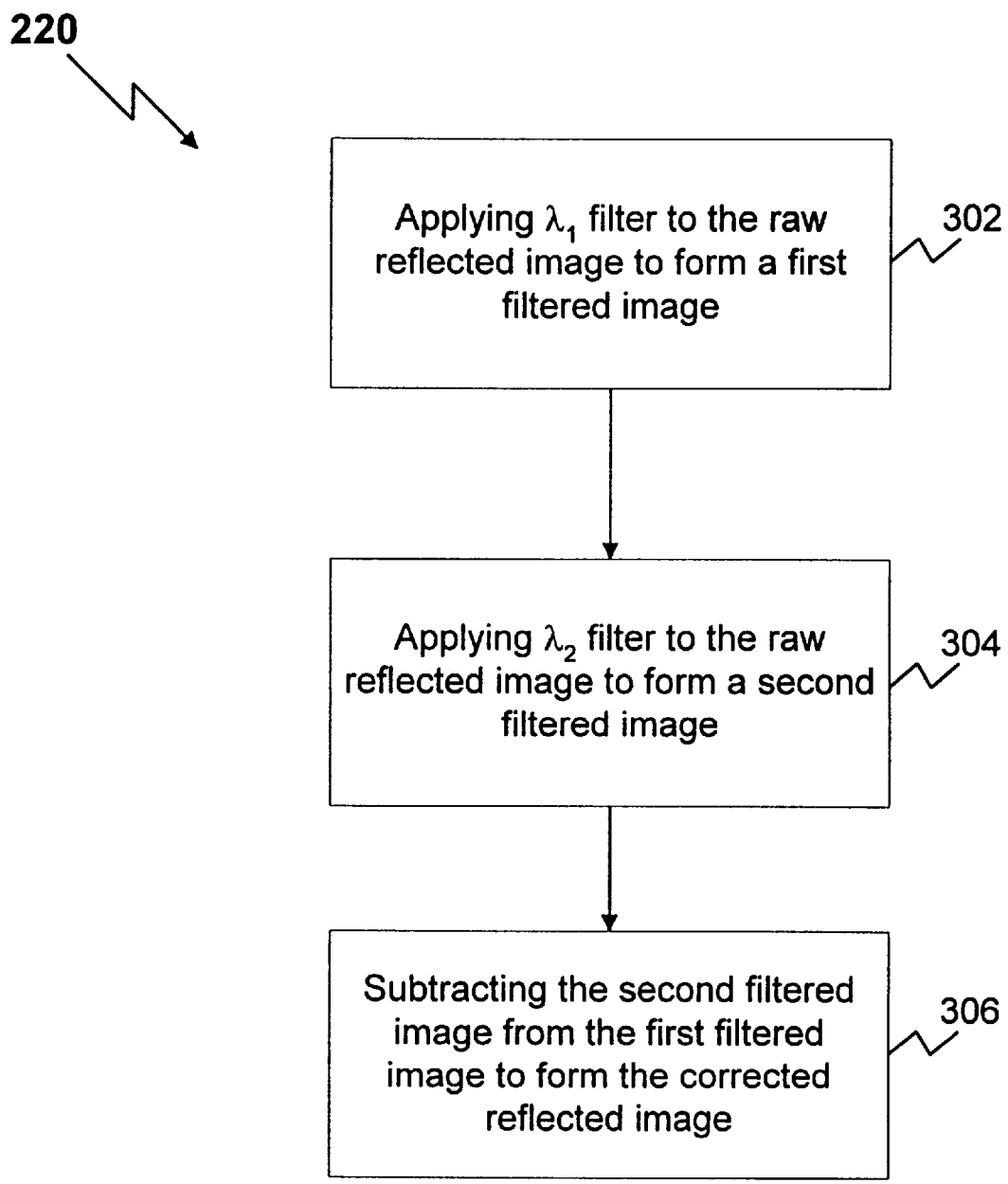
FIG. 3 shows a block diagram illustrating step 220 shown in FIG. 2.

FIG. 3 shows a block diagram illustrating one embodiment of step 220 shown in FIG. 2 for applying a correction to raw reflected image 110 to form corrected reflected image 120. In a step 302, a first wavelength filter ($\lambda_1$ filter) is applied to raw reflected image 110 to form a first filtered image. In a step 304, a second wavelength filter ($\lambda_2$ filter) is applied to raw reflected image 110 to form a second filtered image. In a similar manner, additional wavelength filters ($\lambda_3$, $\lambda_4$, $\lambda_5$, etc.) can be used to form additional filtered images.

In a step 306, the second filtered image is subtracted from the first filtered image to form corrected reflected image 120. By using the bi-chromatic correction of steps 302–306, those parameters that affect both $\lambda_1$ and $\lambda_2$ in the same manner have been eliminated from or canceled out of raw reflected image 110. The eliminated parameters include variations of light intensity, depth of penetration, angle of light, and pigmentation of tissue covering the imaged portion of the subject's vascular system. The corrected reflected image, ($\lambda_1$–$\lambda_2$) image, includes those items that are differentially affected by the two wavelengths. For raw reflected image 110, the light intensity, the depth of penetration of the light, and the angle of the light are all parameters that affect $\lambda_1$ and $\lambda_2$ in the same manner. Therefore, a bi-chromatic correction eliminates from raw reflected image 110 the effects of light intensity variation, depth of penetration of the light, and angle of the light to produce corrected reflected image 120.

Step 306 is preferably carried out in a manner that follows Beer's Law so that the logarithm of the reflected intensity of corrected image 120 is inversely proportional to concentration of a component, such as hemoglobin, within the corrected reflected image. Under Beer's law, the negative logarithm of measured reflected light intensity is linearly related to concentration. In one embodiment, step 306 is carried out so that the logarithm of the second filtered image is subtracted from the logarithm of the first filtered image to form corrected reflected image 120. In this manner, the logarithm of the reflected intensity of the corrected reflected image is proportional to concentration within the corrected reflected image. In an alternate embodiment, step 306 is carried out so that corrected reflected image 120 is formed by taking the negative logarithm of the quotient obtained by dividing the first filtered image by the second filtered image. In this manner as well, the logarithm of the reflected intensity of the corrected reflected image is proportional to concentration within the corrected reflected image.

By properly selecting $\lambda_1$ and $\lambda_2$, it is possible to normalize corrected reflected image 120 so that all that remains within the image is something that is proportional to hemoglobin concentration. To do so, one wavelength, such as $\lambda_1$, should be an absorbing wavelength for hemoglobin. Blood in the vascular system of a human subject is made up of arterial blood and venous blood. Arterial blood is that blood having hemoglobin rich in oxygen (oxy-hemoglobin) to be carried from the lungs to other parts of the body. Venous blood is that blood having hemoglobin poor in oxygen (deoxy-hemoglobin) to be carried from other parts of the body to the lungs to be replenished with oxygen. Arterial and venous blood differ in color. This color difference can be used to determine the degree of oxygen ($O_2$) saturation. The color signature of oxy-hemoglobin and deoxy-hemoglobin can be used to detect these hemoglobin complexes. Other hemoglobin complexes, such as carboxy-hemoglobin (carbon monoxide poisoning) or glycosolated hemoglobin (glucose hemoglobin complex monitored in diabetics) have spectral signatures allowing their measurement.

There are only certain wavelengths which are absorbed equally by both arterial blood and by venous blood. A wavelength which is absorbed equally by both arterial and venous blood is called an isobestic point. One such isobestic point for hemoglobin is located at 546 nm. In a preferred embodiment, $\lambda_1$ is selected so that it is located near the center of an absorption band for hemoglobin, and so that it is located near or at an isobestic point. A suitable $\lambda_1$ is 550 nm. In this manner, the hemoglobin concentration can be determined from reflected spectral imaging of a large vessel, irrespective of whether the large vessel is an artery carrying arterial blood or a vein carrying venous blood.

The other wavelength referred to as a "blank", such as $\lambda_2$, should be a non-absorbing wavelength for hemoglobin. $\lambda_2$ should be selected so that it is sufficiently close to $\lambda_1$ so that parameters such as light intensity, depth of penetration, angle of light, and tissue pigmentation have the same effect on both $\lambda_2$ and $\lambda_1$. $\lambda_2$ should be selected so that it is sufficiently far from $\lambda_1$ so that sufficient signal is obtained for the ($\lambda_1$–$\lambda_2$) image. The spectral spread between $\lambda_1$ and $\lambda_2$ should be selected to provide sufficient signal without introducing the effect of the other parameters listed above. It would be readily apparent to one of skill in the relevant arts how to select an appropriate spectral spread. An appropriate spectral spread for hemoglobin measurement is a first wavelength of 550 nm (absorbing wavelength) and a second wavelength of 650 nm (non-absorbing wavelength). With such a spectral spread, the difference in intensity of reflected light is a function of the concentration of hemoglobin.

Figure 4:
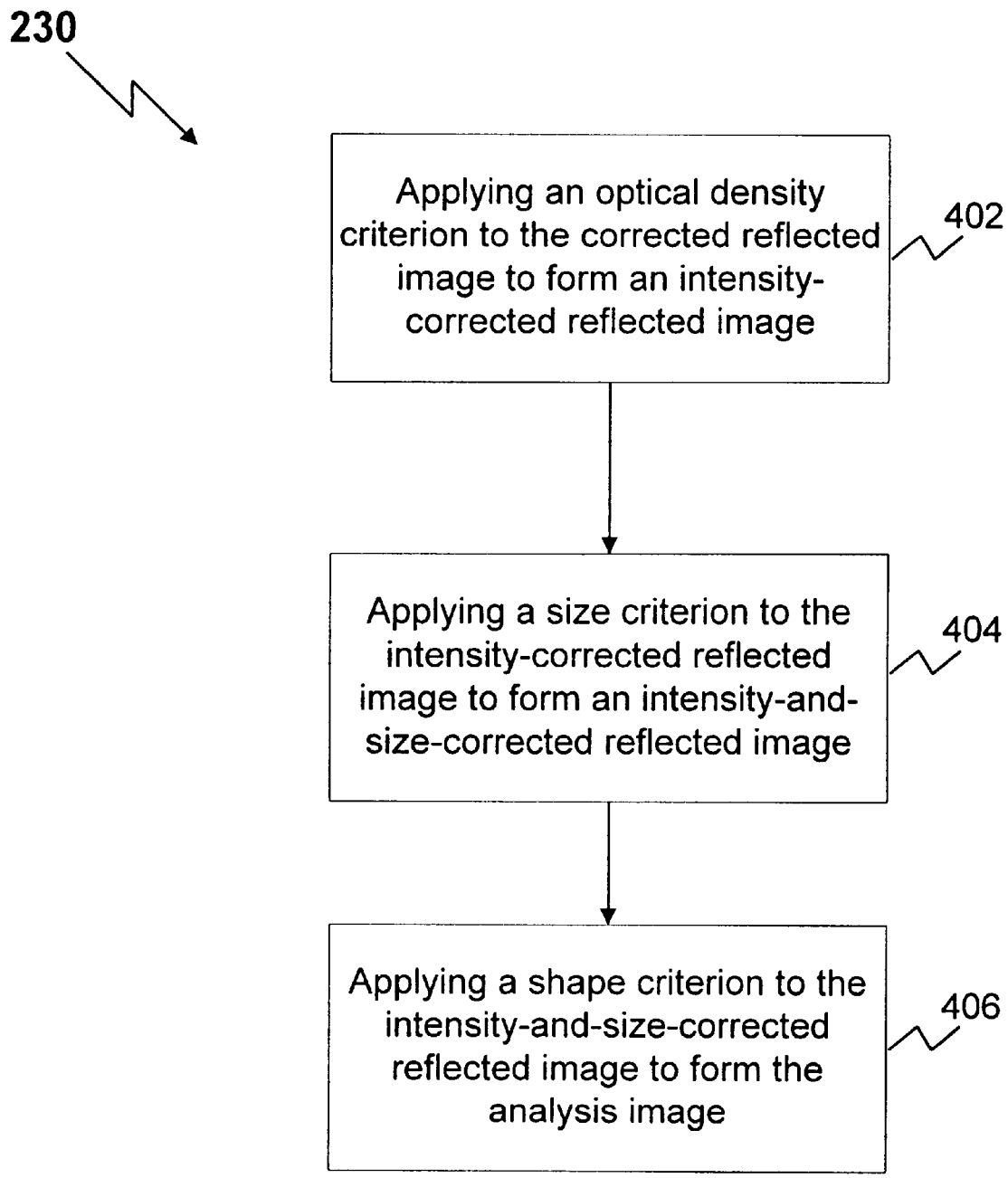
FIG. 4 shows a block diagram illustrating step 230 shown in FIG. 2.

FIG. 4 shows a block diagram illustrating one embodiment of step 230 shown in FIG. 2 for segmenting a scene from corrected reflected image 120 to form analysis image 130. In a step 402, an optical intensity criterion is applied to corrected reflected image 120 to form an intensity-corrected reflected image. For example, the optical intensity criterion can operate to delete all portions of the corrected reflected image that have an optical intensity below a certain threshold. Alternatively, the optical intensity criterion can operate to delete all portions of the corrected reflected image that have an optical intensity above a certain threshold. As yet another alternative, the optical intensity criterion can operate to retain only those portions of the corrected reflected image that have an optical intensity within a predetermined range.

In a step 404, a size criterion is applied to the intensity-corrected reflected image to form an intensity-and-size corrected reflected image. For example, the size criterion can operate to delete all portions of the intensity-corrected reflected image that are below a size threshold. Alternatively, the size criterion can operate to delete all portions of the intensity-corrected reflected image that are above a size threshold. As yet another alternative, the size criterion can operate to retain only those portions of the intensity-corrected reflected image that have a size within a predetermined range.

In a step 406, a shape criterion is applied to the intensity-and-size corrected reflected image to form analysis image 130. For example, the shape criterion can operate to retain only those portions of the intensity-and-size corrected reflected image that have a shape defined by a predetermined distance from an axis. Alternatively, the shape criterion can operate to retain only those portions of the intensity-and-size corrected reflected image that have a shape characteristic as defined by a smoothly shaped boundary. For example, the curvature of the boundary can be integrated to determine how the points of curvature are changing. Using a smoothly shaped boundary as a shape characteristic, a perfect circle would have a shape characteristic one (1). If the shape of the item in the image was not a perfect circle, its shape characteristic would be a value less than one. The smaller the value of the shape characteristic, the less smooth is the boundary of the item in the image. As an example, an item in the image shaped as an ellipse would have a shape characteristic approximately equal to 0.8. As another example, an item in the image having an elongated and thin shape would have a shape characteristic approximately equal to 0.1. The shape criterion can operate to retain only those portions of the intensity-and-size corrected reflected image that have a shape characteristic within a predetermined range. Alternatively, the shape criterion can operate to delete those portions of the intensity-and-size corrected reflected image that have a shape characteristic within a predetermined range.

Steps 402–406 represent one embodiment for segmenting a scene from corrected reflected image 120 to form analysis image 130. As such, steps 402–406 represent one embodiment of segmentation function 125. It is to be understood that the present invention is not limited to this embodiment. For example, a size criterion could be applied directly to corrected reflected image 120. A shape criterion could also be applied directly to corrected reflected image 120. As yet another example, the optical intensity criterion, size criterion, and shape criterion could be applied sequentially in a different order. Other suitable criteria could also be used to segment a scene from corrected reflected image 120, and the present invention is not limited to the use of optical intensity, size, and shape criteria. For example, motion can be used as a criterion to segment a scene from corrected reflected image 120. Motion can be used to discriminate between moving portions of the image, such as blood cells, from non-moving or slower-moving portions of the image, such as tissue. Additionally, other image contrast enhancement and scene segmentation techniques known to one of skill in the relevant arts could be used, such as for example, spatial frequency, optical flow, variance operators, and intensity histograms.

Figure 5:
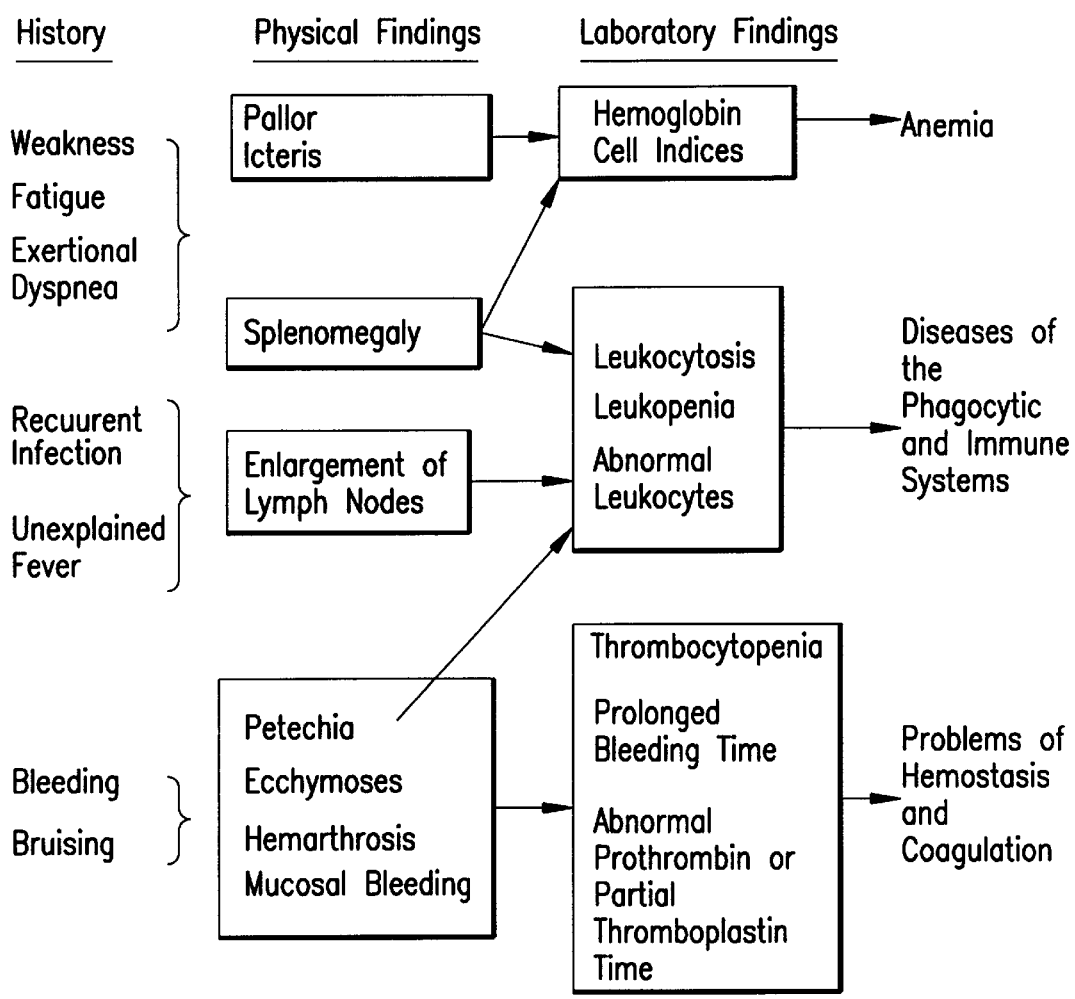
FIG. 5 shows a chart entitled Approach to Hematologic Disorders.

The method illustrated in FIGS. 1–4 can be used to carry out non-invasive in vivo analysis of blood parameters for the purpose of diagnosis or monitoring. FIG. 5, adapted from Wintrobe's Clinical Hematology, Ninth Edition, illustrates a graphical relationship between the three elements of the diagnosis of disorders of the blood: (1) history; (2) physical findings; and (3) laboratory findings. It is implicit in FIG. 5 that a hierarchical relationship exists between the laboratory findings and the physical findings obtained at a physical examination (P.E.). By rapidly and non-invasively determining the hemoglobin concentration and the mean cell volume along with the physical examination, the need to draw a venous blood sample is eliminated, along with the delay in waiting for the laboratory results in the evaluation of a patient.

In a similar manner, a rapid and non-invasive determination of the white blood cell count could aid in the diagnosis of infection and/or inflammation. The patient with fever could be examined to determine whether or not the concentration of white blood cells was elevated or decreased from normal.

Blood is made up of plasma and formed elements, and it flows throughout the vascular system through small vessels and large vessels as defined above. The formed elements of blood include red blood cells, white blood cells, and platelets. As used herein, "blood cells" refers to the formed elements of blood, and includes red blood cells, white blood cells, and platelets. The concentration of cells per unit volume of blood is a constant for large vessels and is a reliable predictor of the concentration in even larger vessels throughout the vascular system, such as vessels large enough for insertion of a needle for drawing blood. In contrast, a per unit volume (concentration) measurement made in a small vessel where red blood cells flow substantially single file is not a reliable predictor of the concentration measurement in larger vessels from which blood may drawn by insertion of a needle. The relationship between the concentration of cells and blood volume is constantly changing in a small vessel, and, as such, cannot be used as a reliable predictor of cell concentration in larger vessels. This effect is so variable between different individuals, and between different sites within one individual, that even averaging does not provide a reliable predictor for larger vessels.

A complete blood count (CBC) without white blood cell differential measures eight parameters: (1) hemoglobin (Hb); (2) hematocrit (Hct); (3) red blood cell count (RBC); (4) mean cell volume (MCV); (5) mean cell hemoglobin (MCH); (6) mean cell hemoglobin concentration (MCHC); (7) white blood cell count (WBC); and (8) platelet count (Plt). The first six parameters are referred to herein as RBC parameters. Concentration measurements (measurements per unit volume of blood) are necessary for producing values for Hb, Hct, RBC, WBC, and Plt. Hb is the hemoglobin concentration per unit volume of blood. Hct is the volume of cells per unit volume of blood. Hct can be expressed as a percentage (cell volume÷volume of blood)×100%

RBC is the number of red blood cells per unit volume of blood. WBC is the number of white blood cells per unit volume of blood. Plt is the number of platelets per unit volume of blood.

Red cell indices (MCV, MCH, and MCHC) are cellular parameters that depict the volume, hemoglobin content, and hemoglobin concentration, respectively, of the average red cell. The red cell indices may be determined by making measurements on individual cells, and averaging the individual cell measurements. Red cells do not change volume or lose hemoglobin as they move through the vascular system. Therefore, red cell indices are constant throughout the circulation, and can be reliably measured in small vessels. The three red cell indices are related by the equation

*MCHC=MCH÷MCV*

Thus, only two red cell indices are independent variables.

To determine values for the six RBC parameters listed above, the following two criteria must be met. First, three of the parameters must be independently measured or determined. That is, three of the parameters must be measured or determined without reference to any of the other of the six parameters. Second, at least one of the three independently measured or determined parameters must be a concentration parameter (per unit volume of blood). Therefore, values for the six key parameters can be determined by making three independent measurements, at least one of which is a concentration measurement which cannot be made in a small vessel.

In one embodiment of the present invention, Hb and Hct are directly measured by reflected spectral imaging of large vessels, and MCV is directly measured by reflected spectral imaging of small vessels. In this manner, three parameters are independently measured, and two of the parameters (Hb and Hct) are concentration parameters measured per unit volume of blood. In such an embodiment, the six RBC parameters listed above can be determined in the following manner.

| | |
|---|---|
| Hb | Directly measured |
| Hct | Directly measured |
| RBC | Hct ÷ MCV |
| MCV | Directly measured |
| MCH | MCV × (Hb ÷ Hct) |
| MCHC | Hb ÷ Hct |

In an alternate embodiment of the present invention, Hb is directly measured by reflected spectral imaging of large vessels, and MCV and MCHC are directly measured by reflected spectral imaging of small vessels. In this manner, three parameters are independently measured, and one of the parameters (Hb) is a concentration parameter measured per unit volume of blood. In such an alternate embodiment, the six RBC parameters listed above can be determined in the following manner.

| | |
|---|---|
| Hb | Directly measured |
| Hct | Hb ÷ MCHC |
| RBC | Hb ÷ (MCV × MCHC) |
| MCV | Directly measured |
| MCH | MCV × MCHC |
| MCHC | Directly measured |

Concentration measurements are measurements per unit volume. As discussed above, a measurement made per unit area is proportional to a measurement made per unit volume (volume measurement with constant depth) when the depth of penetration is constant. The depth of penetration is a function of wavelength, the size of the particles with which it interacts, and refractive index. For blood, the particle size and index of refraction are essentially constant. Consequently, the depth of penetration will be constant for a particular wavelength.

Hemoglobin is the main component of red blood cells. Hemoglobin is a protein that serves as a vehicle for the transportation of oxygen and carbon dioxide throughout the vascular system. Hemoglobin absorbs light at particular absorbing wavelengths, such as 550 nm, and does not absorb light at other non-absorbing wavelengths, such as 650 nm. Under Beer's law, the logarithm of the measured transmitted light intensity is linearly and inversely related to concentration. As explained more fully below in Section 4, the apparatus of the present invention is configured so that reflected light intensity follows Beer's law. Assuming Beer's law applies, the concentration of hemoglobin in a particular sample of blood is linearly related to the negative logarithm of light reflected by the hemoglobin. The more 550 nm light absorbed by a blood sample, the lower the reflected light intensity at 550 nm, and the higher the concentration of hemoglobin in that blood sample. The concentration of hemoglobin can be computed by taking the negative logarithm of the measured reflected light intensity at an absorbing wavelength such as 550 nm. Therefore, if the reflected light intensity from a particular sample of blood is measured, the concentration in the blood of such components as hemoglobin can be directly determined.

a. Quantitative Blood Concentration Measurements

The method illustrated in FIGS. 1–4 can be used to carry out non-invasive in vivo quantitative blood concentration measurements of Hb and Hct. For example, the microvascular system beneath the mucosal membranes on the inside of the lip of a human subject can be imaged to produce the raw reflected image. To measure Hb, the raw reflected image is corrected using a bi-chromatic correction so that the logarithm of the reflected light intensity of the corrected reflected image is inversely proportional to the concentration of hemoglobin. Suitable wavelengths for such a bi-chromatic correction are $\lambda_1 = 550$ nm and $\lambda_2 = 650$ nm. The analysis image is segmented from the corrected reflected image so that the analysis image includes large vessels. The mean reflected light intensity in an area in the center of a large vessel is measured. As discussed above, the area measurements correspond to volume or concentration measurements. Consequently, the hemoglobin concentration per unit volume can be obtained by measuring the reflected light intensity in an area near the center of a large vessel.

The method of the present invention can also be used to determine the hematocrit (Hct). The difference between hemoglobin (which is the grams of hemoglobin per volume of blood) and hematocrit (which is the volume of blood cells per volume of blood) is determined by the concentration of hemoglobin within the cells which determines the index of refraction of the cells. Hence, measurements in which the image contrast between the circulation and the background is achieved principally by the scattering properties of the circulation will be related to the hematocrit and those obtained principally by the absorbing properties will be related primarily to the hemoglobin. For example, the microvascular system beneath the mucosal membrane on the inside of the lip of a human subject can be imaged to produce a raw reflected image whose contrast is determined by a difference in the scattering properties of the blood cells. To determine the volume of cells, the raw reflected image is corrected using a bi-chromatic correction such that the intensity is inversely proportional to the cell concentration. Suitable wavelengths for such a bi-chromatic correction are 900 nm (a wavelength that makes red blood cells appear dark due to their scattering properties) and 700 nm for which the contrast is minimal between the cells and their background.

b. Blood Cell Counts

Human blood is made up of formed elements and plasma. There are three basic types of formed blood cell components: red blood cells (erythrocytes); white blood cells (leukocytes); and platelets. As noted above, red blood cells contain hemoglobin that carries oxygen from the lungs to the tissues of the body. White blood cells are of approximately the same size as red blood cells, but do not contain hemoglobin. A normal healthy individual will have approximately 5,000,000 red blood cells per cubic millimeter of blood, and approximately 7,500 white blood cells per cubic millimeter of blood. Therefore, a normal healthy individual will have approximately one white blood cell for every 670 red blood cells circulating in the vascular system.

The method of the present invention can be used to determine the number of white blood cells per unit volume of blood. As discussed in more detail below in section e. regarding Blood Flow Characteristics, white blood cells are pushed to the perimeter of the blood flow, and travel in the margin where they can be seen in contrast and counted. For example, the microvascular system beneath the mucosal membranes on the inside of the lip of a human subject can be imaged to produce a raw reflected image whose contrast is determined by a difference in the optical properties of the white blood cells. This is best done where there is a spectral difference between the white blood cells and the bulk circulation (red blood cells). This occurs typically in the blue and green portions of the visual spectrum where the hemoglobin absorbs light and the white blood cells do not. Thus, for this purpose, a broad spectral region may be used (for example, from 400 to 600 nm) and bi-chromatic correction is not necessary.

The analysis image is segmented from the raw reflected image so that the analysis image includes large vessels. The number of white blood cells per unit area of blood can be counted in the analysis image. For the reasons discussed above, this will be proportional to the number of white blood cells per unit volume of blood.

Platelets are the smallest of the formed blood cell components, being typically less than 1 $\mu$ in diameter. Platelets are less abundant than red cells, but more abundant than white cells. A normal healthy individual will have approximately one platelet for every 17 red blood cells circulating in the vascular system for a total of about two trillion. Platelets help in blood clotting, since they are able to stick together under certain circumstances and help plug any holes that may develop in the walls of the blood vessels. It is evident that platelets are essential during an occurrence of injuries or other mishaps. Red blood cells are colored due to the presence of hemoglobin which absorbs particular wavelengths of light. White cells and platelets have no visual color, i.e., they contain no light-absorbing constituents in the visible range.

The platelet concentration measurement should be checked regularly as one measure of expected speed of clotting in cases of an injury to the blood vessels. Shortage of platelets (e.g., thrombocytopenia) can result in leaks in the blood vessel walls, which may be harmful or even fatal. Prior to this invention, in order to obtain platelet concentration measurement, it was necessary to extract the blood from a patient and analyze its content with regard to platelets and other blood cells, using invasive methods known in the art. It would be more advantageous to obtain an accurate platelet concentration measurement using non-invasive techniques. The current invention enables an accurate measurement of patient's blood, without any risks associated with drawing blood (e.g., AIDS, hepatitis, etc.).

The method of the present invention can be used to determine the number of platelets per unit volume of blood. For example, the microvascular system beneath the mucosal membranes on the inside of the lip of a human subject can be imaged to produce the raw reflected image. To count the number of platelets, the raw reflected image can be corrected using a velocity correction. To carry out the velocity correction, the corrected reflected image is formed by taking the difference between the raw reflected image of a particular field or scene at a time $t_0$ and the raw reflected image of the same field or scene at a time $t_1$. A corrected reflected image formed by use of such a velocity correction allows moving cells to be extracted from a stationary background.

The analysis image is segmented from the corrected reflected image so that the analysis image includes small vessels. The number of platelets per unit area can be counted in the analysis image. The counting of platelets can be done in white light, and it is not necessary to do a color or chromatic correction. The number of platelets per unit volume can be estimated by counting the number of platelets in an area in a small vessel, and relating them to the number of red blood cells in the same area. The ratio of platelets to red blood cells in healthy individuals is fairly constant at 1 to 17. In illness, this ration can vary widely in both directions, from approximately 1 to 5 to approximately 1 to 100. Therefore, the relative number of platelets to red blood cells can be used as a diagnostic tool.

In summary, the method of the present invention can be used to determine various characteristics of the vascular system through the use of known relationships between parameters.

c. Blood Cell Indices

The method of the present invention can be used to determine the mean cell volume (MCV). For example, the microvascular system beneath the mucosal membranes on the inside of the lip of a human subject can be imaged to produce the raw reflected image. Images of individual blood cells may be captured by using "stop action", i.e., stopping the action with pulsed illumination and/or shuttering. To determine the mean cell volume, the raw reflected image may be corrected using a velocity correction. To carry out the velocity correction, the corrected reflected image is formed by taking the difference between the raw reflected image of a particular field or scene at a time to and the raw reflected image of the same field or scene at a time $t$,. A corrected reflected image formed by use of such a velocity correction allows moving cells to be extracted from a stationary background.

The analysis image is segmented from the corrected reflected image so that the analysis image includes small vessels. The area of the cells in the analysis image can be determined on a pixel by pixel basis. By averaging the area of a number of cells, a relationship between average area and average or mean cell volume can be empirically established. The relationship between volume and area of an object of consistent shape, such as a human red blood cell, is determined by the equation $$Volume = (area)^{3/2} \times K$$

where K is an empirically determined shape factor. One of skill in the relevant arts can readily empirically determine shape factor K as is currently done for conventional in vitro apparatus. Consequently, the mean cell volume can be estimated from the area of cells in a small vessel.

The method of the present invention can be used to determine the mean cell hemoglobin concentration (MCHC). The determination of MCHC is carried out in a manner similar to that for determining Hb in a large vessel, except that the determination is made for Hb using individual cells in a small vessel. For example, the microvascular system beneath the mucosal membranes on the inside of the lip of a human subject can be imaged to produce the raw reflected image. The raw reflected image is corrected using a bi-chromatic correction so that the logarithm of the reflected light intensity of the corrected reflected image is proportional to the concentration of hemoglobin. Suitable wavelengths for such a bi-chromatic correction are $\lambda_1=550$ nm and $\lambda_2=650$ nm. The analysis image is segmented from the corrected reflected image so that the analysis image includes individual cells in small vessels. The mean reflected light intensity for a cell is measured from which the mean cell hemoglobin concentration can be determined.

Mean cell hemoglobin concentration (MCHC) can alternatively be determined from the equation $$MCHC=Hb \div Hct$$

Hct and Hb can be directly determined from the analysis image in the manner discussed above.

Mean cell hemoglobin (MCH) can be determined from the equation $$MCH=MCV \times MCHC$$

MCV and MCHC can be directly determined from the analysis image in the manner discussed above.

The method of the present invention can be used to differentiate between various types of white blood cells. There are five (5) types of mature white blood cells. These five types can be grouped into two categories: granulocytes that contain small granules in the cytoplasm; and agranulocytes that do not contain granules in the cytoplasm. Granulocytes can be differentiated from agranulocytes in the analysis image as a result of their scattering properties. Therefore, the method described above for determining the number of white blood cells per unit volume can be used to determine the number of granulocytes per unit volume and the number of agranulocytes per unit volume. Such information is clinically relevant. An elevated granulocyte count is indicative of a bacterial infection, and an elevated agranulocyte count is indicative of a viral infection.

d. Plasma Constituents and Components

Plasma is the fluid part of blood that occupies the space in the vessels outside of the formed blood cell components. Plasma contains a variety of constituents, one of which is bilirubin. Bilirubin is a degradation product of hemoglobin that is in solution in blood plasma. Plasma contains a variety of other compounds that are in solution, as well as compounds that are attached to formed blood cell components.

The method of the present invention can be used to determine the concentration of constituents in capillary plasma. For example, the microvascular system beneath the mucosal membranes on the inside of the lip of a human subject can be imaged to produce the raw reflected image. To determine the concentration of a constituent in capillary plasma, the raw reflected image is corrected using a bi-chromatic correction so that the logarithm of the reflected light intensity of the corrected reflected image is inversely proportional to the concentration of the constituent. For example, to determine the concentration of bilirubin in capillary plasma, a bi-chromatic correction is applied with $\lambda_1=450$ nm (an absorbing wavelength for bilirubin) and $\lambda_2=600$ nm (a non-absorbing wavelength for bilirubin to provide normalization).

The analysis image is segmented from the corrected reflected image so that the analysis image includes capillary plasma, such may be found in a small vessel. The mean reflected light intensity in an area in the capillary plasma is measured. Reflected light intensity measured in the analysis image can be converted to bilirubin concentration in the analysis image. As discussed above, the reflected images are independent of depth so that the density per unit area measurements correspond to concentration. Consequently, the bilirubin concentration per unit volume can be obtained by measuring the reflected light intensity in an area of capillary plasma in a small vessel.

The method of the present invention can be used to measure natural constituents of plasma, such as bilirubin, as explained above. The present invention can also be used to measure non-natural components of plasma, such as drugs. For example, the concentration of drugs in plasma can be measured by using a bi-chromatic correction with $\lambda_1$ equal to an absorbing wavelength for the drug and $\lambda_2$ equal to a non-absorbing wavelength for the drug in a manner similar to that for measuring the concentration of bilirubin. Alternatively, non-natural components can be detected by using an optical characteristic, e.g., native fluorescence, that appears in the analysis image.

The present invention can also be used to measure cellular and noncellular constituents of blood (natural and non-natural) through the use of a marker, label, or tag. For example, the marker, label, or tag can be introduced into the subject's vascular system in a well known manner, for example, orally or by injection. The marker can be selected so that it attaches to components dissolved in the capillary plasma to form labeled plasma components. Alternatively, the marker can be selected so that it attaches to a component that is itself attached to a formed element of the blood, such as a cell, thereby forming labeled cells. For example, a marker with identifying optical characteristics, such as a fluorescent protein, can be introduced into the vascular system so that it attaches to a certain type of cell, such as a circulating tumor cell. This technique can also be used to measure sub-classes of normal white blood cells, like lymphocyte sub-sets. The identifying optical characteristic will appear in the analysis image, such as with a fluorescent "flash". In this manner, the fluorescence or other optical contrast produced by the marker can be detected, indicating the presence of components or cells to which the marker attaches. Such determinations are useful for evaluating drug delivery. Other optical characteristics, such as near infrared or ultraviolet absorption, can also be used to detect the presence of components in capillary plasma. Tumor or other type of abnormal cells could also be detected through the use of an identifying spectral fingerprint.

e. Blood Flow Characteristics

In the particular case of the white blood cells, examination of the blood flow in vivo could also potentially provide useful information currently unavailable even with the most sophisticated laboratory techniques. The white blood cells or leukocytes are mechanically pushed to the perimeter of the blood flow. It has been shown that the process by which the white blood cells emigrate from the blood to an afflicted area is a two-step process. Because of their "sticky" interaction with the wall of the blood vessel, in the first step the white cells travel in the margin of the flow, and at a slower velocity than the red blood cells. In the second step, the white blood cells leave the circulation by migrating through the vessel wall. This distinction in the location and velocity can be used to distinguish white blood cells in the analysis image. The determination of the relative velocity of white blood cells would aid the clinician greatly in assessing the stage and severity of an infection or inflammation: lowered velocity with moderate concentration indicating an early phase, with normal velocity and elevated concentration indicating a later phase of infection or inflammation.

The method of the present invention can also be used to determine the speed or velocity of white blood cells. For example, the microvascular system beneath the mucosal membranes on the inside of the lip of a human subject can be imaged to produce the raw reflected image. To determine the speed of white blood cells, the raw reflected image can be corrected using a velocity correction. To carry out the velocity correction, the corrected reflected image is formed by taking the difference between the raw reflected image of a particular field or scene at a time $t_0$ and the raw reflected image of the same field or scene at a time $t_1$ where the difference in time between $t_0$ and $t_1$ is known. A corrected reflected image formed by use of such a velocity correction allows moving cells to be extracted from a stationary background.

The analysis image is segmented from the corrected reflected image so that the analysis image includes large vessels. The speed of white blood cells can be determined by tracking their movement per unit time. The speed of white blood cells can be used as an indicator of the presence of infection/inflammation which may be more specific than the erythrocyte sedimentation rate (ESR).

3. Feasibility Model

Figure 6A:
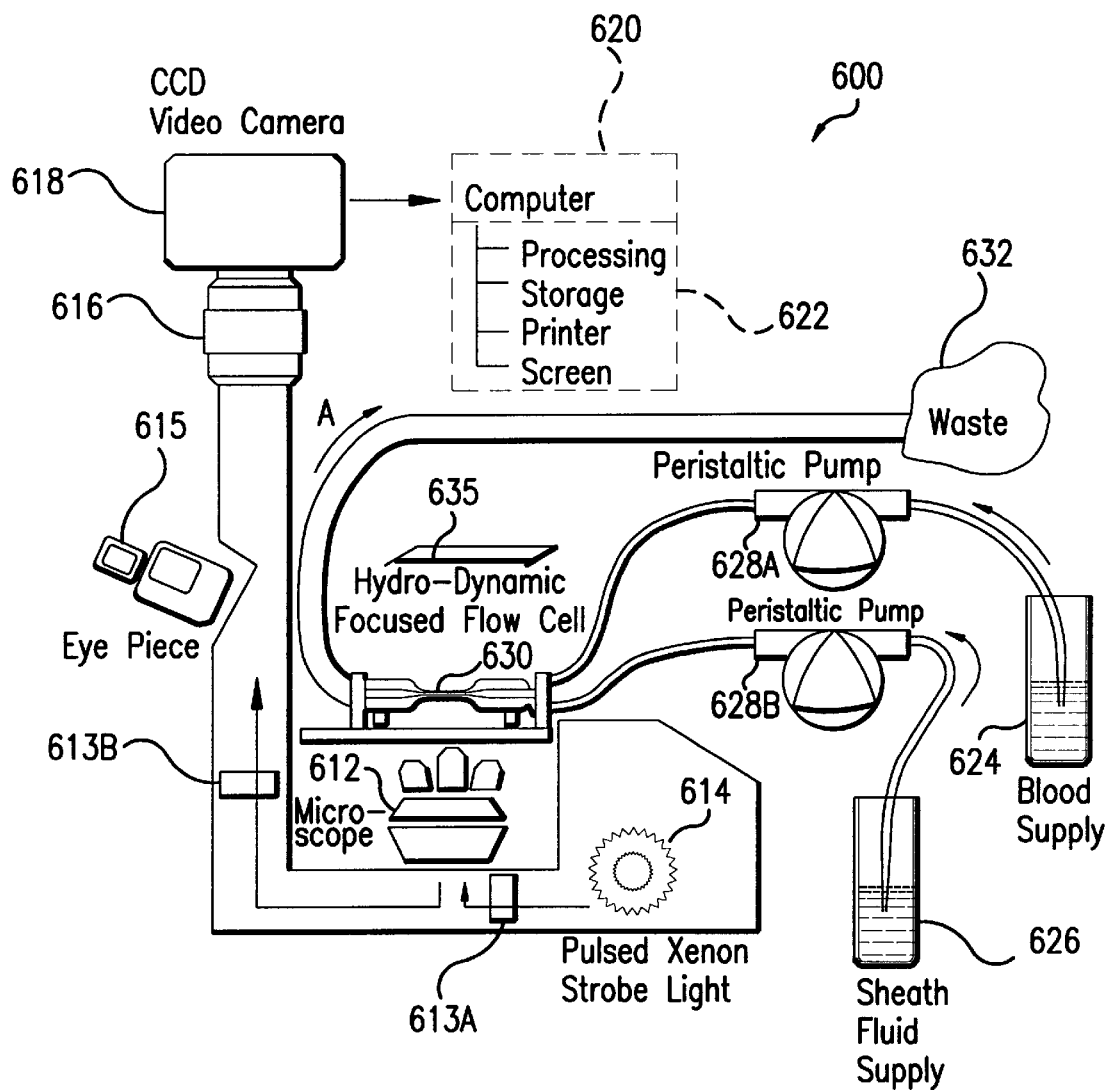
FIG. 6A illustrates a feasibility model.
Figure 6B:
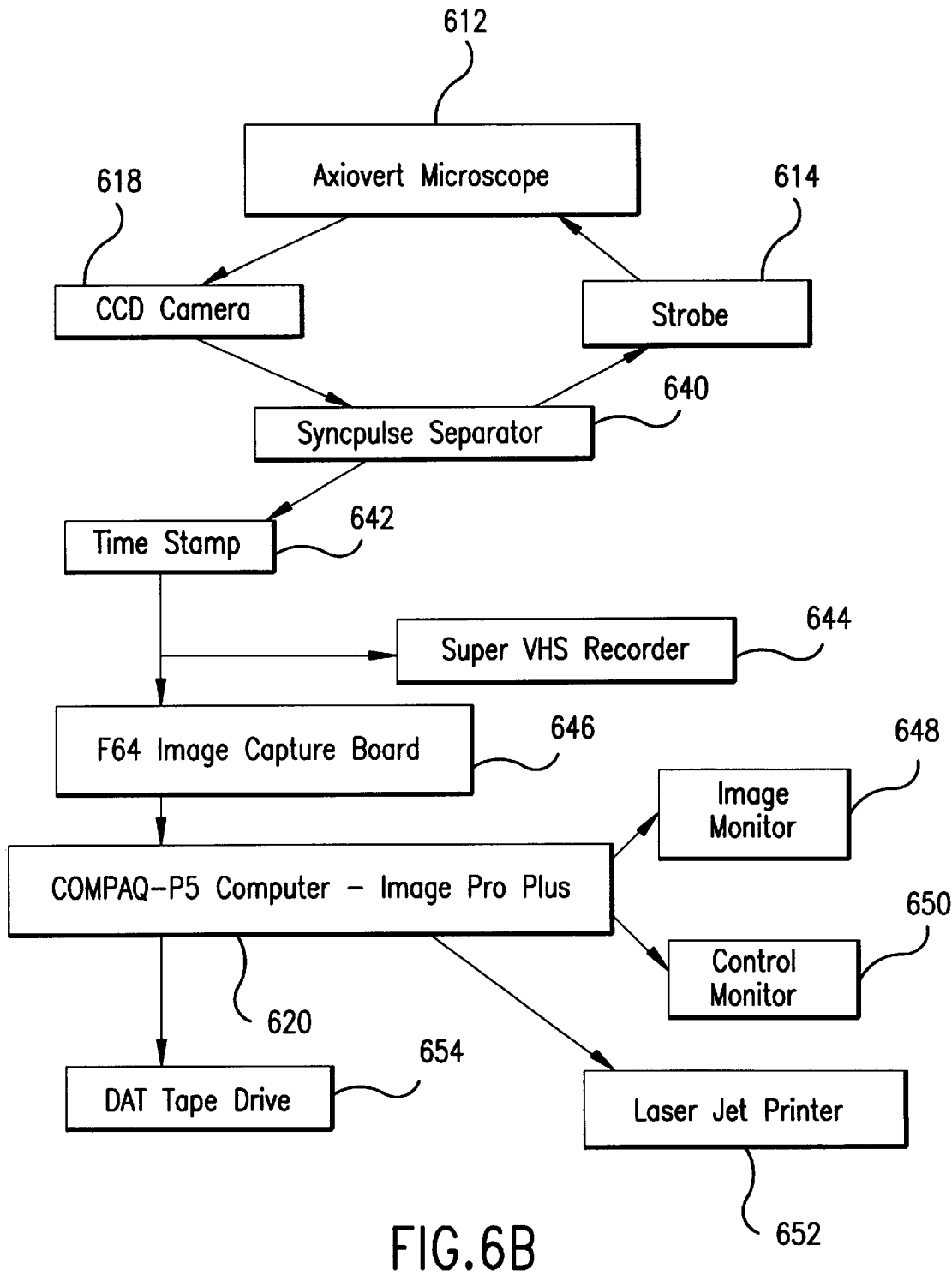
FIG. 6B illustrates a block diagram of the feasibility model shown in FIG. 6A.
Figure 7:
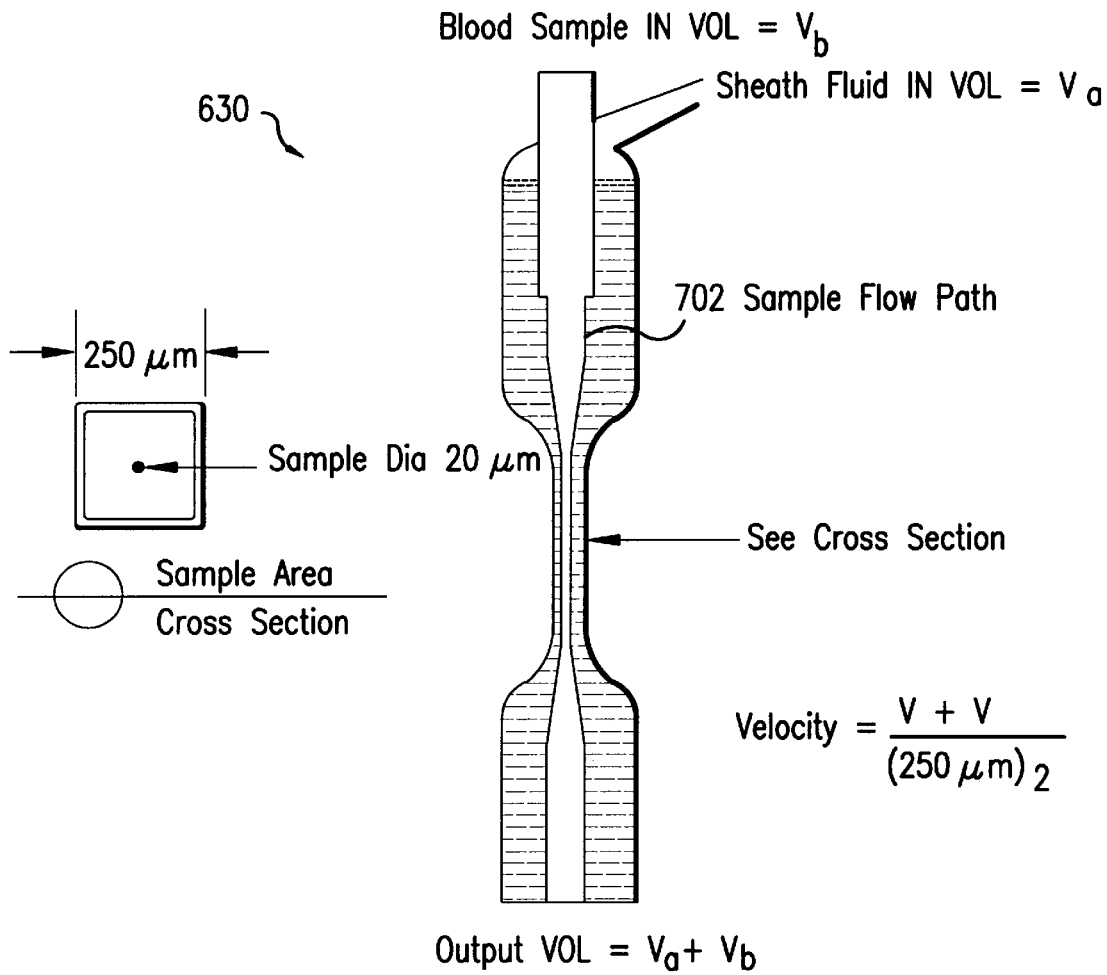
FIG. 7 shows a more detailed illustration of the hydrodynamic focused flow-cell shown in FIG. 6A.

A feasibility model, apparatus 600 (see FIGS. 6A and 6B), was developed by the inventors to verify that the method of the present invention provided results that were accurate, reliable, reproducible, and statistically significant with respect to measurements made using conventional invasive techniques for measuring blood parameters. Apparatus 600 includes a visual image receiver 612 for capturing the raw reflected image. A lens unit from a Zeiss Axiovert Model 135 microscope was used for visual image receiver 612. Light from a focusable light source 614 is focused through visual image receiver 612 to reflect off a hydro-dynamic focused flow cell 630 (explained in more detail below with respect to FIG. 7) and back through visual image receiver 612 in a co-axial manner. An exemplary light source 614 is a pulsed xenon arc light, such as is available from EG&G, Cambridge, Mass.

The reflected light carrying the raw reflected image traverses a path from flow cell 630, through visual image receiver 612, up to a high resolution video camera 618. Camera 618 is preferably an electronically shuttered, high resolution (1024×512 pixels) camera. An exemplary video camera is a Hamamatsu C2400-77 high resolution (768×497 pixels) charge coupled device (CCD) camera. Alternatively, camera 618 can be a high framing rate (300 Hz), high resolution digital video camera that can capture approximately 1,000,000 pixels of size 9 $\mu$m×9 $\mu$m, available from EG&G, Cambridge, Mass. Reflected light is collected coaxially and the reflected image is focused on the face of camera 618. Pulsed light source (strobe) 614 can be driven by a syncpulse separator 640 (FIG. 6B) to provide synchronization between camera 618 framing rate and light source 614 pulse rate. Camera 618 is in the magnified image plane of visual image receiver 612.

An eye piece 615 is inserted in the reflected light path between visual image receiver 612 and camera 618 for viewing of the reflected image. An image filter 616 is also inserted in the reflected light path between visual image receiver 612 and camera 618. Image filter 616 functions as a spectral selection filter to filter the reflected image by wavelength.

Camera 618 is coupled to a computer 620, such as a Compaq-P5, 75 MHZ computer, operating Image Pro Plus image analysis software, available from Media Cybernetics, Silver Spring, Md. The filtered image captured by camera 618 is transferred from camera 618 to computer 620 for analysis. Computer 620 includes a "frame grabber board", such as an Occulus F64 Image Capture Board 646, available from Coreco, Montreal, Canada to capture the signal with the image data from camera 618. Preferably, a 10-bit frame grabber board is used to provide sufficient digital resolution. Computer 620 is coupled to one or more output devices 622 for display processing and/or storage. Output device 622 can be a hard disk drive or other type of storage device such as DAT tape drive 654, a central processing unit (CPU), a printer such as laser jet printer 652, a computer screen or monitor such as video image monitor 648, a computer monitor such as control monitor 650, etc.

The output of camera 618 can also be sent to a recorder 644, such as a super VHS recorder. A time stamp 642 can be added to the output of camera 618 before it is sent to computer 620 and recorder 644.

Advances in video camera technology have greatly increased the number of pixels capable of operating at high framing rates. Captured images of blood flow containing as many as 1 million pixels separated by a few milliseconds can be used to visualize red blood cells, in vivo, and to analyze blood flow in sites separated from the external environment by thin layers of transparent or translucent material. The movement of individual red blood cells between frames of high speed sequential images can be used to enhance signal to noise ratio and to suppress the stationary background.

The fundamental accuracy of apparatus 600 to dynamically capture particle sizes ranging from 0.94 to 10 $\mu$m with a correlation coefficient >0.99 using commercially available polystyrene beads has been established.

Apparatus 600 was used to obtain reflected images of flowing blood to provide a feasibility model for in vivo reflected images of the vascular system. Blood from a blood supply 624 is pumped by a peristaltic pump 628A through flow cell 630 in the direction shown by arrow A to a waste reservoir 632. At the same time, sheath fluid from a sheath fluid supply 626 is pumped by a peristaltic pump 628B through flow cell 630 in the direction shown by arrow A to waste reservoir 632. The sheath fluid is an isotonic medium that is used to simulate the walls of the blood vessels and other tissues surrounding blood. As shown in more detail in FIG. 7, the cross-section of sample flow path 702 is smallest in the region above visual image receiver 612. By controlling the ratio by which the cross-section of sample flow path 702 narrows, laminar flow can be maintained. The cross-section of sample flow path 702 can be adjusted so that individual cells can be seen in the reflected image.

The model used is an adaptation of the hydrodynamic focused flow cells developed for use in flow cytometers. In this flow cell, a narrow "sample stream" containing the blood is encased in an inert sheath fluid, and the combined fluidic system is caused to flow between two glass plates separated by approximately 250 $\mu$m. Altering the flow of the sheath fluid has the effect of reducing the sample stream size from greater than 100 $\mu$m to approximately 10 $\mu$m in diameter, thus very closely representing typical capillaries of the microvascular system.

With this flow cell, important parameters of the experiment can be independently varied as follows:

The blood cell velocity, which is controlled by the volume flow of the sheath fluid, can be varied from 100 to 1,000 $\mu$m per second.

Sample stream diameter, controlled by the relative sheath to sample flow volume, can be varied over a range from 10 $\mu$m to 100 $\mu$m.

Pulsing can be introduced both in diameter and in velocity by varying the flow rates of the sample and sheath stream.

The effect of a thin layer of tissue (Mucous Membrane) can be simulated by adding a scattering element either to the stationary glass window or in the sheath fluid.

To improve visualization of the reflected image of the blood flowing through flow cell 630, two polarizers were used in apparatus 600 (see FIG. 6A) A first polarizer 613A was placed in the light path between light source 614 and visual image receiver 612. A second polarizer 613B was placed in the reflected light path between the flow cell 630 containing the imaged blood flow, and camera 618. The two polarizers are "crossed" in that the planes of polarization are 90° relative to each other. For example, the plane of polarization of polarizer 613B is 90° relative to the plane of polarization of polarizer 613A. Likewise, the plane of polarization of polarizer 613A is 90° relative to the plane of polarization of polarizer 613B. Through the use of polarizer 613A and 613B, the reflected image that is captured by camera 618 is enhanced, making the blood cell components more sharply contrasted with respect to the background, thereby providing an improved visualization of the blood flow. The improved visualization through the use of cross-polarizers will be explained in more detail in Section 4 below regarding an in vivo apparatus. A diffuse reflector 635 was also used with apparatus 600 to reflect light and simulate reflection from a tissue background.

With apparatus 600, the basic feasibility of using images in reflected light to quantify four RBC parameters (RBC, MCV, Hb, and MCHC) has been demonstrated. The following table summarizes the correlation between values obtained using the feasibility model (apparatus 600) and those obtained using a Coulter Stk.S (N=number of samples; r=correlation coefficient).

| Parameter | N | r |
| --- | --- | --- |
| Hb | 70 | 0.9 |
| MCHC | 20 | 0.55 |
| MCV | 45 | 0.70 |
| RBC | 38 | 0.63 |

Using apparatus 600, the velocity and dimensions of the blood flow can be experimentally manipulated in flow cell 630 to simulate in vivo conditions. Apparatus 600 can also be used to measure blood flow, for example, in a patient's finger located above visual image receiver 612 in place of flow cell 630.

Apparatus 600 was used by the inventors in an agreement and correlation study to confirm that the present invention could be clinically used to provide accurate non-invasive in vivo results. Hemoglobin concentration was measured using apparatus 600 and seventy patient blood samples obtained from a hospital for blood supply 624. Blood from the same seventy blood samples was analyzed using a conventional Coulter Stk.S analyzer, manufactured by Coulter Diagnostics of Miami, Fla. For each of the seventy samples run on apparatus 600 and the Coulter device, a determination was made whether the hemoglobin concentration indicated an anemic condition or a normal condition. As shown in FIG. 8A, the determination made using the feasibility model agreed with the determination made using the Coulter device for 67 of the 70 samples, for a 96% agreement. As compared to the Coulter device, apparatus 600 provided 1 false high (anemia when Coulter indicated normal) and 2 false lows (normal when Coulter indicated anemia).

Figure 9:
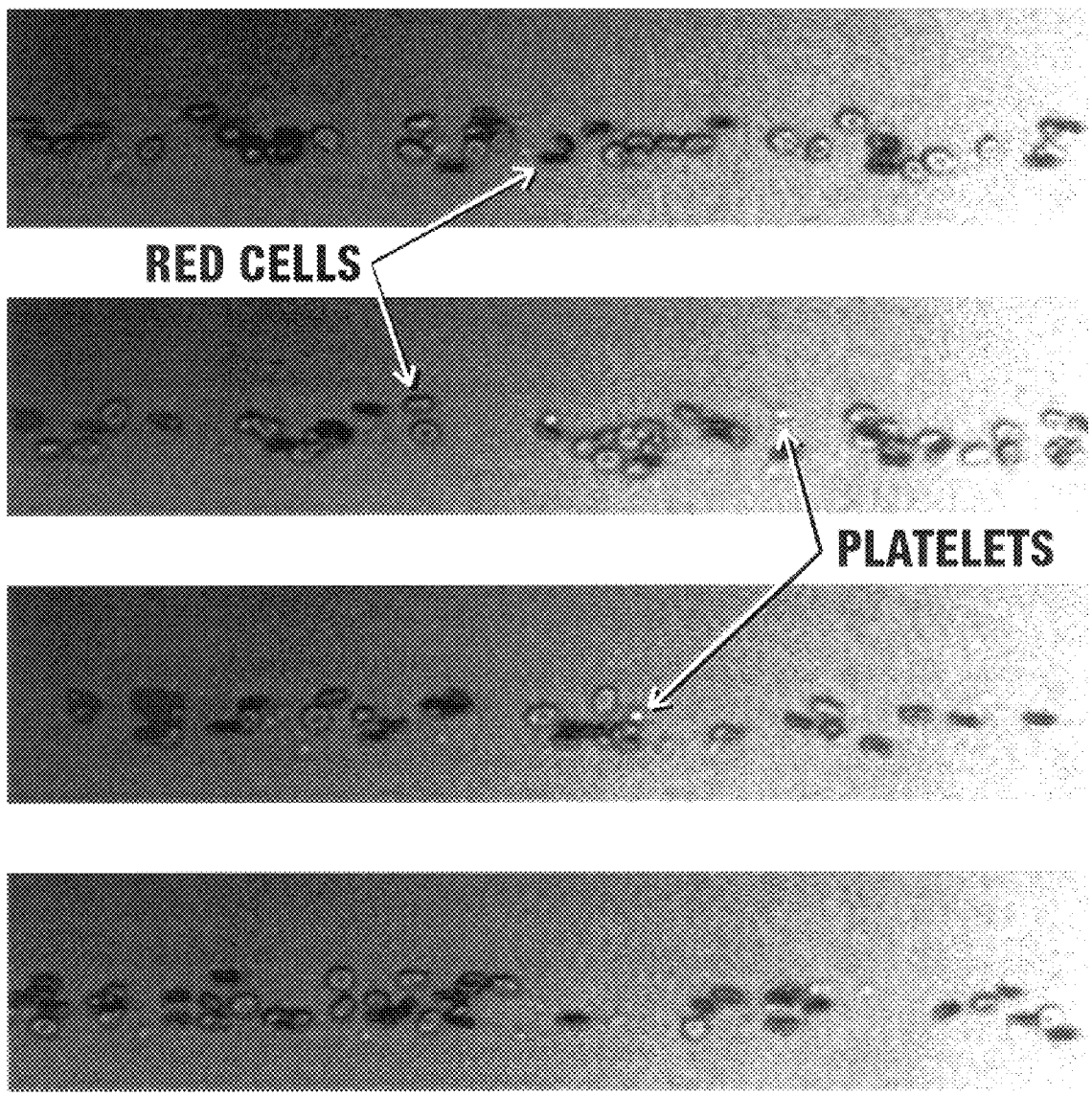
FIG. 9 shows images of red cells and platelets using the feasibility model.

A number of experiments were performed using apparatus 600 to measure various characteristics of the vascular system. For example, apparatus 600 was used to generate images of blood flowing through flow cell 630. Light in the range between 400 nm and 1000 nm was emitted from light source 614. Images were captured at 450 nm, 500 nm, 550 nm, 600 nm, 650 nm, 700 nm, 750 nm, 800 nm, 850 nm, and 900 nm by selection of appropriate image filters 616. One example of an image obtained with apparatus 600 is shown in FIG. 9. Platelets are shown as white dots, in comparison with red blood cells which are of a darker shade.

Apparatus 600 was also used to confirm that measurements could be made in the capillary plasma, or space between the cells in a small vessel such as a small capillary. By eliminating or ignoring the portions of the images relating to blood cells, etc., measurements relating to non-formed constituents may be made. Using a hydrodynamically focused flow cell, four different concentrations of bilirubin were added to a ¼ whole blood dilution. The final bilirubin levels ranged from 6.2 g/dl to 24.8 g/dl. A xenon flashlamp was used to illuminate the field and images were recorded with two different optical filters, one at a principle absorption wavelength for bilirubin (450 nm) and one outside the absorption band of bilirubin (600 nm).

Figure 10:
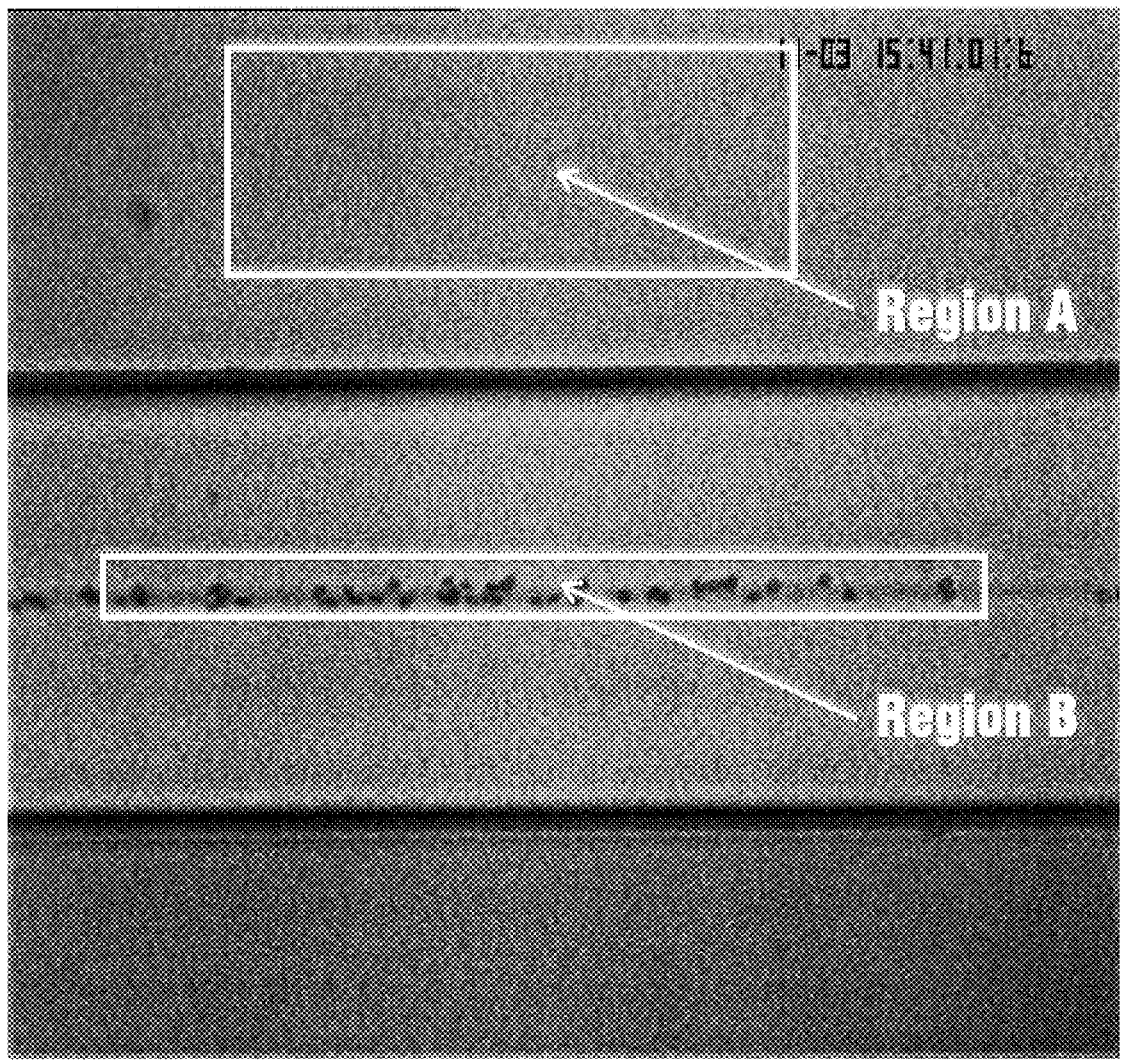
FIG. 10 shows an area of interest around a background (region A), to be used as a reference, and an area of interest inside a flowing stream (region B)

After the images were taken, the analysis involved defining an area or scene of interest around a background (region A) to be used as a reference (see FIG. 10). An area of interest inside the stream flowing through flow cell 630 (region B) was also defined. Region B was segmented to eliminate the images of the red blood cells. This was done by using an intensity threshold that separates the red blood cells out of region B. The optical density was then determined for the remaining area of region B to perform the analysis.

Figure 11:
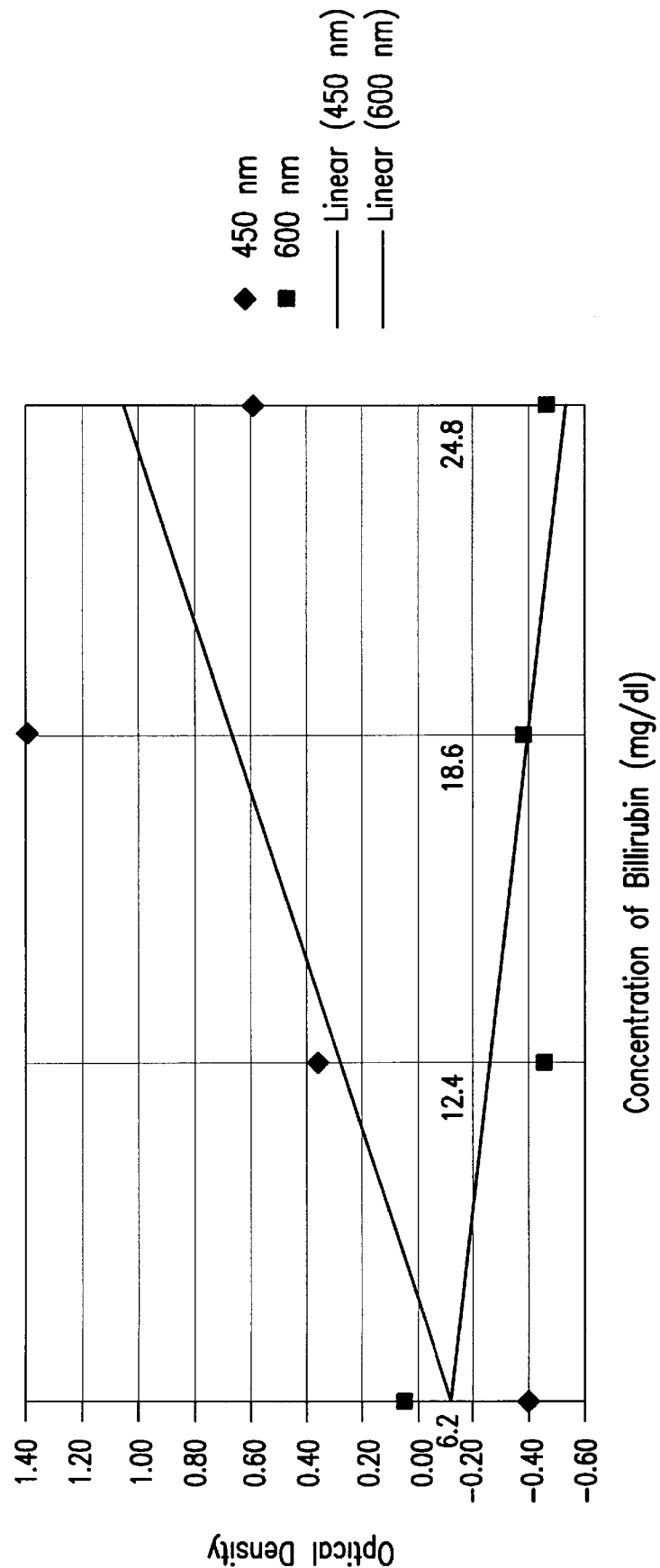
FIG. 11 shows a chart of optical density versus concentration of bilirubin.

FIG. 11 shows a plot of optical density and concentration of bilirubin (mg/dl). FIG. 11 shows a marked increase in the optical density at the absorbing wavelength (450 nm) relative to the non-absorbing wavelength (600 nm).

Figure 12:
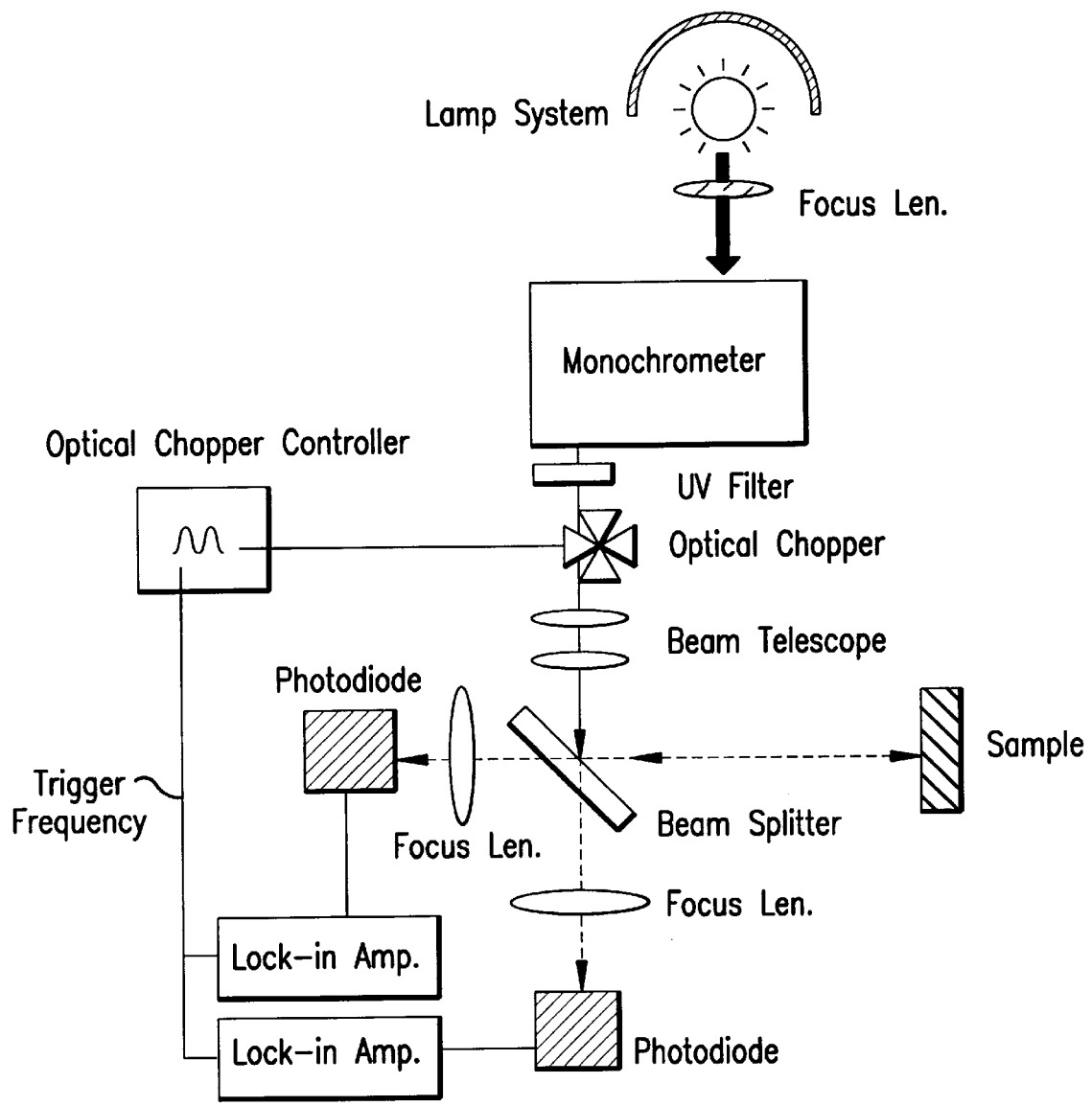
FIG. 12 illustrates a chopper stabilized reflectance spectrophotometer.
Figure 13:
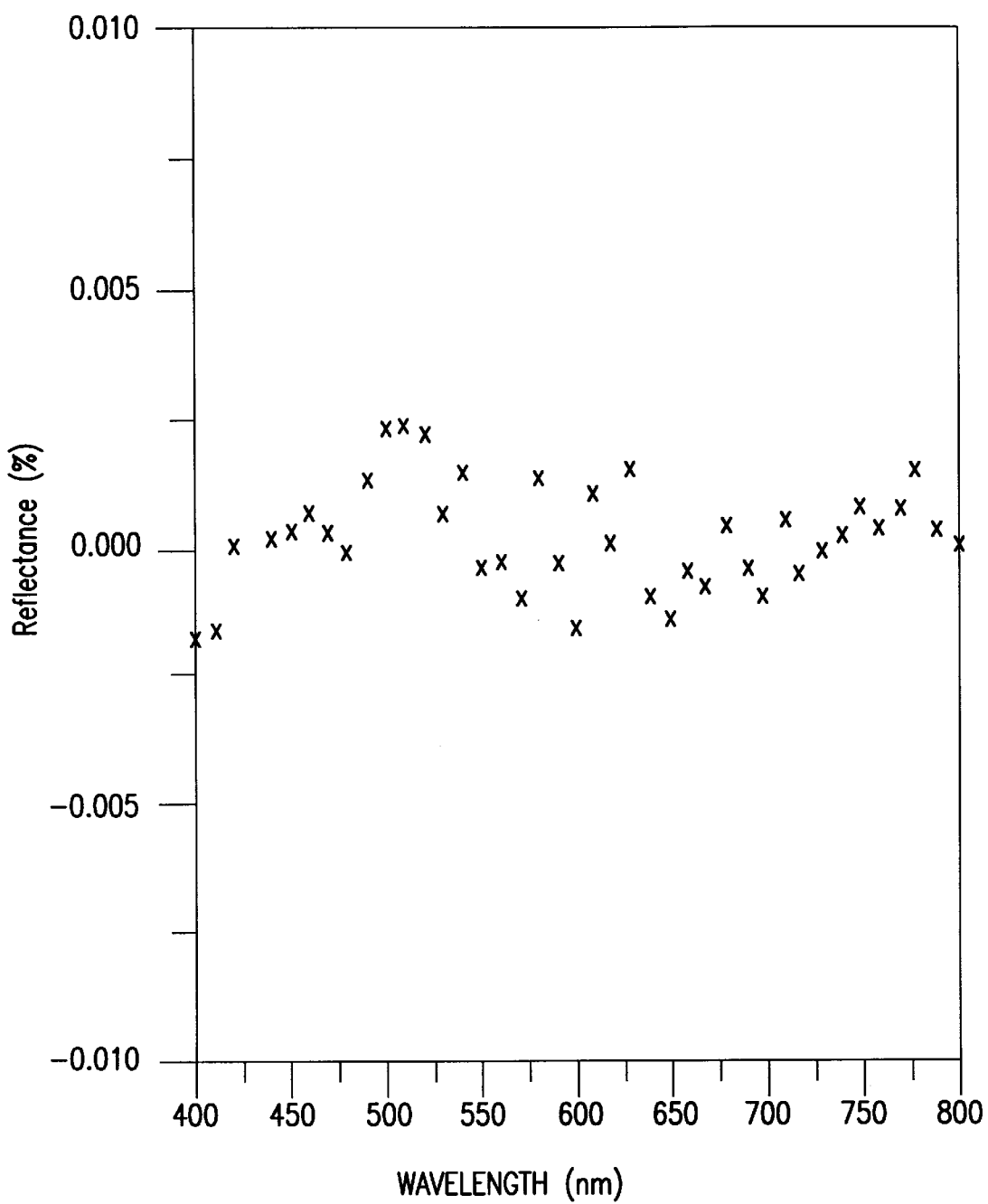
FIG. 13 shows a reflectance spectral scan for leukopheresed plasma.
Figure 14:
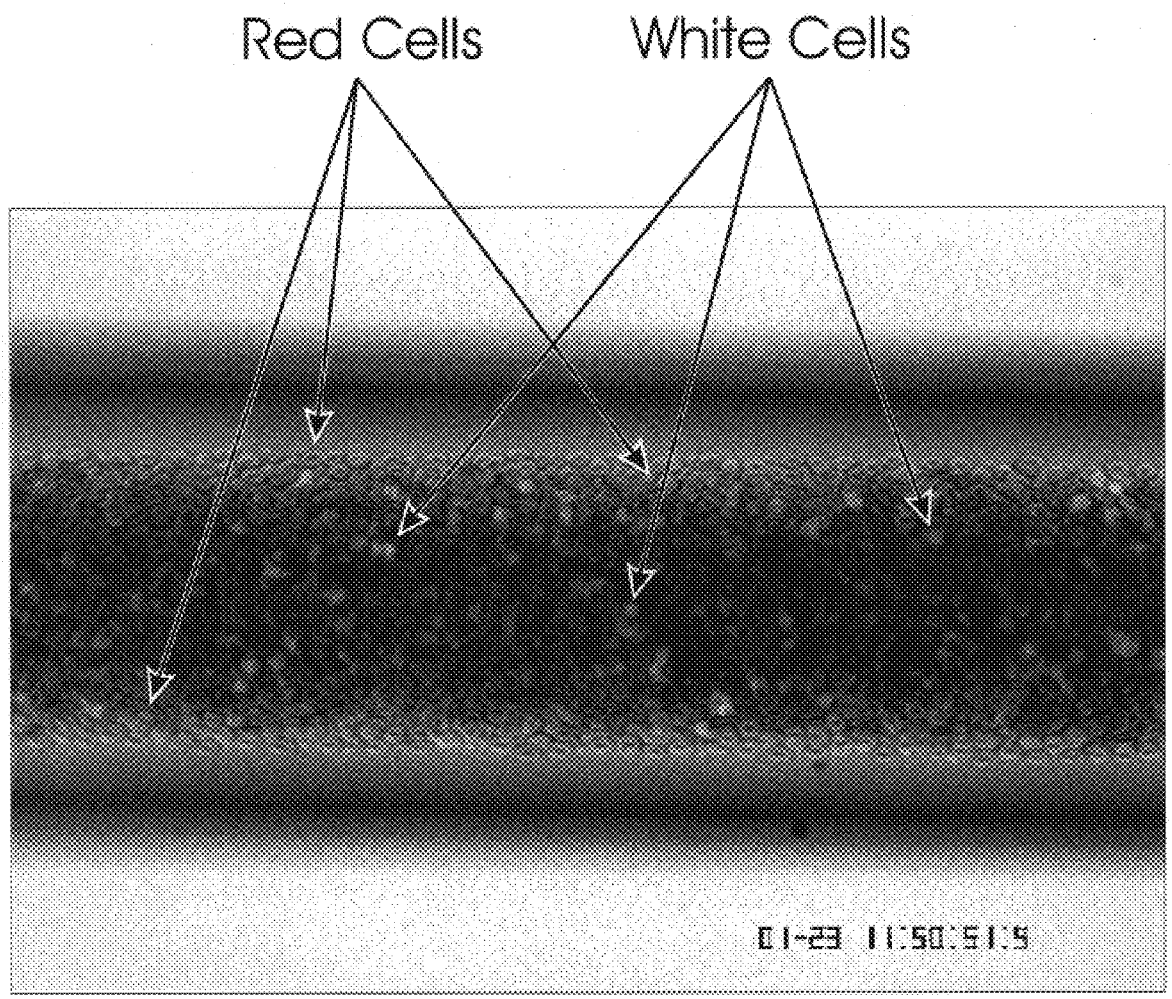
FIG. 14 shows a leukemic blood sample image obtained with the feasibility model.

Experiments were conducted with a chopper stabilized reflectance spectrophotometer (see FIG. 12) to determine the reflection characteristics of white blood cells or leukocytes. The resulting reflectance spectral scan is shown in FIG. 13 (reflectance % as a function of wavelength in nm). FIG. 13 shows that the reflected light for white blood cells is relatively high in the spectral region around 550 nm, where the reflected light of red blood cells is attenuated by the absorption of hemoglobin. A spectral selection filter centered at 550 nm (image filter 616) was used in apparatus 600 to obtain an image of leukemic blood in a 100 µm glass capillary (see FIG. 14). The leukemic blood shown in FIG. 14 has a higher number of white blood cells (44,000/µl) than does normal or healthy (7500/µl) blood. White blood cells are visible in FIG. 14 as bright spots against the darker background of the red blood cells.

4. In Vivo Apparatus

Figure 15A:
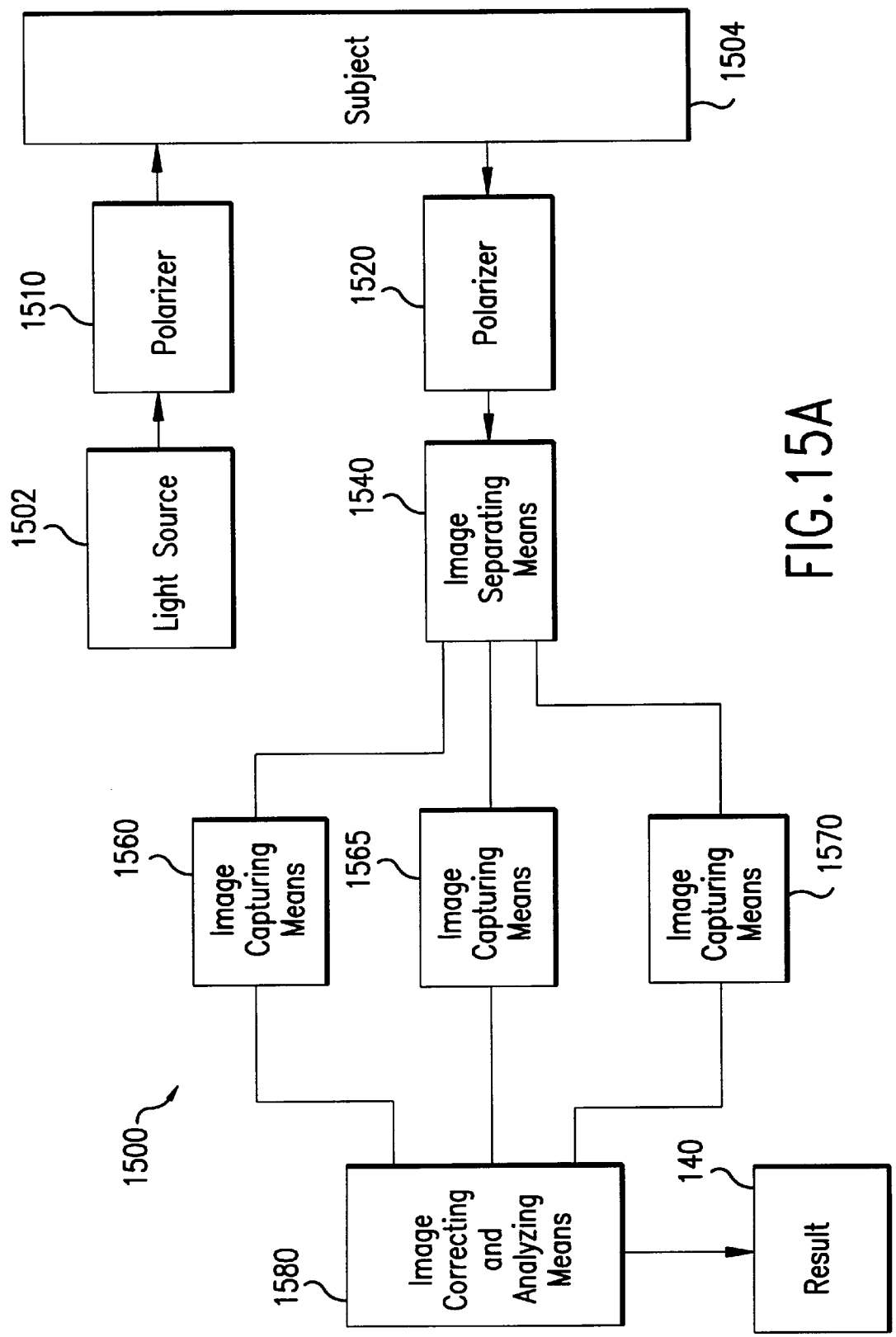
FIG. 15A shows a block diagram illustrating one embodiment of an in vivo apparatus.

FIG. 15A shows a block diagram illustrating one embodiment of an in vivo apparatus 1500 for non-invasive in vivo analysis of a subject's vascular system. Apparatus 1500 includes a light source 1502 for illuminating tissue of a subject (shown generally at 1504). Although one light source is shown, it is to be understood that the present invention is not limited to the use of one light source, and more than one light source can be used. In an embodiment where more than one light source is used, each light source can be monochromatic or polychromatic. Light source 1502 can be a light capable of being pulsed, a non-pulsed light source providing continuous light, or one capable of either type of operation. Light source 1502, can include, for example, a pulsed xenon arc light, a mercury arc light, a halogen light, a tungsten light, a laser, a laser diode, or a light emitting diode (LED). Light source 1502 can be a source for coherent light, or a source for incoherent light.

A first polarizer 1510 is placed between light source 1502 and subject 1504. First polarizer 1510 polarizes light from light source 1502. A second polarizer 1520 is placed between subject 1504 and an image separating means 1540. Polarizers 1510 and 1520 preferably have planes of polarization oriented 90° relative to each other.

In one embodiment of the present invention, light source 1502 comprises first polarizer 1510 so that a separate first polarizer 1510 is not required. In such an embodiment, light source 1502 is a source of polarized light, for example, a laser or a laser diode, and second polarizer 1520 has a plane of polarization oriented 90° relative to the plane of polarization of polarized light source 1502.

The reflected spectral image from subject 1504 is reflected from a depth less than a multiple scattering length. Image separating means 1540 separates the reflected spectral image from subject 1504 into two or more image portions. Each image portion is captured by an image capturing means, such as image capturing means 1560, 1570, and 1565. Each image capturing means is coupled to an image correcting and analyzing means 1580 for carrying out image correction and analysis to produce result 140.

Figure 15B:
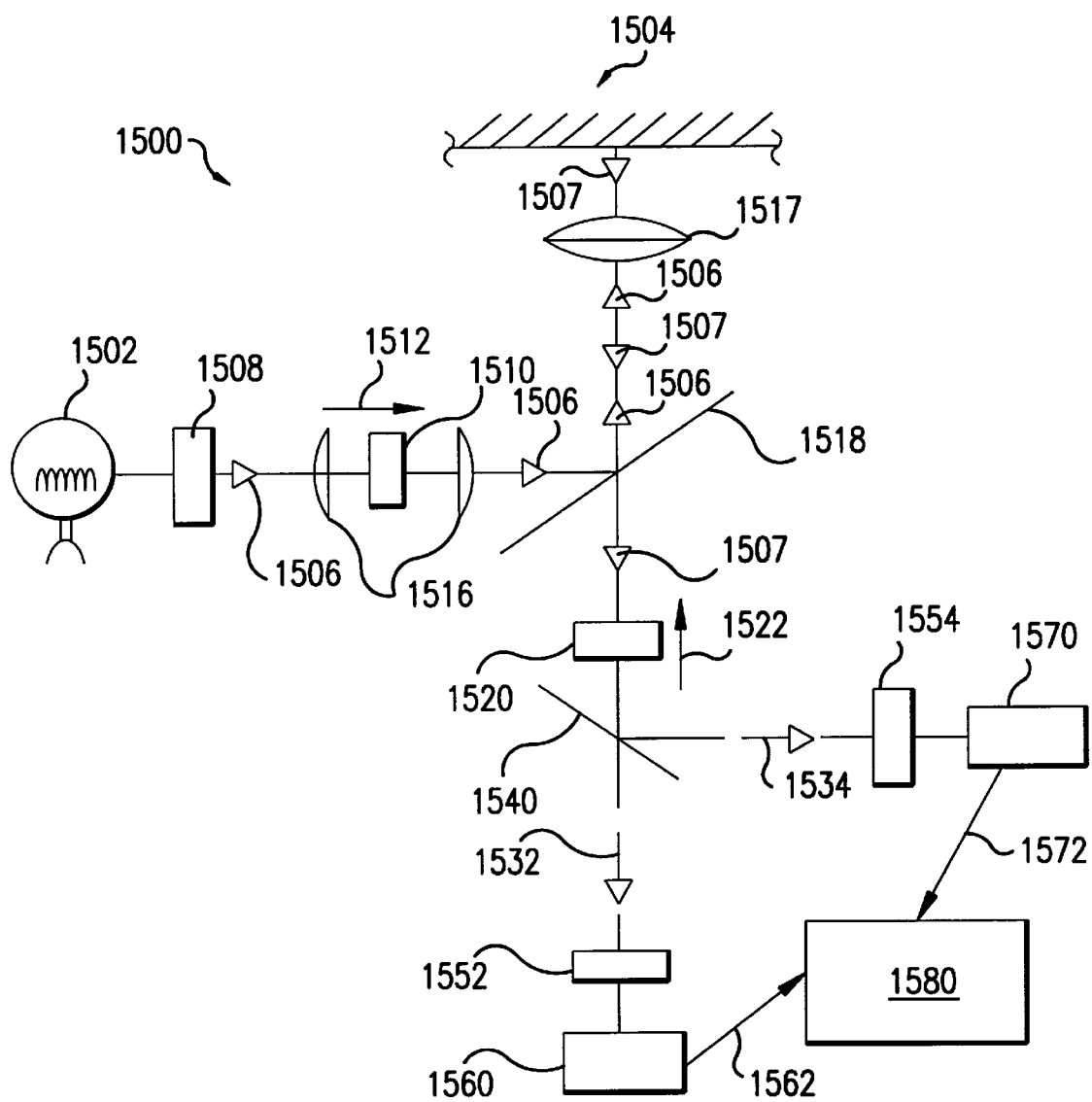
FIG. 15B shows further detail of the in vivo apparatus shown in FIG. 15A.

FIG. 15B shows further detail of in vivo apparatus 1500. A beam splitter 1518 is used to form a light path 1506 between light source 1502 and the illuminated tissue and a reflected light path 1507. The reflected image that is reflected from a depth less than the multiple scattering length in the illuminated tissue travels along reflected light path 1507 to image capturing means 1560 for capturing the reflected image. Suitable image capturing means 1560 include those devices capable of capturing a high resolution image as defined above. The image capturing means captures all or part of an image for purpose of analysis. Suitable image capturing means include, but are not limited to, a camera, a film medium, a photocell, a photodiode, a photodetector, or a charge coupled device camera. For example, video cameras and charge coupled device (CCD) cameras having a 1024×512 pixel resolution and 300 Hz framing rate can be used. A particularly preferred image capturing means is a Hamamatsu C2400-77 high resolution CCD camera.

The resolution required for the image capturing means can depend upon the type of measurement and analysis being performed by the in vivo apparatus. For example, the image resolution required for determining the hemoglobin concentration (Hb) is lower than the image resolution required for making cellular measurements, such as MCV or cell counts. For example, hemoglobin concentration measurements can be carried out using photocells, such as one red photocell and one green photocell, as the image capturing means.

First polarizer 1520 is placed in light path 1506 between light source 1502 and the illuminated tissue. First polarizer 1510 polarizes light from light source 1502. Polarizer 1510 has a plane of polarization, shown generally at 1512. Second polarizer 1520 is placed in reflected light path 1507 between the illuminated tissue and image capturing means 1560. Polarizer 1520 has a plane of polarization, shown generally at 1522. As shown in FIG. 15B, planes of polarization 1512 and 1522 are oriented 90° relative to each other. Polarizers, such as polarizers 1510 and 1520, having planes of polarization oriented 90° relative to each other are referred to herein as "cross-polarizers".

The efficiency of a polarizer is a function of the percentage of the input light that is transmitted through the polarizer. For each unit of unpolarized (randomly polarized) light input to a polarizer, a perfectly efficient polarizer would transmit out 50% of the inputted light. When randomly polarized light is input to two perfect polarizers (regardless of efficiency) configured as cross-polarizers, all light is extinguished, i.e., no light is transmitted through the second polarizer. The more light that is extinguished by cross-polarizers (i.e., the less randomly polarized light that is transmitted through the cross-polarizers), the greater the extinction of the cross-polarizers. Cross-polarizers having an extinction coefficient of at least $10^{-3}$ (for each unit of randomly polarized light input into the cross-polarizers, 1/1000 is transmitted through the cross-polarizers) are suitable for use with the present invention. Suitable cross-polarizers are available as sheet polarizers from Polaroid Corp., Massachusetts.

As stated above, virtually all of the light is eliminated when high extinction polarizers are crossed. Therefore, the expected result using crossed-polarizers as described for the apparatus of the present invention, would be to extinguish all of the illuminated image. The unexpected result of how the use of cross-polarizers in the apparatus of the present invention increases visualization of reflected images, and increases the ability to perform quantitative analysis using reflected images, will now be explained. Reflected light has three components. First is the "mirror or specular reflection" component that preserves the image of the source in a reflection. The second component is a "rough surface scattering" component. The rough surface scattering component is scattered light that is scattered by a rough surface, and does not preserve the image of the source. However, both the mirror reflection component and the rough surface scattering component retain polarization. The third and final component is a "small particle scattering" component, commonly known as a "Rayleigh scattering" component. The Rayleigh scattering component is light that is scattered by particles that are small compared to the wavelength of the illuminated light. Rayleigh scattering de-polarizes light. Therefore, the Rayleigh scattering component is the only component of reflected light that is de-polarized so that the original polarization is lost.

The only component of reflected light that passes through "cross-polarizers", such as polarizers 1510 and 1520 oriented at 90° relative to each other, is the Rayleigh scattering component. The mirror reflection component and the rough surface scattering component retain polarization. Therefore, if the mirror reflection component and the rough surface scattering component of light polarized in a first direction (such as by polarizer 1510) are passed through a polarizer oriented at 90° relative to the first direction (such as polarizer 1520), these two components of the reflected light are extinguished. In contrast, the Rayleigh scattering component of light polarized in a first direction is de-polarized. Therefore, the Rayleigh scattering component is not extinguished when it passes through a polarizer oriented at 90° relative to the first direction of polarization. Also, the Rayleigh scattering component has lost the image of the source, and effectively provides a uniform source of reflected light from within the object.

With reference to FIG. 15B, light from light source 1502 is polarized in a first direction 1512 by polarizer 1510. The light thus polarized reflects from object 1504. The Rayleigh scattering component of the reflected light is depolarized. However, the mirror reflection component and the rough surface scattering component retain the polarization from polarizer 1510. When the reflected light passes through polarizer 1520 oriented in a second direction 1522 90° relative to first direction 1512, the mirror reflection component and the rough surface component are extinguished. Therefore, the only component of reflected light that passes through polarizer 1520 is the Rayleigh scattering component that has been de-polarized in direction 1522, and which exhibits an intensity which varies as the cosine of the angle with the incident light.

When cross-polarizers are used, such as polarizers 1510 and 1520 oriented at 90° relative to each other, only the de-polarized reflected light, i.e., the Rayleigh scattering component is observed. The mirror reflection component and the rough surface scattering component are eliminated. Contrary to the expectation noted above that no light would be transmitted with cross-polarizers, the light depolarized by Rayleigh scattering provides a virtual backlighting effect that significantly increases the contrast and visualization of reflected images, and the ability to perform quantitative analyses using reflected images. The increased visualization and quantitative ability are due to two consequences resulting from the use of cross-polarizers as described above. First, the mirror reflection component and the rough surface scattering component, which are both a source of noise for quantitative measurement, are eliminated. Second, the Rayleigh scattering component is "Lambertian" in that it behaves in the same manner as light reflected from a Lambertian surface. Therefore, the Rayleigh scattering component is independent of the angle of viewing, and allows concentration to be computed more simply from measured reflected light intensity (analogous to Beer's Law).

Under Lambert's law, the luminous intensity in a given direction radiated or reflected by a perfectly reflecting plane surface varies as the cosine of the angle between that direction and the normal to the surface. A Lambertian surface is an ideal, perfectly reflecting surface for which the brightness of reflected radiation is independent of direction. Light reflected from a Lambertian surface appears equally bright from all angles, like freshly fallen snow. Most surfaces are not Lambertian, and the intensity of reflected light depends upon the angle of viewing because of surface effects.

Figure 18A:
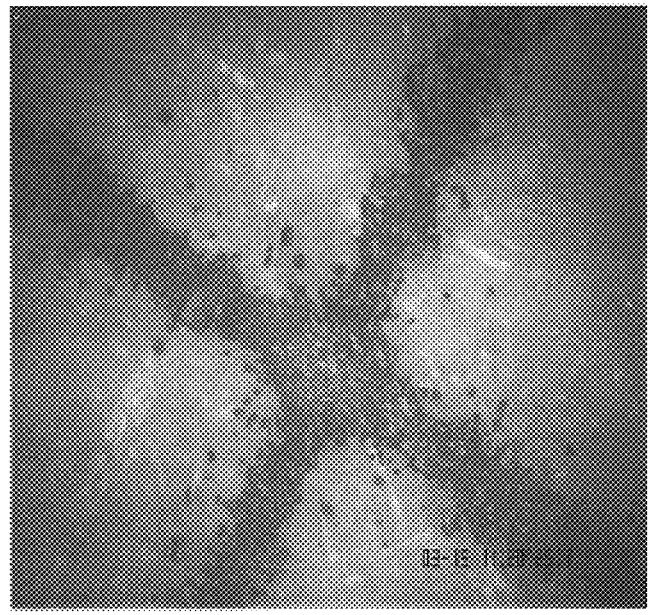
FIG. 18A shows an ink-jet cross visualized in conventional reflected light.
Figure 18B:
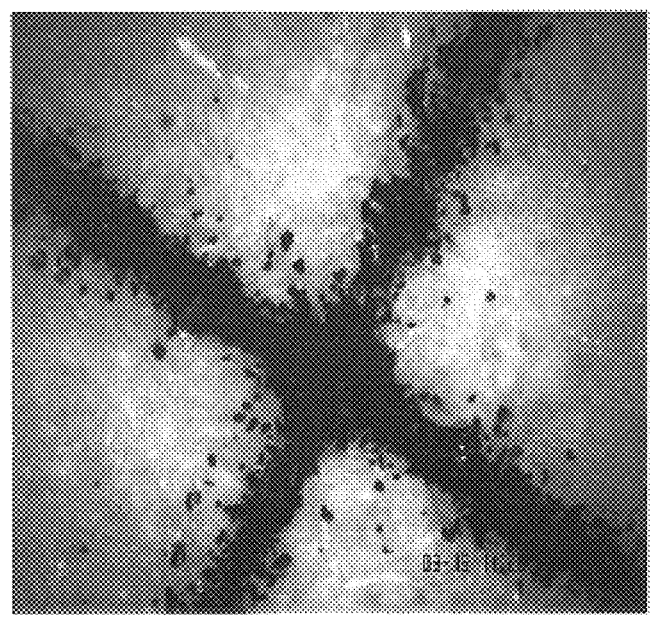
FIG. 18B shows an ink-jet cross visualized in reflected light using the cross polarization technique of the present invention.

The increased visualization that is achieved through the use of the cross-polarization technique of the present invention can be seen by comparing FIGS. 18A and 18B. FIG. 18A illustrates a black ink-jet cross visualized using conventional optics without cross-polarizers. Visualization of the ink-jet cross is difficult because of the relatively poor contrast between the ink-jet cross and the background. FIG. 18B illustrates the same black ink-jet cross used in FIG. 18A visualized using the cross-polarization technique of the present invention, i.e., polarizers such as 1510 and 1520 oriented at 90° relative to each other. FIG. 18B dramatically demonstrates the improvement in visualization and contrast obtained by using cross-polarizers. This image is the same as the one that would be observed if the image was from transmitted light. The reflection seen with conventional reflected light in FIG. 18A has been removed in FIG. 18B through the use of cross-polarizers.

As shown in FIG. 15B, an objective lens 1517 is placed co-axially in light path 1506 and reflected light path 1507. Objective lens 1517 magnifies the reflected image. Image capturing means 1560 is located in a magnified image plane of objective lens 1517. Preferably, objective lens 1517 is selected with the lowest magnification level required to visualize the illuminated tissue. The magnification required is a function of the size of the object in the illuminated tissue to be visualized, along with the size of the pixels used for the image. Low magnification provides a high depth of field, but more crudeness to the image. High magnification provides a low depth of field, but is more susceptible to blurring caused by motion. Blood vessels in the microvascular system are typically 10–40 $\mu$ in diameter. Ten to twenty (10–20) pixels per blood vessel diameter provide a suitable image with a 10X lens. Lower magnification could be used with pixels of smaller size.

Lenses 1516 can be used on either side of polarizer 1510 for focusing the light in light path 1506. A heat rejection filter 1508 is preferably placed in front of light source 1502 to reject heat. Filter 1508 is a blocking filter to block out infra-red wavelengths. Filter 1508 is preferably configured to block wavelengths greater than or equal to 1000 nm.

Image separating means 1540 is placed in reflected light path 1507 between second polarizer 1520 and image capturing means 1560 for separating the reflected image into a first portion 1532 and a second portion 1534. It is to be understood that image separating means 1540 can separate the reflected image into a plurality of portions, and is not limited to two portions. First portion 1532 of the reflected image is captured by image capturing means 1560. Second portion 1534 is captured by second image capturing means 1570. Second image capturing means 1570 can be the same as or different from image capturing means 1560. Second image capturing means 1570 is disposed in the magnified image plane of objective lens 1517. Additional image capturing means can be used to capture further image portions separated by image separating means 1540. In an alternative embodiment, a single image capturing means can be used to capture first portion 1532 and second portion 1534 of the reflected image.

One particularly preferred image separating means is a dichroic mirror or other type of dichroic separator that transmits all light less than a particular wavelength, and reflects all light greater than the particular wavelength. Alternatively, an image separating means can be used that reflects all light less than a particular wavelength, and transmits all light greater than the particular wavelength. Other suitable image separating means can also be used.

A spectral selection means 1552 can be placed in reflected light path 1507 between second polarizer 1520 and image capturing means 1560. Spectral selection means 1552 can be, for example, a monochromator, a spectral filter, prism, or grating. Similarly, a spectral selection means 1554 can be placed in reflected light path 1507 between second polarizer 1520 and second image capturing means 1570. Spectral selection means 1554 can also be, for example, a monochromator, a spectral filter, prism, or grating. The center values for spectral selection means 1552 and 1554 can be chosen based upon the type of analysis to be conducted. For example, if hemoglobin concentration is to be determined, then one of spectral selection means 1552 or 1554 is preferably centered at 550 nm and the other of spectral selection means 1552 or 1554 is preferably centered at 650 nm. As another example, if bilirubin concentration is to be determined, then one of spectral selection means 1552 or 1554 is preferably centered at 450 nm and the other of spectral selection means 1552 or 1554 is preferably centered at 600 nm.

In a particularly preferred embodiment, light source 1502 is configured as a plurality of LED's, each LED emitting a different wavelength of light. For example, three LED's can be used to provide a source of green, blue, and red light. Use of light source 1502 configured to emit a particular wavelength of light, such as an LED, can eliminate the need for separate spectral selection means 1552 and 1554. A single image capturing means 1560 can be used to capture the reflected image from each of the three LED's. For example, a single color camera sensitive to multiple wavelengths (green, blue, and red) can be used to capture the reflected image from each of the three (green, blue, and red) LED's.

Image capturing means 1560 is coupled to image correcting and analyzing means 1580. Image correcting and analyzing means 1580 can be a computer or other type of processing system (explained in more detail below with respect to FIG. 16). A signal 1562 representing the reflected image captured by image capturing means 1560 is sent by image capturing means 1560 and received by image correcting and analyzing means 1580. Similarly, image capturing means 1570 is coupled to image correcting and analyzing means 1580. A signal 1572 representing the reflected image captured by image capturing means 1570 is sent by image capturing means 1570 and received by image correcting and analyzing means 1580. Image correcting and analyzing means 1580 carries out the processing and analysis of the reflected images received. Particularly, image correcting and analyzing means 1580 can be used to carry out steps 220–240 shown in FIG. 2. Image correcting and analyzing means 1580 can be configured to carry out these steps through hardware, software, or a combination of hardware and software.

Figure 16:
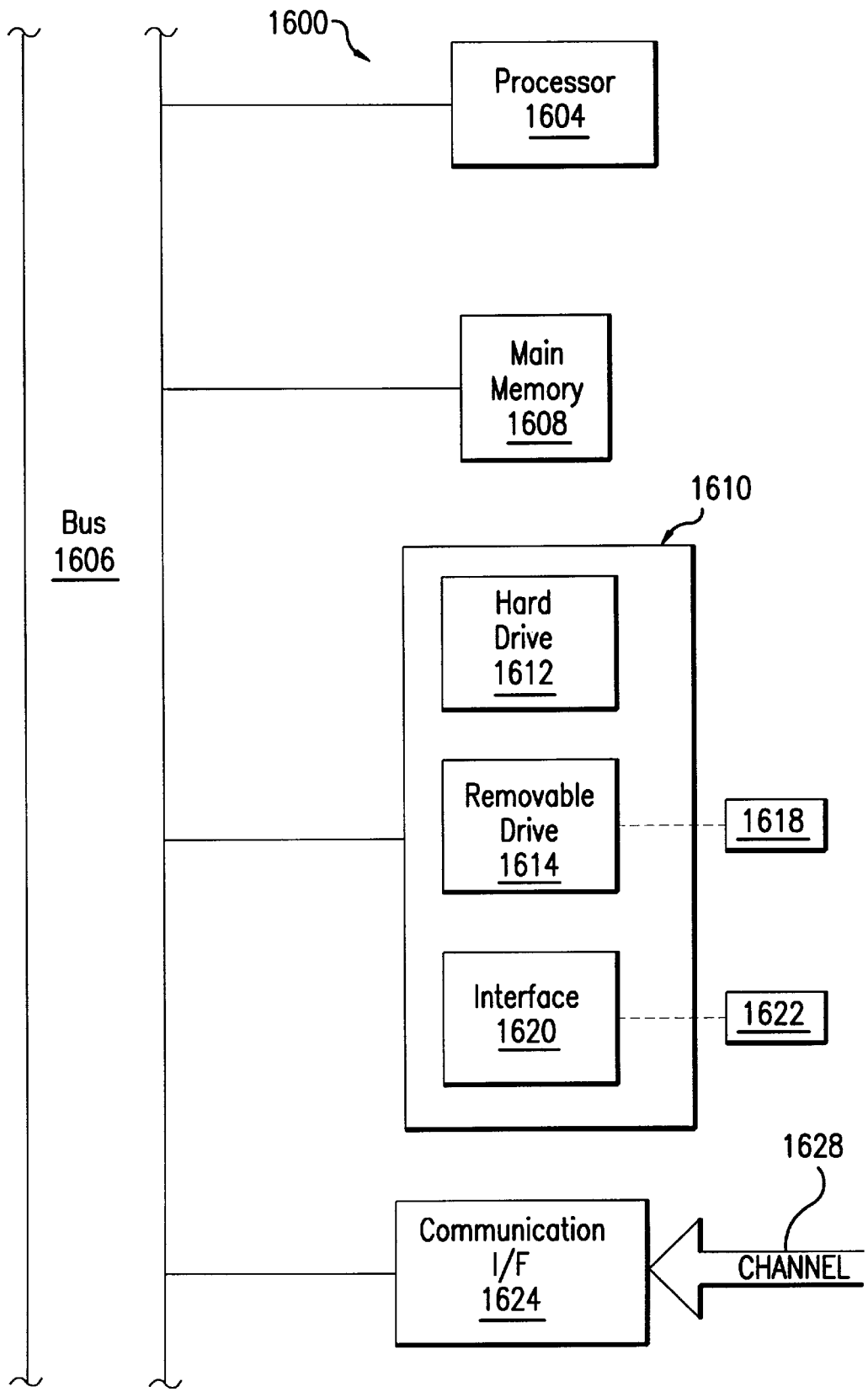
FIG. 16 shows a block diagram of a computer system suitable for use in the present invention.

An exemplary image correcting and analyzing means 1580 for use in the present invention is shown as a computer system 1600 in FIG. 16. Computer system 1600 includes one or more processors, such as processor 1604. Processor 1604 is connected to a communication bus 1606. Various software embodiments are described in terms of this exemplary computer system. After reading this description, it will become apparent to a person skilled in the relevant art how to implement the invention using other computer systems and/or computer architectures.

Computer system 1600 also includes a main memory 1608, preferably random access memory (RAM), and can also include a secondary memory 1610. Secondary memory 1610 can include, for example, a hard disk drive 1612 and/or a removable storage drive 1614, representing a floppy disk drive, a magnetic tape drive, an optical disk drive, etc. Removable storage drive 1614 reads from and/or writes to a removable storage unit 1618 in a well known manner. Removable storage unit 1618 represents a floppy disk, magnetic tape, optical disk, etc. which is read by and written to by removable storage drive 1614. As will be appreciated, removable storage unit 1618 includes a computer usable storage medium having stored therein computer software and/or data.

In alternative embodiments, secondary memory 1610 may include other similar means for allowing computer programs or other instructions to be loaded into computer system 1600. Such means can include, for example, a removable storage unit 1622 and an interface 1620. Examples of such can include a program cartridge and cartridge interface (such as that found in video game devices), a removable memory chip (such as an EPROM, or PROM) and associated socket, and other removable storage units 1622 and interfaces 1620 which allow software and data to be transferred from removable storage unit 1622 to computer system 1600.

Computer system 1600 can also include a communications interface 1624. Communications interface 1624 allows software and data to be transferred between computer system 1600 and external devices, such as image capturing means 1560 and 1570. Examples of communications interface 1624 can include a modem, a network interface (such as an Ethernet card), a communications port, a PCMCIA slot and card, etc. Software and data transferred via communications interface 1624 are in the form of signals which can be electronic, electromagnetic, optical or other signals capable of being received by communications interface 1624. For example, signals 1562 and 1572 are provided to communications interface via a channel 1628. Channel 1628 carries signals 1562 and 1572 and can be implemented using wire or cable, fiber optics, a phone line, a cellular phone link, an RF link and other communications channels.

In this document, the terms "computer program medium" and "computer usable medium" are used to generally refer to media such as removable storage device 1618, a hard disk installed in hard disk drive 1612, and signals provided via channel 1628. These computer program products are means for providing software to computer system 1600.

Computer programs (also called computer control logic) are stored in main memory 1608 and/or secondary memory 1610. Computer programs can also be received via communications interface 1624. Such computer programs, when executed, enable computer system 1600 to perform the features of the present invention as discussed herein. In particular, the computer programs, when executed, enable processor 1604 to perform the features of the present invention. Accordingly, such computer programs represent controllers of computer system 1600.

In an embodiment where the invention is implemented using software, the software may be stored in a computer program product and loaded into computer system 1600 using removable storage drive 1614, hard drive 1612 or communications interface 1624. The control logic (software), when executed by the processor 1604, causes processor 1604 to perform the functions of the invention as described herein.

In another embodiment, the invention is implemented primarily in hardware using, for example, hardware components such as application specific integrated circuits (ASICs). Implementation of the hardware state machine so as to perform the functions described herein will be apparent to persons skilled in the relevant art(s).

In yet another embodiment, the invention is implemented using a combination of both hardware and software.

Figure 17A:
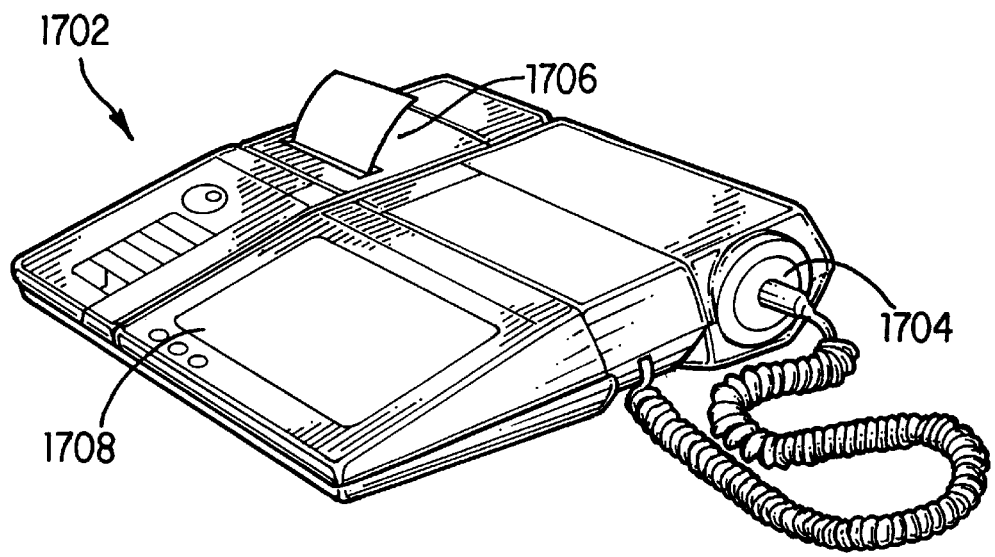
FIGS. 17A and 17B show embodiments of the present invention suitable for use with a subject.
Figure 17B:
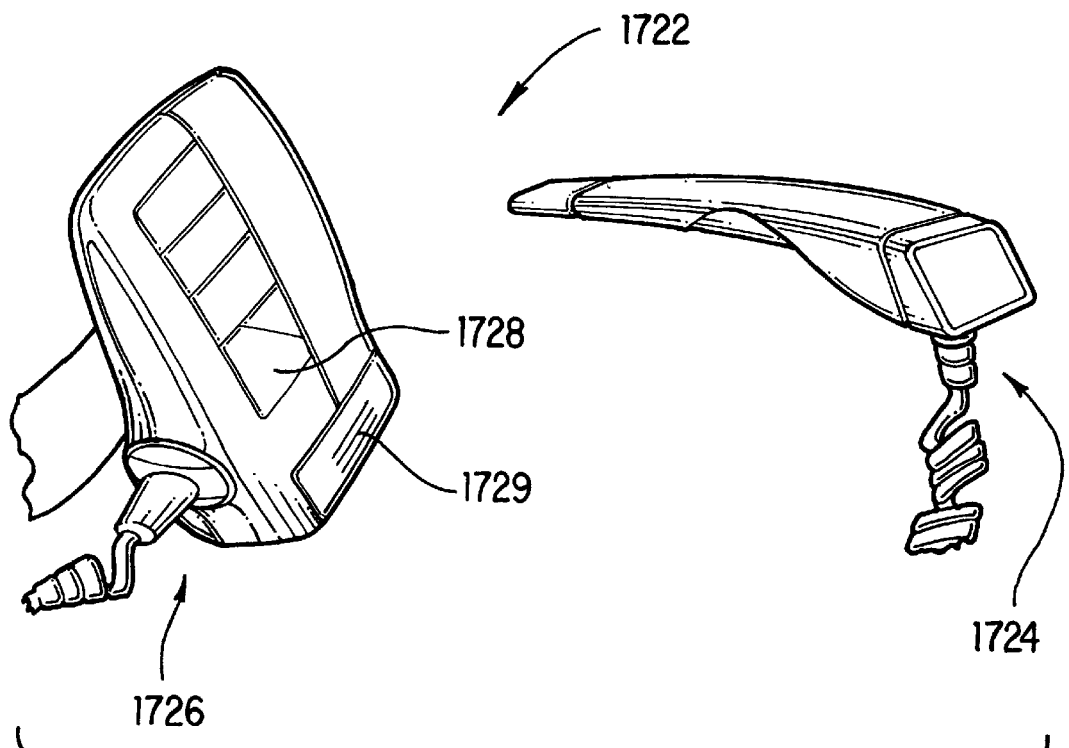

FIGS. 17A and 17B show embodiments of the present invention suitable for use with a subject for performing non-invasive in vivo analysis. FIG. 17A shows a console unit 1702 that contains a probe 1704, a printer 1706, and a processing and storage unit 1708. Probe 1704 is used to image the portion of the subject's vascular system, such as the inside of the lower lip. An index matching medium, such as ethyl cellulose available under the trade name "K Y" Jelly from Johnson & Johnson, or a sugar syrup, is preferably applied to probe 1704 to provide a good optical contact or optical seal between probe 1704 and the inside of the lower lip.

Probe 1704 is preferably equipped with the elements shown in FIG. 15 from light source 1502 through one or more image capturing means. To ensure optimal performance of the apparatus of the present invention, there should not be anything in the light path between polarizer 1510 and polarizer 1520 that de-polarizes the light. For example, the presence of dust in the light path between polarizer 1510 and polarizer 1520 will degrade the performance of the apparatus. Further, the components of probe 1704 are preferably made of non-depolarizing material so that the materials will not de-polarize the light. A particularly preferred material for the components of probe 1704 in the light path is a non-depolarizing plastic material available from Kodak with the trade name KODACEL. Other suitable materials for components in the light path are glass or quartz. A preferred material for the imaging end of probe 1704 is glass. A signal (such as signal 1562 or 1572 shown in FIG. 15) is transmitted from probe 1704 to processing and storage unit 1708 for processing and storage.

FIG. 17B shows a mobile unit 1722. Mobile unit 1722 includes a probe 1724 and a belt unit 1726. Probe 1724 can be configured in a similar manner to probe 1704 shown in FIG. 17A. Belt unit 1726 includes a data storage and transmission unit 1728. Data storage and transmission unit 1728 receives signals from probe 1724. These signals can be stored by data storage and transmission unit 1728 for processing at a later time. Alternatively, these signals can be transmitted by data storage and transmission unit 1728 to a central processing station (not shown) for processing and storage. The central processing station can be configured to provide permanent storage for the processed data, as well as to print and display the results in a well known manner. Belt unit 1726 also includes a location 1729 for batteries or other suitable power supply.

The in vivo apparatus of the present invention can be used to carry out the methods of the present invention discussed above. Particularly, the in vivo apparatus can be used to determine hemoglobin and bilirubin concentrations per unit volume of blood. The in vivo apparatus can also be used to determine the hematocrit and the mean cell volume. The in vivo apparatus can also be used to determine the number of white blood cells and the number of platelets per unit volume of blood. For determining the number of cells, such as white blood cells or platelets, the light source is configured as a pulsed light source or flash to "stop action" in the analysis image so the count can be made. The stop action achieved with the pulsed light source avoids the blurring associated with movement in the analysis image. The pulsed light source is preferably synchronized with the frame rate of the image capturing means. Stop action can also be achieved by controlling shuttering on the image capturing means. A stop action image is preferred any time a count of cells is to be made in the analysis image. A stop action image can also be used to determine other non-cell-count parameters, such as Hb or Hct. However, such other parameters such as Hb and Hct can be determined with a non-stop action image as well.

Figure 8B:
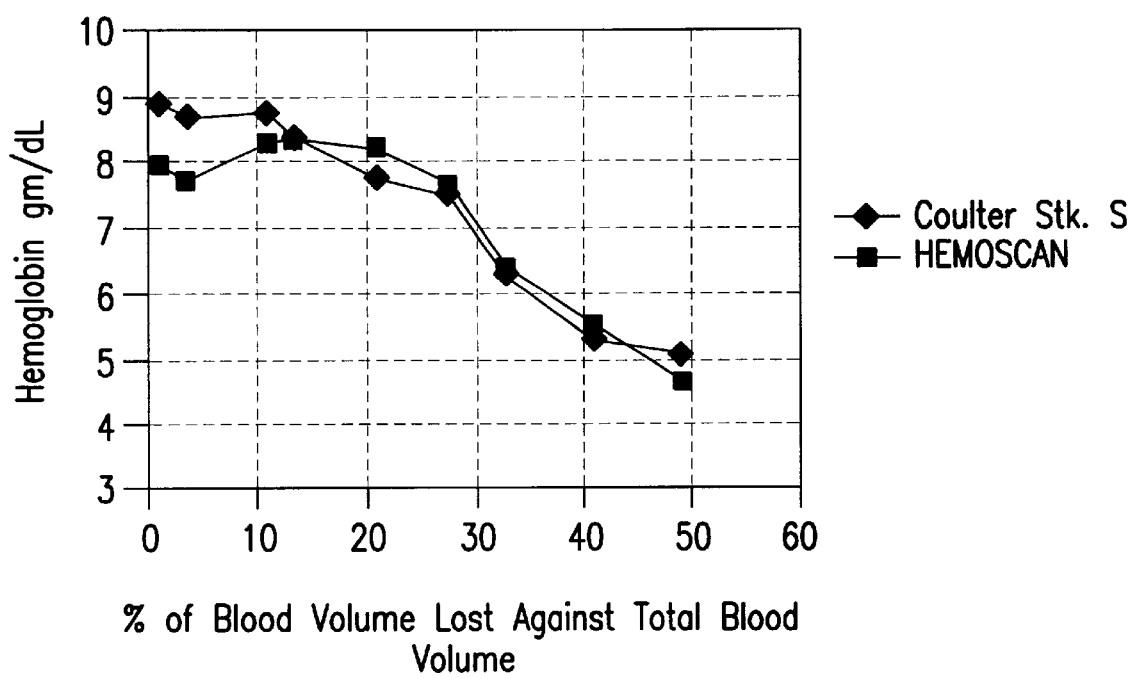
FIG. 8B shows a graph illustrating a Comparative Determination of Hemoglobin with Various Levels of Anemia (hemoglobin gm/dL as a function of % of blood volume lost against total blood volume)

An experiment was conducted to compare laboratory measurements using a conventional laboratory apparatus with measurements using an in vivo apparatus at different levels of anemia in a piglet. The piglet was bled down while a saline drip kept the piglet's fluid volume constant. Hemoglobin was measured at various points during the bleed down by extracting blood samples and using a conventional Coulter laboratory apparatus and the in vivo apparatus. FIG. 8B shows a graph illustrating a Comparative Determination of Hemoglobin with Various Levels of Anemia induced by bleed down (hemoglobin gm/dL as a function of % of blood volume lost against total blood-volume) for a Coulter Stk.S device and the in vivo apparatus FIG. 8B shows a high correlation (r=0.91) between the Coulter Stk. S results and the HEMOSCAN (in vivo apparatus) results.

Figure 8C:
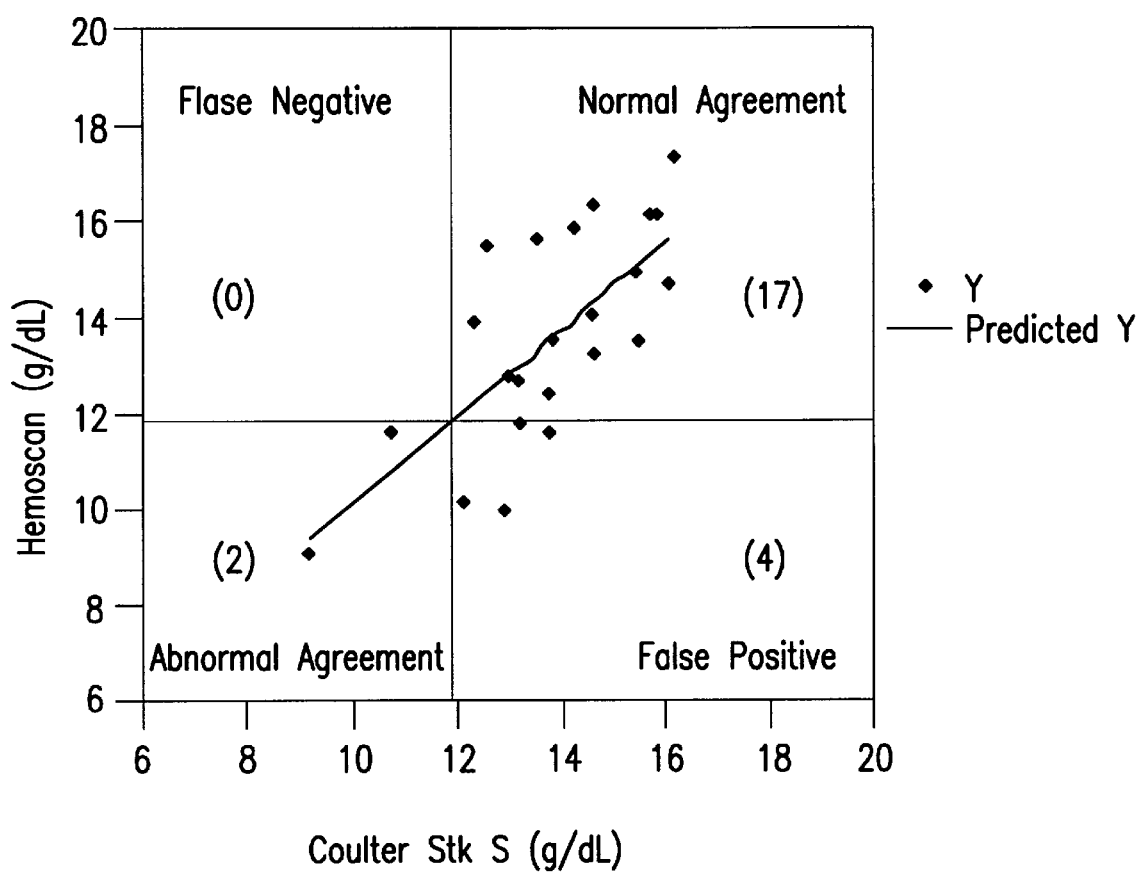
FIG. 8C shows a graph illustrating a Comparative Determination of Hemoglobin on 23 "Healthy" Human Subjects.

An experiment using an in vivo apparatus was carried out on 23 "healthy" human subjects. The procedure involved collecting reflected spectral images using a probe on the lip. The probe was placed inside the surface of a subject's lip (transmucosal membrane) with an optical contact or optical seal obtained by a small amount of "KY" jelly. FIG. 8C shows a graph illustrating the Comparative Determination of Hemoglobin on 23 "Healthy" Human Subjects using a Coulter Stk.S device and a HEMOSCAN in vivo apparatus. The results showed a predictive agreement of 83% with a correlation of r=0.68.

5. In Vitro and Other Analytical Applications

The cross-polarization technique of the present invention can be used to improve visualization of reflected images, and to improve the ability to perform quantitative analyses using reflected images in many applications other than non-invasive in vivo analysis of the vascular system. The cross-polarization technique of the present invention could readily be used for in vitro analysis of blood characteristics. The in vivo measurements discussed above could also be performed in vitro by imaging blood in, for example, a tube or flow cell. The cross-polarization technique of the present invention can be used to make in vitro measurements of quantitative blood concentration (Hb, Hct), blood counts (WBC, RBC, Plt), blood cell characteristics (MCV, MCHC, and granulocytes), and plasma constituents (bilirubin, labeled plasma components, and labeled cells).

The cross-polarization technique of the present invention can also be used to perform quantitative analytical measurement of dyes, inks, and chemical reactants that have been coated, for example, on an opaque surface. Such quantitative analyses are done in "strip testing" or strip readers, such as may be used in blood tests, pregnancy tests or glucose tests. The present invention can be used to make in vitro measurements of blood constituents on paper strips. The cross-polarization technique can also be used in applications requiring color matching between two or more color samples. The cross-polarization technique of the present invention can also be used in borescopic applications, or in an endoscope and orthoscope for clinical applications.

Figure 19:
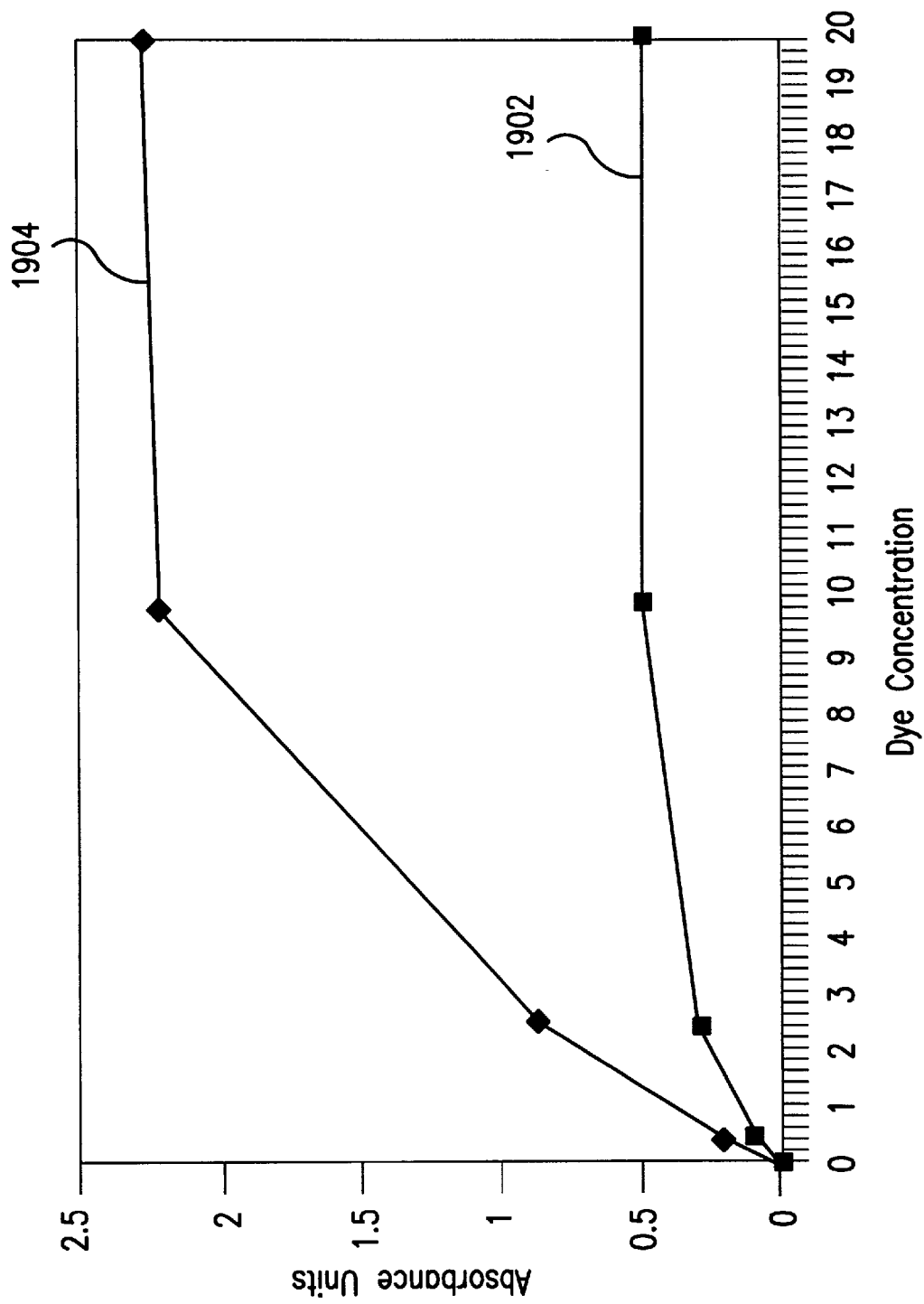
FIG. 19 shows a plot illustrating reflected spectrophotometry of red aniline dye.
Figure 20:
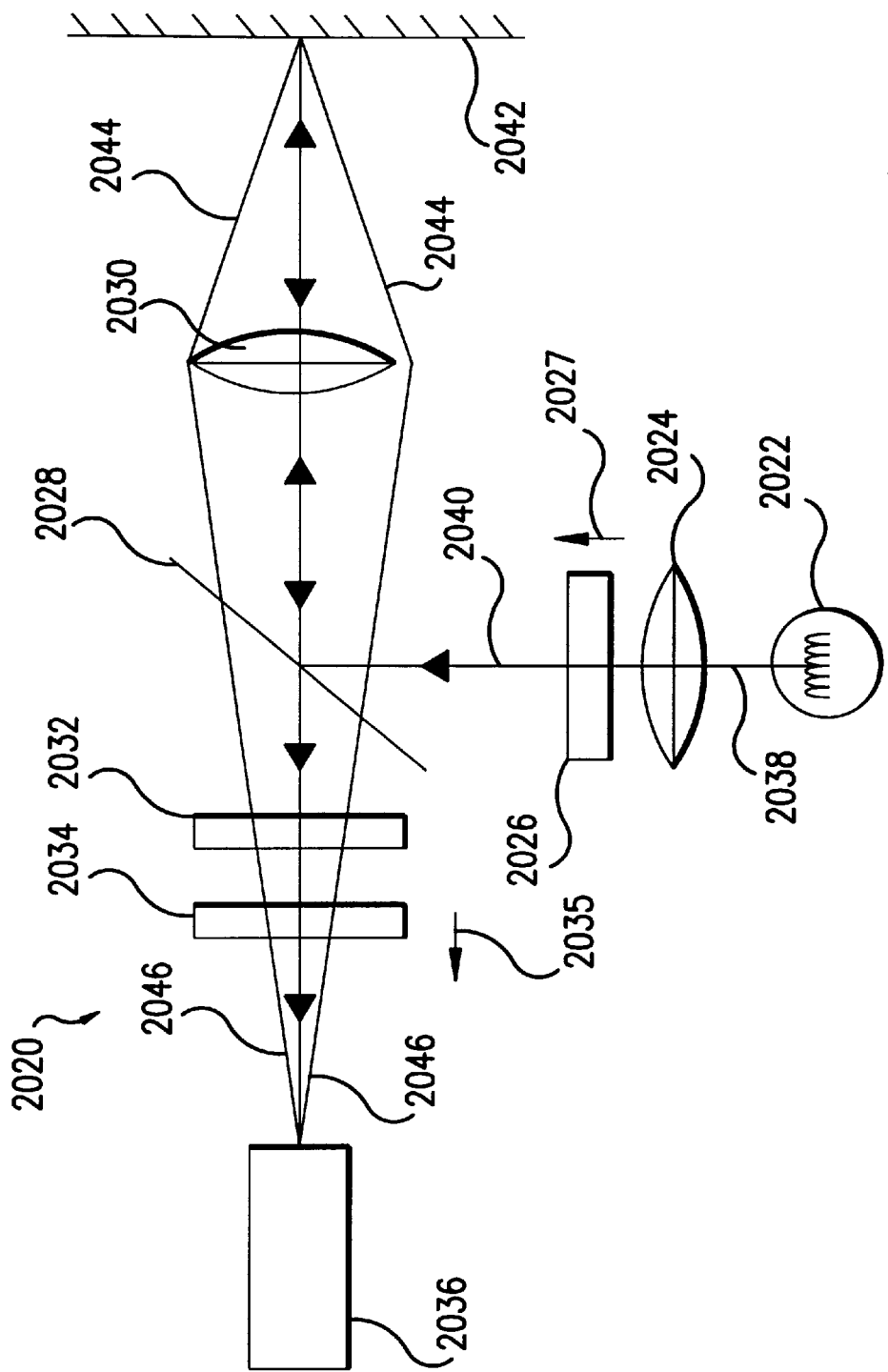
FIG. 20 shows a block diagram of one embodiment of a reflection colorimeter apparatus of the present invention.

FIG. 19 shows a graph of absorbance units as a function of dye concentration for four samples of red aniline dye (concentrations of 1, 3X, 10X, and 20X; see Table 1 below). Line 1902 represents data obtained for the four samples using a conventional reflected spectrophotometry instrument. Such conventional instruments typically have a small working range, generally from 0.0 to 0.5 Absorbance Unit, and, in the best case, from 0.0 to 1 Absorbance Unit. One Absorbance Unit represents a factor of 10 change in light intensity, either transmitted or reflected. The conventional apparatus becomes flat and non-responsive above 0.5 Absorbance Unit, and could not distinguish between the last two points (concentrations of 10X and 20X). Line 1902 is flat in this region. In contrast, line 1904 represents data obtained for the same four samples using a reflection colorimeter apparatus 2020 as shown in FIG. 20 that includes cross-polarizers. The working range using the reflection colorimeter apparatus of the present invention has been extended to more than two Absorbance Units (factor of 100). The limitation in measuring the last concentration (20X) using the reflection colorimeter apparatus of the present invention is the number of bits (8 bits) that were used in making the computations. An eight bit resolution ($2^8$=256) corresponds to approximately 2.41 Absorbance Units. To increase the number of Absorbance Units, additional bits are required. For example, ten bits ($2^{10}$=1024) corresponds approximately to three Absorbance Units (factor of 1000). To measure the 20X concentration, 15 bits would be required. The results of FIG. 19 indicate that the cross-polarization technique of the present invention can be used for color control of presses, fabric and dye lot control, strip testing, such as with paper, film, or latex, as well as in other areas requiring color differentiation.

TABLE 1

| Concentration | X-Polarized | Conventional |
| --- | --- | --- |
| 20X | 2.28 | 0.47 |
| 10X | 2.23 | 0.49 |
| 3X | 0.87 | 0.27 |
| 1 | 0.20 | 0.08 |
| 0 | 0.00 | 0.00 |

One embodiment of reflection colorimeter apparatus 2020 is shown in FIG. 20. Apparatus 2020 includes a light source 2022 and a condenser lens 2024. A first polarizer 2026, having a plane of polarization shown generally at 2027, is used to polarize light from light source 2022. First polarizer 2026 is disposed in a light path between light source 2022 and an object or reflecting substrate 2042 to be illuminated. In one embodiment, light source 2022 comprises first polarizer 2026 so that a separate first polarizer 2026 is not required. In such an embodiment, light source 2022 is a source of polarized light, such as a laser or a laser diode. A beam splitter 2028 reflects the light polarized by first polarizer 2026 through an objective lens 2030 onto object 2042.

A second polarizer 2034, having a plane of polarization shown generally at 2035, is disposed in a reflected light path between object 2042 and a detecting means 2036. Plane of polarization 2035 is 90° relative to plane of polarization 2027. A spectral selection means 2032, for example, a filter, for wavelength selection is disposed in the reflected light path.

In operation, illuminating light 2038 from light source 2022 passes through condenser lens 2024 and is polarized by first polarizer 2026. Polarized light 2040 reflects off beam splitter 2028 and is focused through objective lens 2030 onto object 2042. Reflected light 2044 from object 2042 passes through lens 2030, beam splitter 2028, spectral selection means 2032, and second polarizer 2034. Cross-polarized reflected light 2046 is detected by detecting means 2036.

Detecting means 2036 can be any device suitable for detecting reflected light 2046. Suitable detecting means include a photodetector, a photocell, or other device capable of detecting the reflected light intensity of reflected light 2046. Suitable detecting means 2036 also includes a camera. Apparatus 2020 can also be used to perform analysis of blood using blood in a tube or flow cell.

6. Conclusion

While various embodiments of the present invention have been described above, it should be understood that they have been presented by way of example only, and not limitation. For example, the cross-polarization technique of the present invention can be applied wherever it is desired to view circulation through tissue. The cross-polarization technique of the present invention can also be used to image stained tissue in situ. The cross-polarization technique of the present invention can be used in any analytical, in vivo, or in vitro application that requires optically measuring or visually observing reflecting characteristics of an object. Thus, the breadth and scope of the present invention should not be limited by any of the above-described exemplary embodiments, but should be defined only in accordance with the following claims and their equivalents.

What is claimed is:

1. An apparatus for analysis of blood by use of reflected spectral imaging, comprising:

a light source for illuminating blood, wherein a light path is formed between said light source and the illuminated blood;

a first polarizer for polarizing light from said light source;

image capturing means for capturing a reflected image reflected from the illuminated blood at a depth less than a multiple scattering length, the reflected image traveling along a reflected light path between the illuminated blood and said image capturing means; and a second polarizer disposed in the reflected light path between the illuminated blood and said image capturing means, wherein a plane of polarization of said second polarizer is 90° relative to a plane of polarization of said first polarizer.

2. The apparatus according to claim 1, wherein said light source comprises said first polarizer.

3. The apparatus according to claim 2, wherein said light source comprises a laser diode.

4. The apparatus according to claim 1, wherein said image capturing means comprises a charge coupled device (CCD) camera.

5. The apparatus according to claim 4, wherein said image capturing means further comprises a photodetector.

6. The apparatus according to claim 1, wherein said image capturing means comprises a photodetector.

7. The apparatus according to claim 1, further comprising:

a spectral selection means disposed in the reflected light path between said second polarizer and said image capturing means.

8. The apparatus according to claim 1, wherein said light source is a pulsed light.

9. The apparatus according to claim 1, further comprising:

image separating means disposed in the reflected light path between said second polarizer and said image capturing means for separating the reflected image into a first portion and a second portion.

10. The apparatus according to claim 9, wherein said image separating means comprises a dichroic mirror, wherein the first portion of the reflected image is transmitted through said dichroic mirror to said image capturing means, and the second portion of the reflected image is reflected by said dichroic mirror.

11. The apparatus of claim 10, further comprising:

a second image capturing means for capturing the second portion of the reflected image.

12. The apparatus of claim 11, wherein said second image capturing means comprises a charge coupled device (CCD) camera.

13. The apparatus of claim 11, further comprising:

a spectral selection means disposed in the reflected light path between said dichroic mirror and said second image capturing means.

14. The apparatus of claim 1, further comprising:

an image separating means disposed in the reflected light path between said second polarizer and said image capturing means for separating the reflected image into a plurality of portions, wherein a first portion of the reflected image is captured by said image capturing means.

15. The apparatus according to claim 14, further comprising:

a second image capturing means; and wherein said plurality of portions is two, and a second portion of the reflected image is captured by said second image capturing means.

16. The apparatus according to claim 15, further comprising:

a first spectral selection means disposed in the reflected light path between said image separating means and said image capturing means; and a second spectral selection means disposed in the reflected light path between said image separating means and said second image capturing means.

17. The apparatus according to claim 16, wherein said first spectral selection means is centered at a wavelength of 550 nm and said second spectral selection means is centered at a wavelength of 650 nm.

18. The apparatus according to claim 1, further comprising:
image correcting and analyzing means coupled to said image capturing means for correcting and analyzing the reflected image.

19. The apparatus according to claim 18, wherein said image correcting and analyzing means comprises a computer.

20. An apparatus for analysis of blood by use of reflected spectral imaging, comprising:
a light source for illuminating blood;
a beam splitter for forming a light path between said light source and the illuminated blood and a reflected light path for a reflected image reflected from the illuminated blood at a depth less than a multiple scattering length;
a first polarizer for polarizing light from said light source;
a camera for capturing the reflected image; and
a second polarizer disposed in the reflected light path between the illuminated blood and said camera, wherein a plane of polarization of said second polarizer is 90° relative to a plane of polarization of said first polarizer.

21. The apparatus according to claim 20, wherein said light source comprises said first polarizer.

22. The apparatus according to claim 21, wherein said light source comprises a laser diode.

23. The apparatus according to claim 20, wherein said light source is a pulsed light.

24. The apparatus according to claim 20, further comprising:
a heat rejection filter disposed in the light path between said light source and the illuminated blood.

25. The apparatus according to claim 20, further comprising:
an objective lens disposed between said beam splitter and the illuminated blood for magnifying the reflected image, wherein said camera is in a magnified image plane of said objective lens.

26. The apparatus of claim 20, further comprising:
a dichroic mirror disposed in the light path between said second polarizer and said camera for separating the reflected image, wherein a first portion of the reflected image is transmitted through said dichroic mirror to said camera, and a second portion of the reflected image is reflected by said dichroic mirror; and
an image capturing means for capturing the second portion of the reflected image.

27. The apparatus according to claim 26, wherein said image capturing means comprises a second camera.

28. The apparatus according to claim 27, further comprising:
a first spectral selection filter disposed in the light path between said dichroic mirror and said camera; and
a second spectral selection filter disposed in the light path between said dichroic mirror and said second camera.

29. The apparatus according to claim 28, wherein said first spectral selection filter is centered at a wavelength of 550nm and said second spectral selection filter is centered at a wavelength of 650 nm.

30. The apparatus according to claim 26, wherein said image capturing means comprises a photodetector.

31. The apparatus according to claim 20, further comprising:
a computer coupled to said camera for analyzing the reflected image.

32. A method for analysis of blood, comprising:
(1) imaging blood to produce a raw reflected image reflected from a depth less than a multiple scattering length, comprising
  (a) illuminating the blood with light polarized by a first polarizer and
  (b) capturing a reflected image reflected from the blood, wherein the reflected image is passed through a second polarizer having a lane of polarization 90° relative to a plane of polarization of the first polarizer to produce the raw reflected image;
(2) applying a correction to the raw reflected image to form a corrected reflected image;
(3) segmenting a scene from the corrected reflected image to form an analysis image; and
(4) analyzing the analysis image for a characteristic of the blood.

33. The method of claim 32, wherein step (2) comprises:
(a) applying a first wavelength filter to the raw reflected image to form a first filtered image;
(b) applying a second wavelength filter to the raw reflected image to form a second filtered image;
(c) taking the negative logarithm of the quotient obtained by dividing the first filtered image by the second filtered image to form the corrected reflected image.

34. The method of claim 33, wherein the first wavelength filter is centered at a first wavelength located at an isobestic point.

35. The method of claim 33, wherein the first wavelength filter is centered at a first wavelength of 550 nm and the second wavelength filter is centered at a second wavelength of 650 nm.

36. The method of claim 32, wherein step (2) comprises applying a velocity correction so that a moving portion of the raw reflected image is extracted from a stationary portion of the raw reflected image to form the corrected reflected image.

37. The method of claim 32, wherein step (3) comprises:
(a) applying an optical intensity criterion to the corrected reflected image.

38. The method of claim 37, wherein step (3) further comprises:
(b) applying a size criterion to the corrected reflected image.

39. The method of claim 38, wherein the size criterion is used to segment large vessels into the analysis image, wherein large vessels are of sufficient size so that a plurality of red blood cells flow side-by-side through them.

40. The method of claim 38, wherein the size criterion is used to segment small vessels into the analysis image, wherein small vessels are of a size so that red blood cells flow substantially single file through them.

41. The method of claim 38, wherein step (3) further comprises:
(c) applying a shape criterion to the corrected reflected image.

42. The method of claim 32, wherein step (3) comprises using spatial frequency to segment the scene from the corrected reflected image.

43. The method of claim 32, wherein step (4) comprises:
   (a) determining a mean reflected light intensity of the analysis image; and
   (b) converting the mean reflected light intensity of the analysis image into a hemoglobin concentration per unit volume of blood.

44. The method of claim 32, wherein step (4) comprises:
   (a) counting white blood cells in the analysis image to determine a number of white blood cells per unit volume of blood.

45. The method of claim 32, wherein step (4) comprises:
   (a) determining a mean cell volume from the analysis image.

46. The method of claim 32, wherein step (4) comprises:
   (a) counting platelets in the analysis image to determine a number of platelets per unit volume of blood.

47. The method of claim 32, wherein step (4) comprises:
   (a) measuring a volume of cells per unit volume of blood in the analysis image to determine hematocrit.

48. The method of claim 32, wherein step (4) comprises:
   (a) measuring a volume of cells per unit volume of blood in the analysis image to determine hematocrit (Hct);
   (b) determining a mean reflected light intensity of the analysis image;
   (c) converting the mean reflected light intensity of the analysis image into a hemoglobin concentration per unit volume of blood (Hb); and
   (d) determining a mean cell volume (MCV) from the analysis image.

49. The method of claim 48, further comprising:
   (5) determining a red blood cell count (RBC) from the equation $$RBC = Hct/MCV.$$

50. The method of claim 48, further comprising:
   (5) determining a mean cell hemoglobin concentration (MCHC) from the analysis image.

51. The method of claim 50, further comprising:
   (5) determining a mean cell hemoglobin from the equation $$MCH = MCV \times MCHC.$$

52. The method of claim 32, wherein the analysis image is segmented from the corrected reflected image so that the analysis image includes capillary plasma.

53. The method of claim 52, wherein step (4) comprises:
   (a) determining a mean reflected light intensity of the analysis image; and
   (b) converting the mean reflected light intensity of the analysis image into a bilirubin concentration per unit volume of blood.

54. The method of claim 53, wherein step (2) comprises:
   (a) applying a first wavelength filter to the raw reflected image to form a first filtered image;
   (b) applying a second wavelength filter to the raw reflected image to form a second filtered image;
   (c) taking the negative logarithm of the quotient obtained by dividing the first filtered image by the second filtered image to form the corrected reflected image.

55. The method of claim 54, wherein the first wavelength filter is centered at a first wavelength of 450 nm and the second wavelength filter is centered at a second wavelength of 600 nm.

56. The method of claim 52, wherein step (4) comprises:
   (a) detecting optical contrast produced by a marker introduced into the blood.

57. The method of claim 56, wherein the marker is used to detect compounds in the capillary plasma.

58. The method of claim 56, wherein the marker is used to detect compounds that attach to cells in the blood.

59. The method of claim 52, wherein step (4) comprises:
   (a) detecting natural constituents of plasma.

60. The method of claim 52, wherein step (4) comprises:
   (a) detecting non-natural components of plasma.

61. A method for non-invasive, in vivo analysis of blood in large vessels, comprising:
   (1) illuminating a portion of a subject's vascular system with light polarized by a first polarizer;
   (2) capturing a reflected image reflected from the illuminated portion, wherein the reflected image is passed through a second polarizer having a plane of polarization 90° relative to a plane of polarization of the first polarizer to produce a raw reflected image;
   (3) applying a correction to the raw reflected image to form a corrected reflected image;
   (4) segmenting a scene from the corrected reflected image that includes large vessels to form an analysis image, wherein large vessels are of sufficient size so that a plurality of red blood cells flow side-by-side through them; and
   (5) analyzing the analysis image for a characteristic of blood in large vessels.

62. The method of claim 61, wherein step (4) comprises applying at least one of:
   (a) an optical intensity criterion to the corrected reflected image to form an intensity-corrected reflected image;
   (b) a size criterion to the intensity-corrected reflected image to form an intensity-and-size-corrected reflected image; and
   (c) a shape criterion to the intensity-and-size-corrected reflected image to form the analysis image.

63. The method of claim 62, wherein step (5) comprises:
   (a) determining a mean reflected light intensity of the analysis image; and
   (b) converting the mean reflected light intensity of the analysis image into a hemoglobin concentration per unit volume of blood (Hb).

64. The method of claim 63, wherein step (3) comprises applying a bi-chromatic correction using a first wavelength centered at 550 nm and a second wavelength centered at 650 nm.

65. The method of claim 62, wherein step (5) comprises:
   (a) measuring a volume of cells per unit volume of blood in the analysis image to determine hematocrit (Hct).

66. The method of claim 61, wherein step (2) is performed using stop action.

67. The method of claim 66, wherein step (5) comprises:
   (a) counting white blood cells in the analysis image to determine a number of white blood cells per unit volume of blood.

68. The method of claim 67, wherein step (1) is performed using light in the range from 400 nm to 600 nm.

69. The method of claim 66, wherein step (5) comprises:
   (a) counting granulocytes in the analysis image; and
   (b) counting agranulocytes in the analysis image.

70. The method of claim 61, wherein step (5) comprises:
   (a) detecting optical contrast produced by a marker introduced into the subject's vascular system.

71. The method of claim 70, wherein the marker is used to detect compounds that attach to cells in the subject's vascular system.

72. The method of claim 61, wherein step (5) comprises:
(a) detecting a hemoglobin complex.

73. A method for non-invasive, in vivo analysis of blood in small vessels, comprising:
(1) illuminating a portion of a subject's vascular system with light polarized by a first polarizer;
(2) capturing a reflected image reflected from the illuminated portion, wherein the reflected image passes through a second polarizer having a plane of polarization 90° relative to a plane of polarization of the first polarizer to produce a raw reflected image;
(3) applying a correction to the raw reflected image to form a corrected reflected image;
(4) segmenting a scene from the corrected reflected image that includes small vessels to form an analysis image, wherein small vessels are of a size so that red blood cells flow substantially single file through them; and
(5) analyzing the analysis image for a characteristic of blood in small vessels.

74. The method of claim 73, wherein step (2) is performed using stop action.

75. The method of claim 74, wherein step (5) comprises:
(a) counting platelets in the analysis image to determine a number of platelets per unit volume of blood.

76. The method of claim 73, wherein the analysis image is segmented from the corrected reflected image so that the analysis image includes capillary plasma.

77. The method of claim 76, wherein step (5) comprises:
(a) determining a mean reflected light intensity of the analysis image; and
(b) converting the mean reflected light intensity of the analysis image into a bilirubin concentration per unit volume of blood.

78. The method of claim 77, wherein step (3) comprises applying a bi-chromatic correction using a first wavelength centered at 450 nm and a second wavelength centered at 600 nm.

79. The method of claim 76, wherein step (5) comprises:
(a) detecting optical contrast produced by a marker.

80. The method of claim 79, wherein the marker is used to detect compounds in the capillary plasma.

81. The method of claim 79, wherein the marker is used to detect compounds that attach to cells.

82. The method of claim 73, wherein step (5) comprises:
(a) determining a mean cell volume from the analysis image.

83. The method of claim 73, wherein step (5) comprises:
(a) determining a mean cell hemoglobin concentration (MCHC) from the analysis image.

84. The method of claim 83, wherein step (3) comprises:
(a) applying a bi-chromatic correction using a first wavelength centered at 550 nm and a second wavelength centered at 650 nm.

85. The method of claim 73, wherein step (3) comprises:
(a) applying a velocity correction to the raw reflected image to from the corrected reflected image.

86. The method of claim 73, wherein step (4) comprises applying at least one of:
(a) an optical intensity criterion to the corrected reflected image to form an intensity-corrected reflected image;
(b) a size criterion to the intensity-corrected reflected image to form an intensity-and-size-corrected reflected image; and
(c) a shape criterion to the intensity-and-size-corrected reflected image to form the analysis image.

87. The method of claim 73, wherein step (5) comprises:
(a) detecting natural constituents of plasma.

88. The method of claim 73, wherein step (5) comprises:
(a) detecting non-natural components of plasma.

89. Apparatus for optically penetrating an object and detecting subsurface optical characteristics of an object, comprising:
a light source for illuminating an object at a wavelength such that the multiple scattering depth is small compared to the penetration depth of the illuminating light;
a first polarizer for polarizing light from said light source;
imaging means for detecting an image reflected from beneath the surface of the illuminated object; and
a second polarizer disposed in a reflected light path between the object and said imaging means through which the scattered light passes, wherein a plane of polarization of said second polarizer is substantially orthogonal relative to a plane of polarization of said first polarizer.

90. The apparatus according to claim 89, further comprising:
an objective lens disposed between said first polarizer and the object, wherein said imaging means is in a magnified image plane of said objective lens.

91. The apparatus according to claim 89, further comprising:
reflected light separating means disposed in the reflected light path between said second polarizer and said imaging means for separating the reflected light reflected from the illuminated object, wherein a first portion of the reflected light is transmitted through said reflected light separating means to said imaging means, and a second portion of the reflected light is reflected by said reflected light separating means; and
a second imaging means for imaging the second portion of the reflected light.

92. The apparatus according to claim 91, further comprising:
a first spectral selection means disposed in the reflected light path between said reflected light separating means and said imaging means; and
a second spectral selection means disposed in the reflected light path between said reflected light separating means and said second imaging means.

93. The apparatus according to claim 89, wherein said imaging means comprises a camera.

94. The apparatus according to claim 93, wherein said imaging means further comprises a photodetector.

95. The apparatus according to claim 89, wherein said imaging means comprises a photodetector.

96. The apparatus according to claim 89, further comprising:
a dichroic separator disposed in the reflected light path between said second polarizer and said imaging means.

97. The apparatus according to claim 89, wherein said light source comprises said first polarizer.

98. The apparatus according to claim 97 wherein said light source comprises a laser diode.

99. The apparatus according to claim 89, wherein said light source is monochromatic.

100. The apparatus according to claim 99, wherein said light source comprises a light emitting diode (LED).

101. The apparatus according to claim 99, wherein said light source is polarized.

102. The apparatus according to claim 101, wherein said light source comprises a laser.

103. Apparatus for quantitatively measuring absorption properties of an imaged object, comprising:

a light source for illuminating an object to be imaged;

a first polarizer for polarizing light from said light source;

imaging means for detecting an image reflected from the illuminated object;

a second polarizer disposed in a reflected light path between the object and said imaging means, wherein a plane of polarization of said second polarizer is substantially orthogonal relative to a plane of polarization of said first polarizer; and measuring means coupled to said imaging means for quantitatively measuring differences in absorption properties between imaged structures using said reflected light image.

* * * * *

UNITED STATES PATENT AND TRADEMARK OFFICE
CERTIFICATE OF CORRECTION

PATENT NO. : 5,983,120
DATED : November 9, 1999
INVENTOR(S) : Groner et al.

It is certified that error appears in the above-indentified patent and that said Letters Patent is hereby corrected as shown below:

On the title page, in item [45], please replace "Nov. 9, 1999" with --*Nov. 9, 1999--.

On the title page, between items [73] and [21], please insert the following:

--[*] Notice: This patent issued on a continued prosecution application filed under 37 CFR 1.53(d), and is subject to the twenty year patent term provisions of 35 U.S.C. 154(a)(2).--

On the title page, in item [56], please add the following cited references:

- Ren et al., "Polarized-Light Intravital Microscopy for Study of Cochlear Microcirculation," *Microvascular Research*, Vol. 46, 1993, pp. 383-393.

- Slaaf, D.W. et al., "A versatile incident illuminator for intravital microscopy," *Int. J. Microcirc: Clin Exp 6*, pp. 391-397 (1987).

- "ADC-500; Advanced computer pattern recognition technique for improved precision and accuracy," date unknown.

- Bacus et al., "An Automated Method of Differential Red Blood Cell Classification with Application to the Diagnosis of Anemia," *The Journal of Histochemistry and Cytochemistry*, Vol. 25, No. 7, pp. 614-632, 1977.

UNITED STATES PATENT AND TRADEMARK OFFICE
CERTIFICATE OF CORRECTION

PATENT NO. : 5,983,120
DATED : November 9, 1999
INVENTOR(S) : Groner et al.

It is certified that error appears in the above-indentified patent and that said Letters Patent is hereby corrected as shown below:

— Bacus *et al.*, "Image Processing for Automated Erythrocyte Classification," *The Journal of Histochemistry and Cytochemistry*, pp. 195-201, 1976.

In column 34, line 6, delete the second occurrence of "and".

In column 34, line 11, after "polarizer", insert --and measuring means coupled to said image capturing means for quantitatively measuring differences in absorption properties between imaged structures as a function of Beer's Law using said reflected image--.

In column 35, line 24, delete the second occurrence of "and".

In column 35, line 29, after "polarizer", insert --and measuring means coupled to said image capturing means for quantitatively measuring differences in absorption properties between imaged structures as a function of Beer's Law using said reflected image--.

In column 40, delete lines 7-21 and insert therefor the following claim:

--89. Apparatus for quantitatively measuring absorption properties of an imaged object, comprising:

a light source for illuminating an object to be imaged;

a first polarizer for polarizing light from said light source;

UNITED STATES PATENT AND TRADEMARK OFFICE
CERTIFICATE OF CORRECTION

PATENT NO. : 5,983,120
DATED : November 9, 1999
INVENTOR(S) : Groner et al.

It is certified that error appears in the above-indentified patent and that said Letters Patent is hereby corrected as shown below:

imaging means for detecting an image reflected from the illuminated object;

a second polarizer disposed in a reflected light path between the object and said imaging means, wherein a plane of polarization of said second polarizer is substantially orthogonal relative to a plane of polarization of said first polarizer; and measuring means coupled to said imaging means for quantitatively measuring differences in absorption properties between imaged structures as a function of Beer's Law using said reflected image.--.

In column 40, lines 34, 36 and 39, replace "light" with --image--.

In column 41, delete lines 3-10.

In column 42, delete lines 1-7.

Signed and Sealed this

Twenty-seventh Day of March, 2001

Attest:

NICHOLAS P. GODICI

Attesting Officer

Acting Director of the United States Patent and Trademark Office